United States Patent
Kullok et al.

(12) 
(10) Patent No.: US 6,644,976 B2
(45) Date of Patent: Nov. 11, 2003

(54) APPARATUS, METHOD AND COMPUTER PROGRAM PRODUCT TO PRODUCE OR DIRECT MOVEMENTS IN SYNERGIC TIMED CORRELATION WITH PHYSIOLOGICAL ACTIVITY

(76) Inventors: Saul Kullok, Flat 3, 6 Queens Road, London NW4 2TH (GB); Jose R. Kullok, 9 Bringsdale Road, London NW4 1TB (GB)

( * ) Notice: Subject to any disclaimer, the term of this patent is extended or adjusted under 35 U.S.C. 154(b) by 0 days.

(21) Appl. No.: 09/948,792

(22) Filed: Sep. 10, 2001

(65) Prior Publication Data

US 2003/0068605 A1 Apr. 10, 2003

(51) Int. Cl.[7] ................... G09B 19/00; G09B 223/28; A63B 69/00
(52) U.S. Cl. .................... 434/236; 434/262; 434/247; 434/258; 128/905
(58) Field of Search .................. 434/236, 237, 434/238, 247, 258, 262; 482/900; 128/905; 600/545

(56) References Cited

U.S. PATENT DOCUMENTS

| | | |
|---|---|---|
| 2,737,183 A | 3/1956 | Giaimo |
| 3,344,792 A | 10/1967 | Offner et al. |
| 3,881,496 A | 5/1975 | Vredenbregt et al. |
| 3,928,924 A | 12/1975 | Taska |
| 3,941,137 A | 3/1976 | Vredenbregt et al. |

(List continued on next page.)

FOREIGN PATENT DOCUMENTS

| | | | |
|---|---|---|---|
| WO | WO 99/47096 | 9/1999 | .......... A61H/31/00 |
| WO | WO 00/06076 | 2/2000 | .......... A61H/23/04 |

OTHER PUBLICATIONS

Berne, R.M. and Levy, M.N., *Physiology*, The C.V. Mosby Company, ISBN No. 0–8016–1697–2, pp. ix, x, 257–279 and 398–430 (1988).

Everatt, J. et al., "Motor aspects of dyslexia," in Everatt, J. (ed.), *Reading and Dyslexia: Visual and attentional processes*, Routledge, ISBN No. 0–415–12327–5 (hc.), pp. v, vi and 122–136 (1999).

(List continued on next page.)

*Primary Examiner*—John Edmund Rovnak
(74) *Attorney, Agent, or Firm*—Sterne, Kessler, Goldstein & Fox P.L.L.C.

(57) ABSTRACT

An apparatus and method is presented for promoting movements of a subject in synergic timed correlation with physiological activity. The apparatus includes a synergic programs module that directs the movements in a temporally varying fashion. The synergic programs module causes generation of at least one signal, stimulus, or force, where the movements are performed in response to the at least one signal, stimulus, or force, where each of the at least one signal, stimulus, or force is determined so as to reduce meaning and/or emotional content to the subject, where each signal and stimulus is from a pool that comprises signals and stimuli that are sensorially understandable or recognizable by the subject, and where timing of the movements is based on at least a primary correlation factor and a secondary correlation factor. The primary correlation factor is determined so that the movements are synchronized with referential points of an intrinsically variable cyclical physiological activity. The secondary correlation factor is determined based on (a) fluctuations based on results of a first function; and (b) fluctuations based on a quantity of cycles of the physiological activity elapsing between any two of the movements or any two groupings of the movements, where the quantity of cycles is based on results of a second function.

24 Claims, 34 Drawing Sheets

U.S. PATENT DOCUMENTS

| | | | |
|---|---|---|---|
| 3,952,424 A | 4/1976 | Herr et al. | |
| 3,973,334 A | 8/1976 | Sterritt | |
| 3,976,058 A | 8/1976 | Tidwell | |
| 4,205,465 A | 6/1980 | Mannarino | |
| 4,392,830 A | 7/1983 | Salzman et al. | |
| 4,492,233 A | 1/1985 | Petrofsky et al. | |
| 4,499,900 A | 2/1985 | Petrofsky et al. | |
| 4,558,704 A | 12/1985 | Petrofsky | |
| 4,569,352 A | 2/1986 | Petrofsky et al. | |
| 4,586,510 A | 5/1986 | Glaser et al. | |
| 4,632,116 A | 12/1986 | Rosen et al. | |
| 4,642,769 A | 2/1987 | Petrofsky | |
| 4,669,477 A | 6/1987 | Ober | |
| 4,676,232 A | 6/1987 | Olsson et al. | |
| 4,697,808 A | 10/1987 | Larson et al. | |
| 4,711,242 A | 12/1987 | Petrofsky | |
| 4,724,842 A | 2/1988 | Charters | |
| 4,738,269 A | 4/1988 | Nashner | |
| 4,760,850 A | 8/1988 | Phillips et al. | |
| 4,785,813 A | 11/1988 | Petrofsky | |
| 4,796,631 A | 1/1989 | Grigoryev | |
| 4,798,197 A | 1/1989 | Nippoldt et al. | |
| 4,799,487 A | 1/1989 | Bleicher | |
| 4,863,157 A | 9/1989 | Mendel et al. | |
| 4,906,193 A | 3/1990 | McMullen et al. | |
| 4,984,158 A * | 1/1991 | Hillsman | 128/200.14 |
| 4,995,404 A | 2/1991 | Nemir | |
| 5,014,705 A | 5/1991 | Graupe et al. | |
| 5,016,635 A | 5/1991 | Graupe | |
| 5,081,989 A | 1/1992 | Graupe et al. | |
| 5,092,329 A | 3/1992 | Graupe et al. | |
| 5,111,814 A | 5/1992 | Goldfarb | |
| 5,117,813 A | 6/1992 | Haxton et al. | |
| 5,120,228 A | 6/1992 | Stahl et al. | |
| 5,167,229 A | 12/1992 | Peckham et al. | |
| 5,209,240 A | 5/1993 | Jain et al. | |
| 5,291,894 A | 3/1994 | Nagy | |
| 5,318,487 A * | 6/1994 | Golen et al. | 482/5 |
| 5,330,516 A | 7/1994 | Nathan | |
| 5,337,757 A | 8/1994 | Jain et al. | |
| 5,350,304 A | 9/1994 | Fula et al. | |
| 5,395,301 A * | 3/1995 | Russek | 601/41 |
| 5,435,728 A | 7/1995 | Fula et al. | |
| 5,476,103 A | 12/1995 | Nahsner | |
| 5,476,441 A | 12/1995 | Durfee et al. | |
| 5,529,498 A | 6/1996 | Cassily et al. | |
| 5,538,432 A | 7/1996 | Dondero et al. | |
| 5,562,707 A | 10/1996 | Prochazka et al. | |
| 5,575,294 A | 11/1996 | Perry et al. | |
| 5,588,841 A | 12/1996 | Mechling | |
| 5,595,488 A | 1/1997 | Gozlan et al. | |
| 5,597,309 A | 1/1997 | Riess | |
| 5,628,722 A | 5/1997 | Solomonow et al. | |
| 5,643,332 A | 7/1997 | Stein | |
| 5,657,996 A | 8/1997 | Radgowski et al. | |
| 5,662,693 A | 9/1997 | Johnson et al. | |
| 5,743,744 A | 4/1998 | Cassily et al. | |
| 5,759,198 A | 6/1998 | Karell | |
| 5,803,745 A | 9/1998 | Kozak et al. | |
| 5,814,093 A | 9/1998 | Stein | |
| 5,830,160 A | 11/1998 | Reinkensmeyer | |
| 5,843,142 A | 12/1998 | Sultan | |
| 5,861,017 A | 1/1999 | Smith et al. | |
| 5,895,363 A | 4/1999 | Preijde | |
| 5,897,325 A | 4/1999 | Koby-Olson | |
| 5,919,149 A | 7/1999 | Allum | |
| 5,961,541 A | 10/1999 | Ferrati | |
| 6,026,328 A | 2/2000 | Peckham et al. | |
| RE36,690 E | 5/2000 | McGraw et al. | |
| 6,064,911 A | 5/2000 | Wingrove | |
| 6,064,912 A | 5/2000 | Kenney | |
| 6,110,130 A | 8/2000 | Kramer | |
| 6,111,976 A | 8/2000 | Rylander | |
| 6,155,993 A | 12/2000 | Scott | |
| 6,159,014 A | 12/2000 | Jenkins et al. | |
| 6,162,059 A | 12/2000 | Murphy et al. | |
| 6,162,190 A | 12/2000 | Kramer | |
| 6,163,725 A | 12/2000 | Peckham et al. | |
| 6,273,088 B1 * | 8/2001 | Hillsman | 128/204.23 |

OTHER PUBLICATIONS

Sandman, C.A. et al., "Influence of Afferent Cardiovascular Feedback on Behavior and the Cortical Evoked Potential," in Cacioppo, J.T. and Petty, R.E. (eds.), *Perspectives in Cardiovascular Psychophysiology*, The Guilford Press, ISBN No. 0–89862–613–7, pp. xiii–xv and 189–222 (1982).

Allen, G.I. and Tsukahara N., "Cerebrocerebellar Communication Systems," *Physiological Reviews*, vol. 54, No. 4, pp. 957–1006 (Oct. 1974).

Astley, C.A. et al., "Integrating behavior and cardiovascular responses: the code," *Cardiovascular Responses and Behavior*, The American Physiological Society, pp. R172–R181 (1991).

Bechara, A. et al., "Deciding Advantageously Before Knowing the Advantageous Strategy," *Science*, vol. 275, pp. 1293–1295 (Feb. 28, 1997).

Walker, B., and Sandman, C.A., "Physiological Response Patterns in Ulcer Patients: Phasic and Tonic Components of the Electrogastrogram," *Psychophysiology*, vol. 14, No. 4, The Society for Psychophysiological Research pp. 393–400 (1977).

Bernstein, N., *The Co–ordination and Regulation of Movements*, Pergamon Press, Entire book submitted (1967).

Collet, C. et al., "Autonomic responses correlate to motor anticipation," *Behavioural Brain Research 63*, pp. 71–79 (1994).

Deecke, L. et al., "Distribution of Readiness Potential, Pre–motion Positivity, and Motor Potential of the Hyman Cerebral Cortex Preceding Voluntary Finger Movements," *Experimental Brain Research 7*, pp. 158–168 (1969).

Engel, B.T. and Talan, M.I., "Cardiovascular Responses as Behavior," *Circulation –Supplement II*, pp. II–9 –II–13 (1991).

Weissler, A.M. et al., "Bedside Technics for the Evaluation of Ventricular Function in Man," *The American Journal of Cardiology*, vol. 23, pp. 577–583 (Apr. 1969).

Fawcett, A.J. and Nicolson, R.I., "Performance of Dyslexic Children on Cerebellar and Cognitive Tests," *Journal of Motor Behavior*, vol. 31, No. 1, pp. 68–78 (1999).

Fawcett, A.J. and Nicolson, R.I., "Persistent Deficits in Motor Skill of Children With Dyslexia," *Journal of Motor Behavior*, vol. 27, No. 3, pp. 235–240 (1995).

Fawcett, A.J. et al., "Impaired Performance of Children with Dyslexia on a Range of Cerebellar Tasks," *Annals of Dyslexia*, vol. 46, The Orton Dyslexia Society, pp. 259–283 (1996).

Hoyt, D.F. and Taylor, C.R., "Gait and the energetic of locomotion in horses," *Nature*, vol. 292, Macmillan Journals Ltd., pp. 239–240 (Jul. 16, 1981).

Ito, M., "A New Physiological Concept on Cerebellum," *Revenue Neurologique (Paris) 146*, Masson, Paris, pp. 564–569 (1990).

Ito, M., *The Cerebellum and Neural Control*, Raven Press, Entire book submitted (1984).

Jenkins, I.H. et al., "Motor Sequence Learning: A Study with Positron Emission Tomography," *The Journal of Neuroscience 14(6)*, Society for Neuroscience, pp. 3775 3790 (Jun. 1994).

Kelso, J.A.S. et al., "Dynamics Governs Switching Among Patterns of Coordination in Biological Movement," *Physics Letters A*, vol. 134, No. 1, pp. 8–12 (Dec. 12, 1988).

Krupa, D.J. et al., "Localization of a Memory Trace in the Mammalian Brain," *Science*, vol. 260, pp. 989–991 (May 14, 1993).

Milner, D.A. and Goodale, M.A., *The Visual Brain in Action*, Oxford University Press, Entire book submitted (1995).

Nicolson, R.I. and Fawcett, A.J., "Dyslexia is More than a Phonological Disability," *Dyslexia*, vol. 1, John Wiley & Sons, Ltd., pp. 19–36 (1995).

Nicolson, R.I. et al., "Time estimation deficits in developmental dyslexia: evidence of cerebellar involvement," *Proceedings of the Royal Society London B 259*, The Royal Society, pp. 43–47 (1995).

Portwood, M., *Developmental Dyspraxia –Identification and Intervention: A Manual for Parents and Professionals*, Second Edition, David Fulton Publishers Ltd., Entire book submitted (1999).

Portwood, M., *Understanding Developmental Dyspraxia: A Textbook for Students and Professionals*, David Fulton Publishers Ltd., Entire book submitted (2000).

Sandman, C.A., "Augmentation of the Auditory Event Related Potentials of the Brain During Diastole," *International Journal of Psychophysiology 2*, Elsevier, pp. 111–119 (1984).

Sandman, C.A., "Circulation as consciousness," *The Behavioral and Brain Sciences 9:2*, pp. 302–303 (1986).

Weissler, A.M. et al., "Systolic Time Intervals in Heart Failure in Man," *Circulation*, vol. XXXVII, No. 2, The American Heart Association, pp. 149–159 (Feb. 1968).

Scholz, J.P. and Kelso, J.A.S., "Intentional Switching Between Patterns of Bimanual Coordination Depends on the Intrinsic Dynamics of the Patterns," *Journal of Motor Behavior*, vol. 22, No. 1, pp. 98–124 (1990).

Schöner, G. and Kelso, A.S., "A Dynamic Pattern Theory of Behavioral Change," *Journal of Theoretical Biology 135*, Academic Press Ltd., pp. 501–524 (1988).

Stein, J.F. and Glickstein, M., "Role of the Cerebellum in Visual Guidance of Movement," *Physiological Reviews*, vol. 72, No. 4, The American Physiological Society, pp. 967–1018 (1992).

Stein, J. and Talcott, J., "Impaired Neuronal Timing in Developmental Dyslexia–The Magnocellular Hypothesis," *Dyslexia 5*, John Wiley & Sons, Ltd., pp. 59–77 (1999).

Tuller, B. and Kelso, J.A.S., "Environmentally–specified patterns of movement coordination in normal and split–brain subjects," *Experimental Brain Research 75*, Springer–Verlag, pp. 306–316 (1989).

Copy of International Search Report issued May 16, 2003, Appln. No. PCT/IB/02/05450, 6 pages.

\* cited by examiner

| | Group Classification | Main Feature | Examples | Quantity of group members | Particular features for randomization | | | Global number of random changes |
|---|---|---|---|---|---|---|---|---|
| | | | | | Type/Example | Partials | Total Options | |
| VISUAL TYPE | I | Two dimensional geometric forms | □ △ | 12 | Line structure<br>Line thickness | 4<br>2 | 8 | 10368 |
| | II | Three dimensional geometric forms | | 12 | | | | 1296 |
| | III | Letters | a, b, c...y, z | 26 | Fonts<br>A third dimension | 3<br>2 | 6 | 16848 |
| | IV | Capital letters | A, B......Z | 26 | Fonts<br>A third dimension | 3<br>2 | 6 | 16848 |
| | V | Numbers | 0, 1, 2.....9 | 10 | A third dimension | 2 | 2 | 2160 |
| | VI | Objects | | 10 | | | | 1080 |
| | VII | Puppets | | 5 | | | | 540 |
| | VIII | Flowers | | 10 | | | | 1080 |
| | IX | Living organisms | | 10 | | | | 1080 |
| | | | | | TOTAL FOR RANDOM VISUAL CHANGES | | | 51300 |
| Aural Type | I | Vowels | a, e, i, o, u | 5 | | | | 45 |
| | II | Two vowel phonema | Ei, ai...ou | 20 | | | | 180 |
| | III | Commands | Now, yes | 5 | | | | 45 |
| | | | | | TOTAL FOR RANDOM AURAL CHANGES | | | 270 |
| General Random Features | VISUAL TYPE | 12 colors; 3 brightness levels; 3 sizes; | | | TOTAL NUMBER FOR RANDOM CHANGES | | | 108 |
| | AURAL TYPE | 3 pitch levels; 3 volume levels | | | TOTAL NUMBER FOR RANDOM CHANGES | | | 9 |

FIG. 6

Main Subcycles of the Heart Cycle

APPARATUS, METHOD AND COMPUTER PROGRAM PRODUCT TO PRODUCE OR DIRECT MOVEMENTS IN SYNERGIC TIMED CORRELATION WITH PHYSIOLOGICAL ACTIVITY

BACKGROUND OF THE INVENTION

1. Field of the Invention

The present invention relates, generally, to addressing the need of promoting or improving bio-motoric performance in some human activities. More particularly, the present invention relates to addressing a possible subject's need to improve the level of synergic cooperation between one or more of his/her body parts with visceral cyclical function, during the execution or realization of an activity. More specifically, from the many possible embodiments of the invention, the possible usefulness of some of these embodiments for the treatment of many human conditions including learning disabilities in general and dyslexia in particular could be explored.

2. Related Art

At present, the characterization of mental life is dictated by a machine metaphor where the brain is viewed by many as a sophisticated computer whose software is the mind. Cognitive psychology views the mind as a grand software which manipulates representations from the environment as symbols.

This "computational" approach dominates today's mainstream in understanding the brain-mind set. Under this approach, the rest of the body simply executes and follows the programs stored in the brain (hardware), which is functionally manipulated by the mind (software). Furthermore, movements and voluntary actions are understood as 'motor programs' stored in the brain.

It is easy to see why the computer metaphor has predominated the field of motor control and movement coordination for years. Actions must be precisely ordered spatially and temporally, that is, a central motor program elicits instructions to choose the correct muscles, and then to contract and relax them at the right time. In short, the machine metaphor sees the brain as a central programmer and the body as a mere slave.

All the above theories, although fruitful in some areas, don't say much about the nature of movement coordination and its over all organization. All of us know, in a way, what coordination is, but little is known about how or why it is the way it is.

Getting down to specifics, movement coordination and organization is not a simple task since the human body is a complex system roughly comprising $10^2$ joints, $10^3$ muscles, $10^3$ cell types, and $10^{14}$ neurons and neuronal connections. In addition, the human body is multifunctional and behaviorally complex. For example, we can chew and talk at the same time by using the same set of anatomical components. All the above suggests the enormous potential of the human body for movement production and voluntary action. Nevertheless, how can it be that complex motor behavior organizes and coordinates itself as to produce a simple movement? Or, phrasing it in the language of dynamical systems, how can a high-dimensional system (degrees of freedom of the motor system) be almost infinitely compressed as to produce a low dimensional dynamic?

This issue is not trivial what so ever, since a breakdown in movement coordination and its overall organization is an indicator of several brain disorders such as Parkinson's disease, Huntington's chorea, etc. In the field of learning difficulties, a breakdown in movement coordination correlates with an impairment of cognitive perceptual tasking in people considered normal, leading to a spectrum of learning deficits such as: Dyspraxia, ADD, ADHD, Dyslexia, etc.

The scenery in the physiology field changed radically when the eminent Soviet physiologist Nikolai A. Bernstein (1896–1966) proposed an early solution to these problems (See, Bernstein, N. A., "The Coordination and Regulation of Movements," Pergamon Press, Oxford, 1967). Bernstein showed that human movements are so intrinsically variable and posses such an unlimited degree of freedom, that finding a single formula explaining movement behavior from efferent impulses alone is inevitably doomed to failure.

In Bernstein's own words "it is a most important fact that the invariant motor task is fulfilled not by a constant, fixed set, but by a varying set of movements, which lead to the constant, invariant effect" and this applies to simple and complex behavior alike. Motor variability according to Bernstein is not accidental, but essential, for the normal course of an active movement and for its successful accomplishment.

Bernstein's great insight was that of defining the problem of coordinated action as a complication in mastering the many redundant degrees of freedom in a movement; that is, of reducing to a minimum the number of independent variables to control. How do we take a multivariable system and control it with just one or few parameters?

Bernstein proposed to solve the above problem by treating each individual variable in the chain of producing a movement as if organized into larger groupings called linkages or "synergies".

Bernstein's hypothesis on motor coordination was not mechanistic or hard-wired (brain as hard-ware) anatomical units; rather, synergies were proposed to be functional units, flexibly and temporally assembled in a task-specific fashion.

Since Bernstein's contribution to motor control, the concept conveyed in the term "synergy" has been further developed by Hermann Haken in the late sixties in the specific area of "Synergetics", a branch of physics dealing with dynamical systems (non-linear phenomena). Synergetics describes an entire interdisciplinary field, (e.g., laser, chemical reactions, and fluid dynamics) dealing with pattern-formation spontaneously (self-organization) arising from cooperative phenomena that are far from equilibrium.

The key point in here is that the field of synergetics provides the theoretical and mathematical basis for establishing neuromotor organization through which coordinative modes (the pattern formation of movement) spontaneously arise, stabilize and change.

Perceptual motor coordination is today being considered as a window into biological and behavioral self-organization, thanks to the work and original experiments of Scott Kelso, in rhythmical behavior (bimanual phase transition paradigm). Kelso shed light on Bernstein's claims on movement variability as being the basis for the self-organization of simple and complex motor coordination alike, and in Kelso's own words: The fact that humans can stably produce, without a lot of learning, only two simple coordination patterns between the hands (parallel and anti-parallel finger movements) remains for me an absolute amazing fact. A complex system of muscles, tendons, and joints interacting with a much more complex system composed of literally billons of neurons appears to behave like a pair of couple oscillators. A truly synergic effect!' Kelso further reports that these patterns of motor coordination are far from being accidental, 'even skilled musicians and people who have had the two halves of their brain surgically separated to control epileptic seizures are still strongly attracted to these two basic patterns' (See, Tuller, B. & Kelso, J. A. S., "Environmentally Specified Patterns of Movement Coordination in Normal and Split-Brain Subjects," Experimental Brain Research, vol. 74, 1989).

The point that Kelso is making in here is that biological systems have an acuity for coordinating movement in particular timing patterns. (The present invention extensively modifies and deviates from the idea of synergy as described by Bernstein and Kelso.)

In the self-organized motoric pattern dynamics, cognitive intentionality is viewed as an integral part of the overall orchestration of the organism, that is, the organism's motor-intention potential is constrained by the organism's existing visceral organization. Such visceral-cognitive close relationship is not philosophical, but much to the contrary, recent studies in goal directedness suggest that there is brain activity prior to any overt movement.

A neuroanatomical structure in the brain, the 'SMA', determines the right moment to start the voluntary act as well as the sub cortical structures such as the cerebellum and basal ganglia (See, Deecke, L. et al., "Distribution of Readiness Potential, Premotion Positivity and Motor Potential of the Human Cerebral Cortex Preceding Voluntary Finger Movements," Experimental Brain Research, vol. 7, pp. 158–168, 1969; and Allen G. and Tsukahara, N. "Cerebro-cerebellar Communication Systems," Physiological Reviews, vol. 54, pp. 957–1006, 1974).

Furthermore, intending the switching of motor activity from a less stable to a more stable pattern should be easier and quicker than the vice versa. Apparently, voluntary acts (intention) can change the dynamical stability of motor patterns. Indeed, experimental results have confirmed the latter (See, Kelso, J. A. S. et al. "Dynamics Governs Switching Among Patterns of Coordination in Biological Movement," Physics Letters, A, vol. 134, pp. 8–12, 1988; Scholz, J. P., & Kelso, J. A. S., "Intentional Switching Between Patterns of Bimanual Coordination is Dependent on the Intrinsic Dynamics of the Patterns," Journal of Motor Behavior, vol. 22, pp. 124–198, 1990, and Schoner G. & Kelso, J. A. S., "A dynamic Pattern Theory of Behavioral Change," Journal of Theoretical Biological, vol. 135, pp. 501–525, 1988). In short, planning and execution seem to be but two aspects of a single act.

Moreover, from inside the visceral habitat (brain & Autonomic Nervous System), neural activity antecedes the intended action (decision making). Moreover, they prepare physiological mechanisms in the organism (i.e. cardiovascular activity) well in advance, in order to ensure a successful execution of the intended motoric action (See, Bechara, A. et al., "Deciding Advantageously Before Knowing the Advantageous Strategy," Science, vol. 275, pp. 1293–1295, 1997); Collet, C. et al., "Autonomic Responses Correlate to Motor Anticipation, Behavioral ," Brain Research, vol. 63, pp. 71–79, 1994; Astley, C. et al, "Integrating Behavior and Cardiovascular Responses: The Code," American Physiological Society, 1991; and Engel B. et al., "Cardiovascular Responses as Behavior," Circulation, 83 [Suppl II]: II-9-II-13, 1991).

Furthermore, it has been found that electro-cortical activity (event related potentials) covary with cardiovascular activity indicating the existence of precise periods during the cardiac cycle when perceptions and the impact of stimulation are optimal (See, Walker, B. B & Sandman, C. A., "Physiological Response Patterns in Ulcer Patients: Phasic and Tonic Components of the Electrograstrogram," Psychophysiology, vol. 14, pp. 393–400, 1977; Sandman, C. A. et al., "Influence of Afferent Cardiovascular Feedback on Behavior and the Cortical Evoked Potential," Perspectives in Cardiovascular Sychophysiology, ed: J. T. Cacioppo & R. E. Petty, Guilford Press, 1982; Sandman, C. A., "Augmentation of the Auditory Even Related Potential of the Brain During Diastole," International Journal of Psychophysiology, vol. 2, pp. 111–119, 1984; and Sandman, C. A., "Circulation as Consciousness," The Behavioral and Brain Sciences, vol. 9:2, 1986).

Yet, another and most crucial fact is the synergic correlation existing between locomotion patterns (movement patterns) in horses (and other quadrupeds as well as humans bipeds) and their respective physiological activity habitats, namely, if the horse is allowed to locomote free, the horse will select speeds, which show a minimum of oxygen consumption per unit distance traveled (See, Hoyt, D. F. and Taylor, C. R., "Gait and Energetics of Locomotion in Horses," Nature, vol. 292, pp. 239–240, 1981). Horses employ a restricted range of speeds in any given gait, that is, in locomotion (running) the horse uses a speed that corresponds to minimum energy expenditure.

Furthermore, horses and human bipeds when they move normally avoid potentially unstable regions; they select only a discrete set of speeds from a broad range available. In fact, just the ones that minimize energy. As in quadrupeds and human bipeds, the scope and teachings of this invention promote the implementation of synergic timed correlated movements, with physiological activity functions, as to reduce energy dissipation, or consequently, maximize metabolic efficiency during sensory motor performance.

Learning is commonly understood as the process of acquiring skill. It involves a change of behavior through practice or experiences, namely, the organism's ability to escape its limited built-in behavioral repertoire.

The process of learning has been found to be highly correlated with: (a) Normal ontological realization of self-organization in motor movement coordination, such as: limb movements, eye movements, articulation of vocal cords (speech), lips, tongue, jaw, facial movements, etc.; and (b) attainment of a normal postural balance and a propioceptive sense by the organism.

As substantiating point "a" and "b", there is an extensive literature in the field of learning difficulties/disabilities that directly links a poor early sensory-motor realization as being the basis or effective cause for a much later learning spectrum deficit in the child. Particularly, learning deficits such as Dyspraxia, ADD, ADHD and Dyslexia have been associated to the 'cerebellum'.

The cerebellum is involved in the control of independent limb movements and especially in rapid, skilled movements. Damage to different parts of the cerebellum can lead to different symptoms in humans, ranging from disturbances in posture and balance, to limb rigidity, loss of muscle tone, lack of co-ordination and impairment of rapid pre-planned, automatic movements.

Furthermore, evidence of the role-played by the cerebellum in learning and motor skills can be seen in Ito, M., "The Cerebellum and Neural Control," New York: Raven Press, 1984; Ito, M., "A New Physiological Concept on Cerebellum," Revue Neurologique, Paris, vol. 146, pp. 564–569; Jenkins, I. H. et al., "Motor Sequence Learning—A Study with Positron Emission Tomography,"

Journal of Neuroscience, vol. 14, pp. 3775–3790, 1994; and Krupa, D. J. et al., "Localization of Memory Trace in the Mammalian Brain," Science, vol. 260, pp. 989–991, 1993. In short, the role of the cerebellum in learning deficits has lead into the postulation of the 'Cerebellar Deficit Hypothesis' or CDH.

Generally speaking, the making of a direct link between deficits in motor-coordination and learning disabilities, brings us first to consider the developmental condition named 'Dyspraxia'. Dyspraxia can be defined as an impairment or immaturity in the organization of movement. Associated with this there may be problems of language, perception and thought. Developmental Dyspraxia is the term used to describe youngsters and adults who have coordination difficulties but who also, in the majority of cases, show significant perceptual problems. Developmental Dyspraxia affects between two to five per cent of the population with a ratio of four boys to one girl (See, Portwood, M., "Understanding Developmental Dyspraxia," London: David Fulton Publishers, 2000).

Furthermore, Dyspraxia is a developmental condition and the comorbidity with autistic spectrum disorders, Dyslexia, Attention Deficit and Hyperactivity Disorder is high. M. Portwood suggests that such comorbidity is probably between forty (40) percent and forty-five (45) percent (See, Portwood, M., "Developmental Dyspraxia—Identification and Intervention," London: David Fulton Publishers, 1999). Moreover, associated disorders with Deficit Coordination Disorders (DCD) may include delays in other non-motor milestones (See, Portwood, M 2000). Connected disorders may include Phonological Disorders, Expressive Language Disorder, and mixed Receptive Expressive Language Disorders. Prevalence of DCD has been estimated to be as high as six (6) percent for children in the age range of 5–11 years (See, Portwood, M. 1999 and 2000).

Turning now to the particular case where a lack in motor-organization impairs perception while reading, writing and spelling, brings us to focus in 'Dyslexia'. Dyslexia can be defined as a neuro-developmental disorder characterized by deficits at biological, cognitive and behavioral levels, localized mainly, but not only, in phonological and reading processes. For this complex syndrome, affecting around five (5) percent of the population, no practical and effective remediation has yet been found.

Dyslexia (which can be translated as "difficulty with words") is commonly understood as a childhood difficulty in the acquisition of reading, spelling and writing skills, basic literacy problems often extended into adulthood. Experimental research has revealed deficits in tasks that have no linguistic/phonological components. A common feature of these components is that they involve either the coordination of visual and motor component (hand-eye or eye movement coordination) or the combination of sequences of their movements or processes.

Regarding motor performance, dyslexics have shown to have difficulty with static and dynamic balance, manual dexterity, ball skills, gross and fine motor control and production of simultaneous movements. They may also show a deficit in the motor skills required in speed of tapping, head-toe placement and rapid successive finger opposition. It has been estimated that approximately fifty (50) percent of sampled dyslexics presented visual-motor deficits that could be long-term and hereditable.

In particular, sensory motor—balance related problems impairing learning, such as the ability to read (Dyslexia) have been recently intensively studied by A. J. Fawcett and R. I. Nicolson (See, Fawcett, A. J. and Nicolson, R. I., "Persistent Deficits in Motor Skill for Children with Dyslexia," Journal of Motor Behavior, vol. 27, pp. 235–240, 1995; Fawcett, A. J., et al., "Impaired Performance of Children with Dyslexia on a Range of Cerebellar Tasks," Annals of Dyslexia, vol. 46, pp. 259–283, 1996; and by Fawcett, A. J. and Nicolson, R. I., "Performance of Dyslexic Children on Cerebellar and Cognitive Tests," Journal of Motor Behavior, vol. 31, pp. 68–78, 1999). Their conclusion was that in Dyslexic children some of the most notable results were the exceptionally poor performance in postural stability, muscle tone, limb shake and overall weakness in complex voluntary movement execution.

Another active line of research basically linking impaired sensory motor coordination of the eye (the oculomotor system) and the cerebellum with the inability to read in dyslexic children, is related to the 'magnocellular system'. The magnocellular system consists of retinal ganglion cells (about 10%) that signal the timing of visual events, not their form. Hence they are important for detecting visual motion. The dorsal pathway is an output visual stream processing that passes via the middle temporal motion area to the posterior parietal cortex. It is dominated by magnocellular input. Since these signals provide information about the timing of visual events and of the motion of visual targets, the dorsal system is important for the guidance of both eye and limb movement (See, Milner, A. D. and Goodale, M. A., "The Visual Brain in Action," Oxford University Press, 1995). Via the cerebellum, the magnocellular system is crucial for controlling eye movement during reading, and particularly for the rapid motion feedback that prevents the eyes slipping off their fixation on a word (See, Stein J. F. and Glickstein M., "The Role of the Cerebellum in the Visual Guidance of Movement," Physiological Reviews, vol. 72, pp. 967–1018, 1992).

Yet another hypothesis underlying developmental dyslexia has to do with magnocellular neuronal abnormal development in the brain (See, Stein, J. F. and Talcott, J. B., "The Magnocellular Theory of Dyslexia," Dyslexia, vol. 5, pp. 59–78, 1999). This magnocellular hypothesis is based on evidence that dyslexics have lower sensitivity for transient stimuli either in the visual or in the auditory system. In other words, Dyslexic children show a lower sensitivity to 'temporal processing' of information. We can see that a lack of self-organization in sensory motor movements goes together with an impairment in the timing perception of stimuli, leading to confusion in signal discrimination.

SUMMARY OF THE INVENTION

According to the present invention, central to the synergetic approach to movements are: (1) relative timing information among motor components in the process of motor coordination; (2) the lack of an effective cause, program or code responsible for the emerging motor pattern; and (3) spontaneous pattern formation or "self organization" analogous in Bernstein's approach to the role played by movement coordination as the basis of the organization of the control of the motor apparatus.

This invention is directed towards reinforcing the structural-temporal coupling between movements and physiological components. More specifically, one main characteristic of the present invention is to provide technological means to: 1) time correlate movements with specific target organs and/or physiological systems within the viscera (e.g. heart, lungs, brain, hormonal, etc); 2) time-correlate the movements with a particular phase or phases within the target organ cycle (e.g. systolic, diastolic, inhalation, exhalation, and brain electrocortical waves) and/or physiological systems within the viscera; and 3) introduce a selective fluctuation (instability) in the time correlation within and without the (variable) temporal frame of the preselected phase(s) of the particular chosen target organ cycle and/or physiological system within the viscera. In this invention, more than one target organ and/or physiological system could participate in the correlation.

In fact, new scientific developments, as well as experimental research carried out mainly in the last seventy (70) years most of which not included in prior art, suggest that by means of the many forms in which this invention can be implemented, today's natural synergic levels of the human organism via movements in relative coordination with cyclical physiological activities may be increased, and therefore the triggering of self-organization among biological functions may have a higher probability of occurrence.

The general scope and aspect of the teachings of this invention are consistent with many findings in a number of inter-correlated fields, as previously and further on detailed. One objective of this invention consists in providing the means and methods aiming to optimize, for example, the performance of any kind of physical activity, active or passive, including current sports and practices of physical exercise, by way of promoting synergetic activity between movements and physiological cyclical activity (aided or not by machines) in the entire population, regardless of age, sex and health condition.

Another feature of the invention and based on the above data lies in its aim for the expedition of new skill acquisition, namely, learning, by establishing a synergically correlation among movements and physiological cyclical activity.

Another scope of the teachings and features of this invention is to provide many forms of research tools to investigate and develop new diagnostic and treatment for the broad spectrum of learning difficulties in normal and pathology population alike, where subjects will specially benefit from this novel invention. As discussed above, the root of learning deficits and its correlation to biomechanical problems, may be well compensated and in many cases overcome, by technologically inducing a kind of what can be denominated as self-movements aiming to trigger dormant and/or to promote new neuronal connections in the cerebellum, frontal lobes in the cortex and other zones of the neural network.

Moreover, research in many correlated fields, some of them only sketched above, gives us ground to hypothesize that movements in synergic timed correlation with physiological activity functions, may institute and reinforce neuronal over connectivity, which in turn may extend the phenomena of synergism among physiological functions.

BRIEF DESCRIPTION OF THE DRAWINGS/ FIGURES

The accompanying drawings, which are incorporated herein and form part of the specification, illustrate embodiments of the present invention and, together with the description, further serve to explain the principles of the invention and to enable a person skilled in the pertinent art to make and use the invention.

FIG. 6 illustrates an example table containing sensorial signals and stimuli for voluntary involvement of a subject in order to trigger the practice of correlated movements according to an embodiment of the invention.

Figure 13:
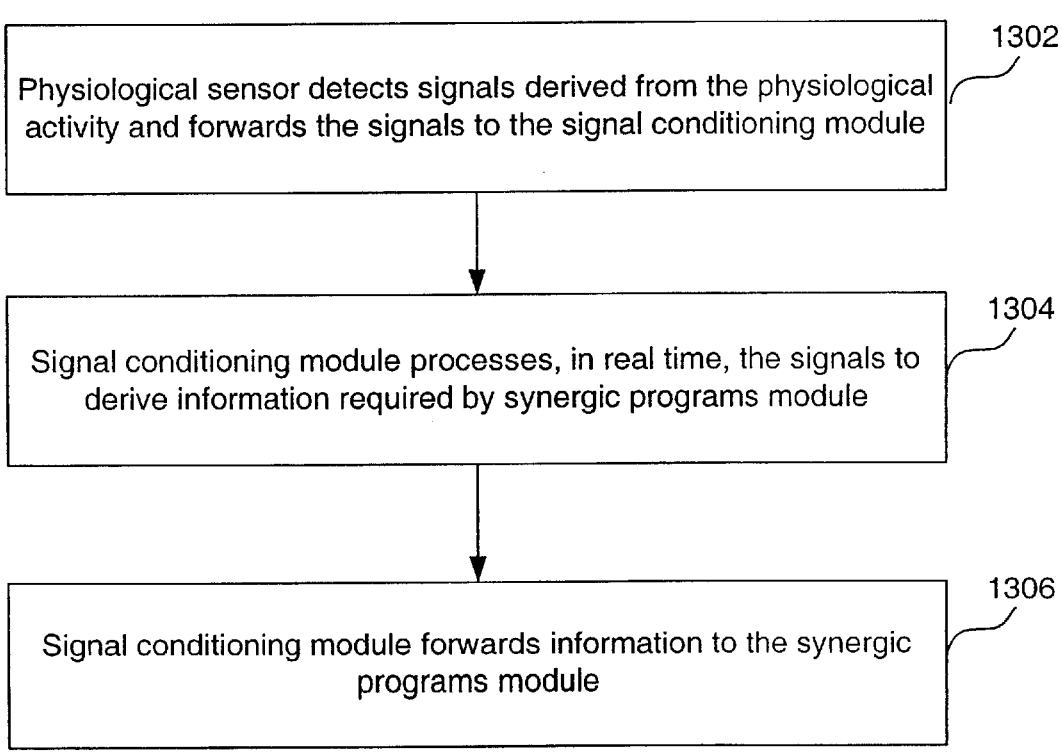

FIG. 13 describes in more detail the step of physiological activity sensor module monitoring a physiological activity of a subject according to an embodiment of the invention.

Figure 14:
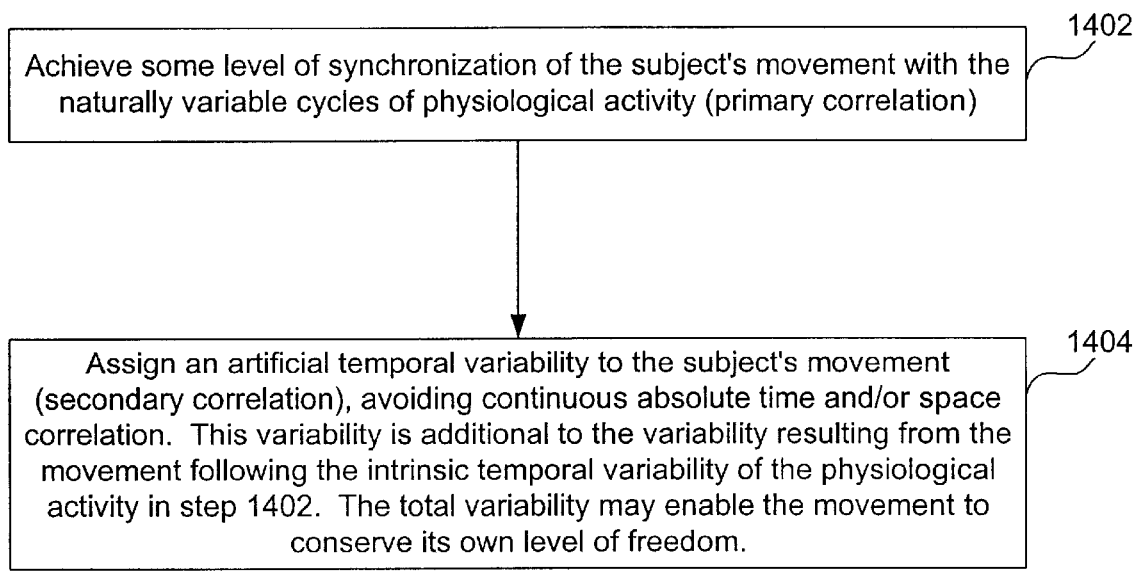

FIG. 14 is a flowchart illustrating the high level operation of an embodiment of the present invention to obtain synergic timed correlation of physiological activity and movements according to an embodiment of the invention.

Figure 15A:
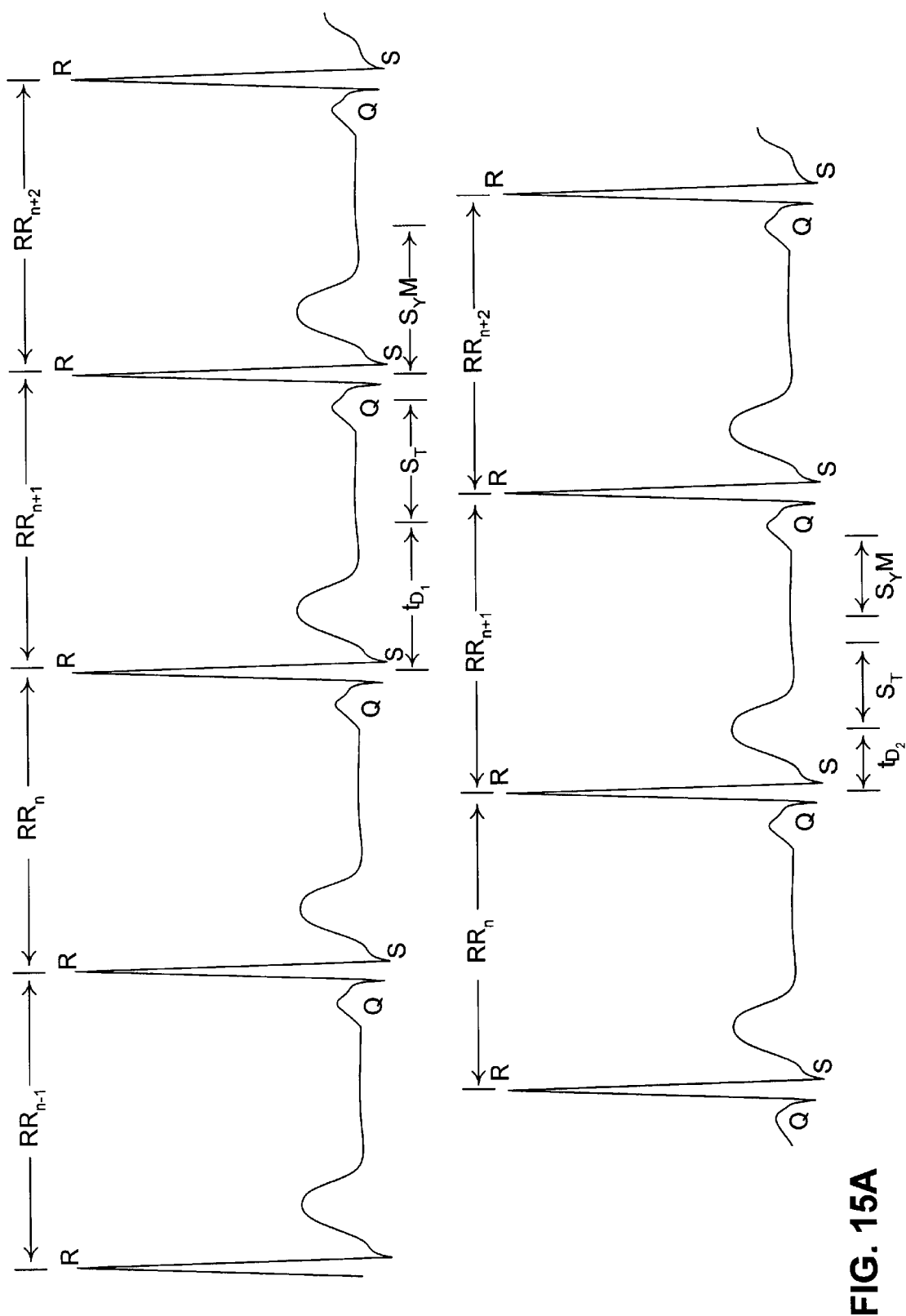
Figure 15B:
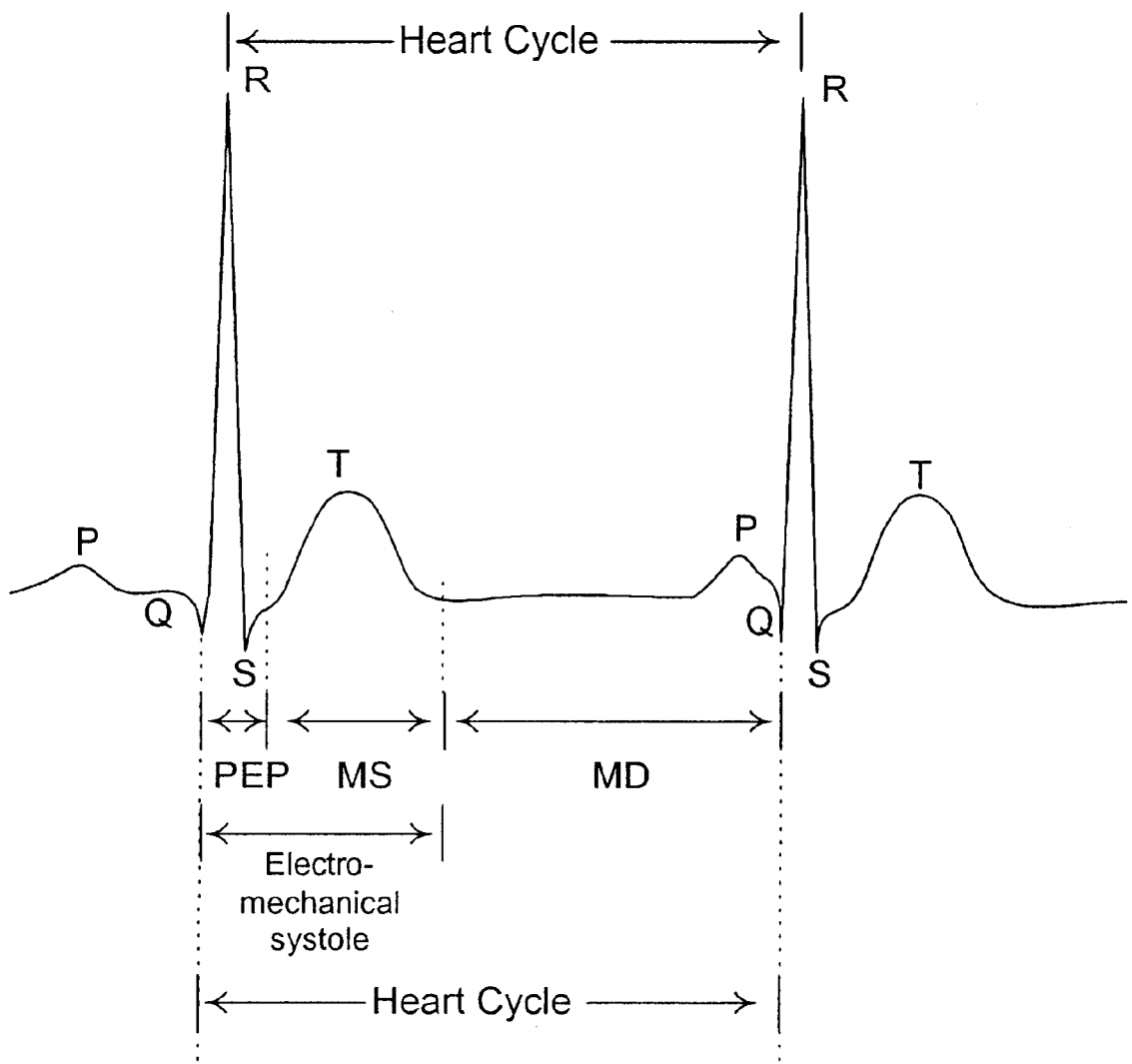

FIGS. 15A and 15B illustrate occurrences of heart cycles according to an embodiment of the invention.

Figure 16:
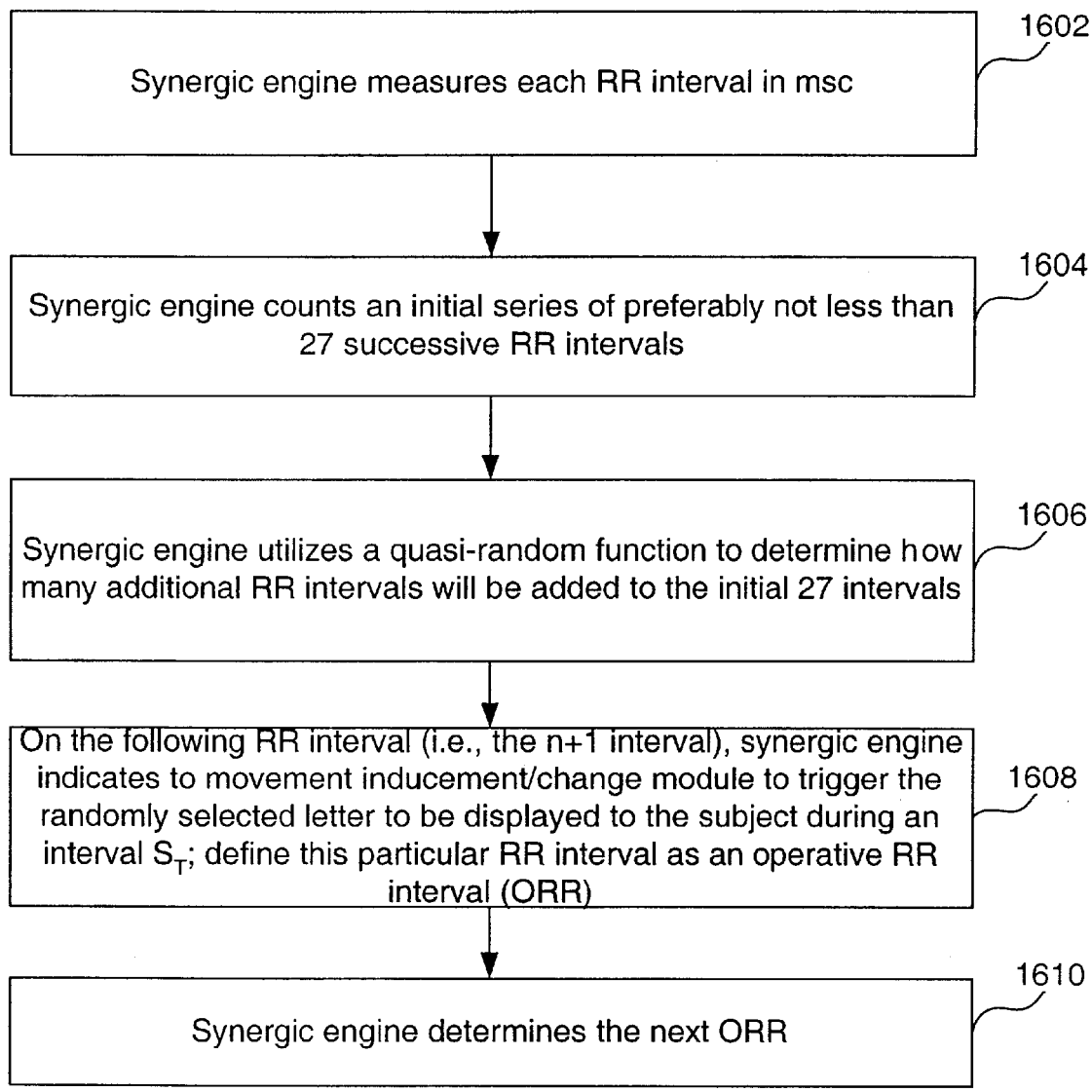

FIG. 16 illustrates the correlation of the subject's movement with heart cycle according to an embodiment of the invention.

Figure 17:
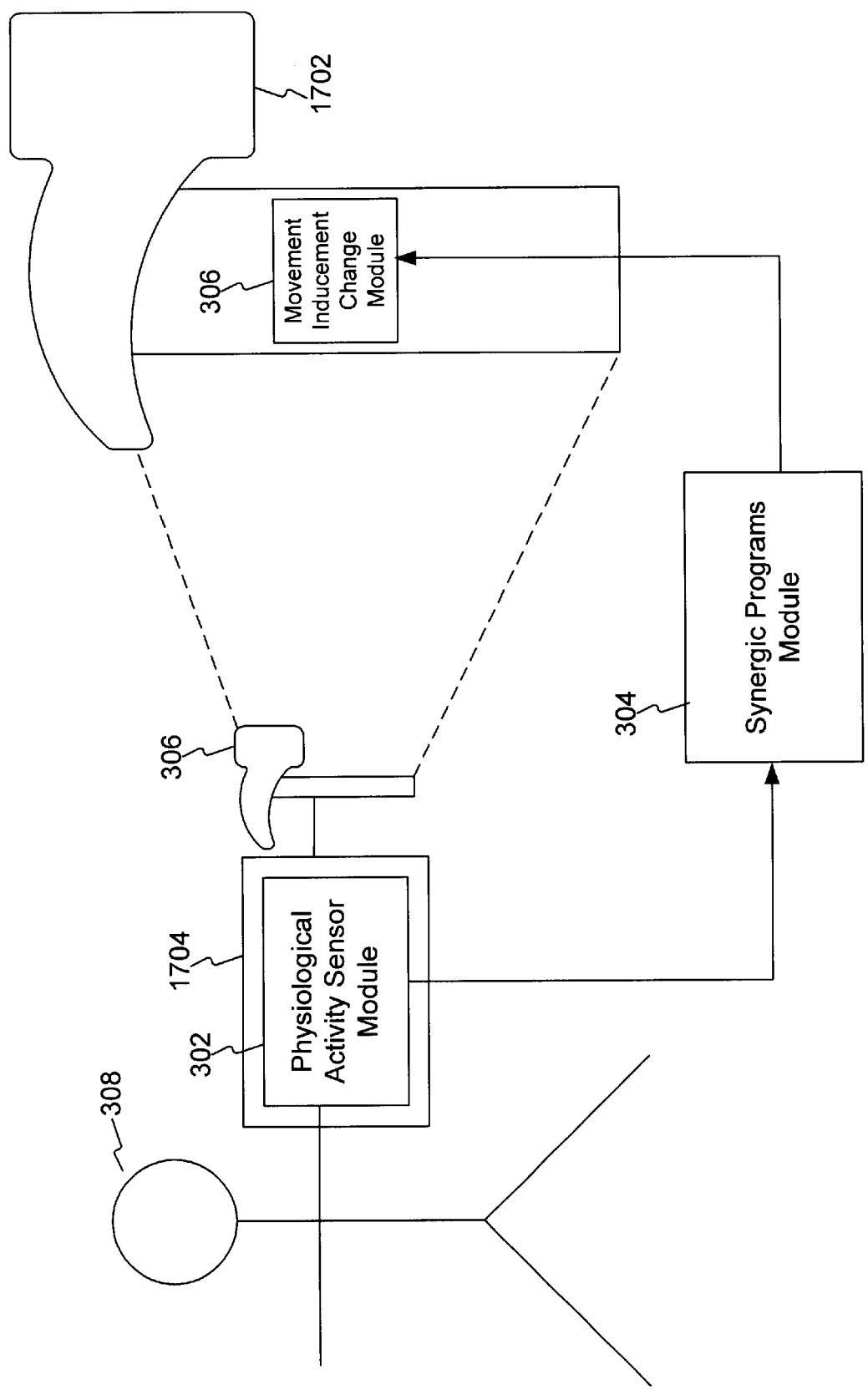

FIG. 17 illustrates an embodiment involving voluntary/active combination as implemented in a hammer according to an embodiment of the invention.

Figure 18:
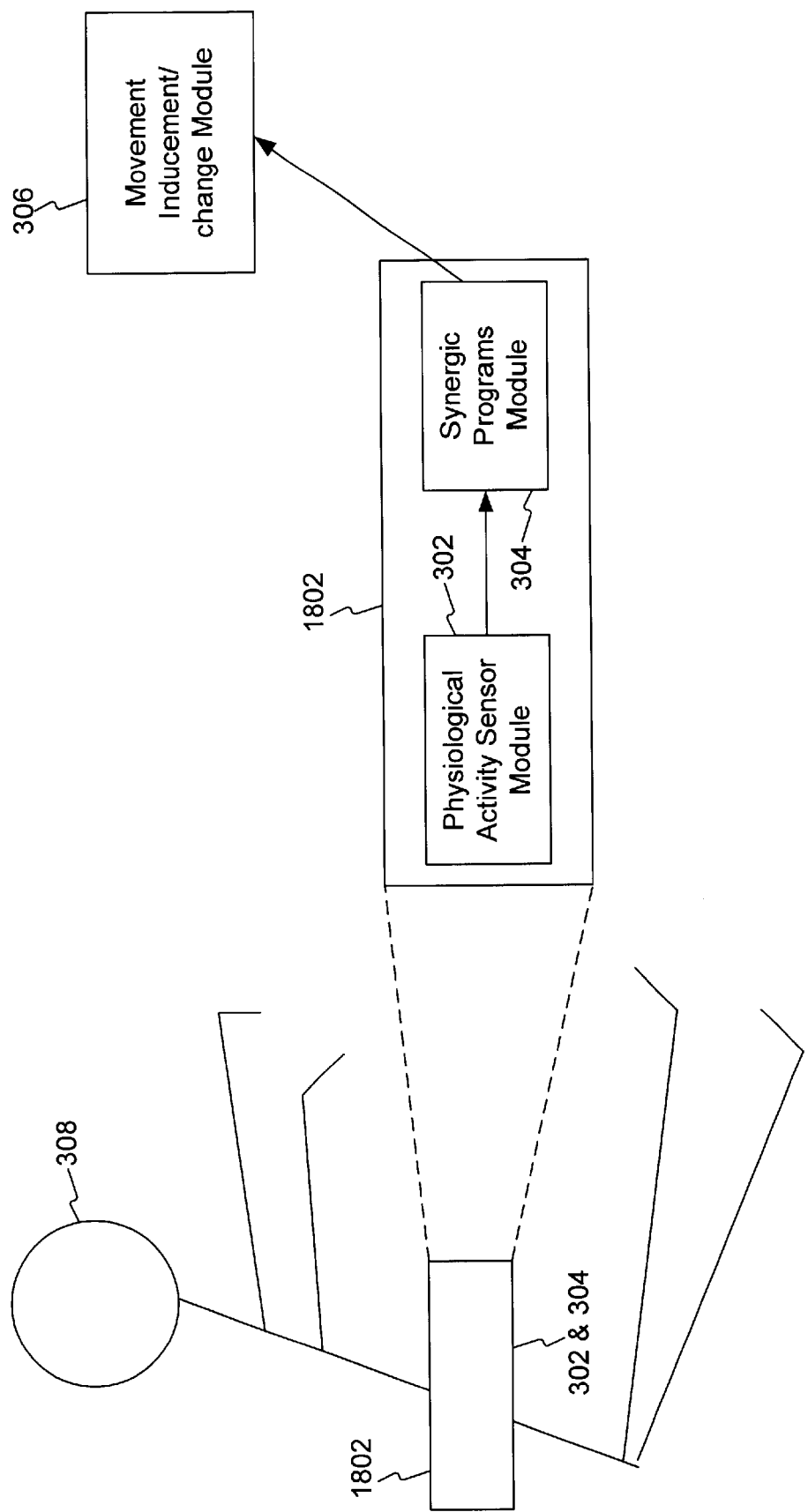

FIG. 18 illustrates an embodiment involving voluntary/active combination as implemented via stretching according to an embodiment of the invention.

Figure 19:
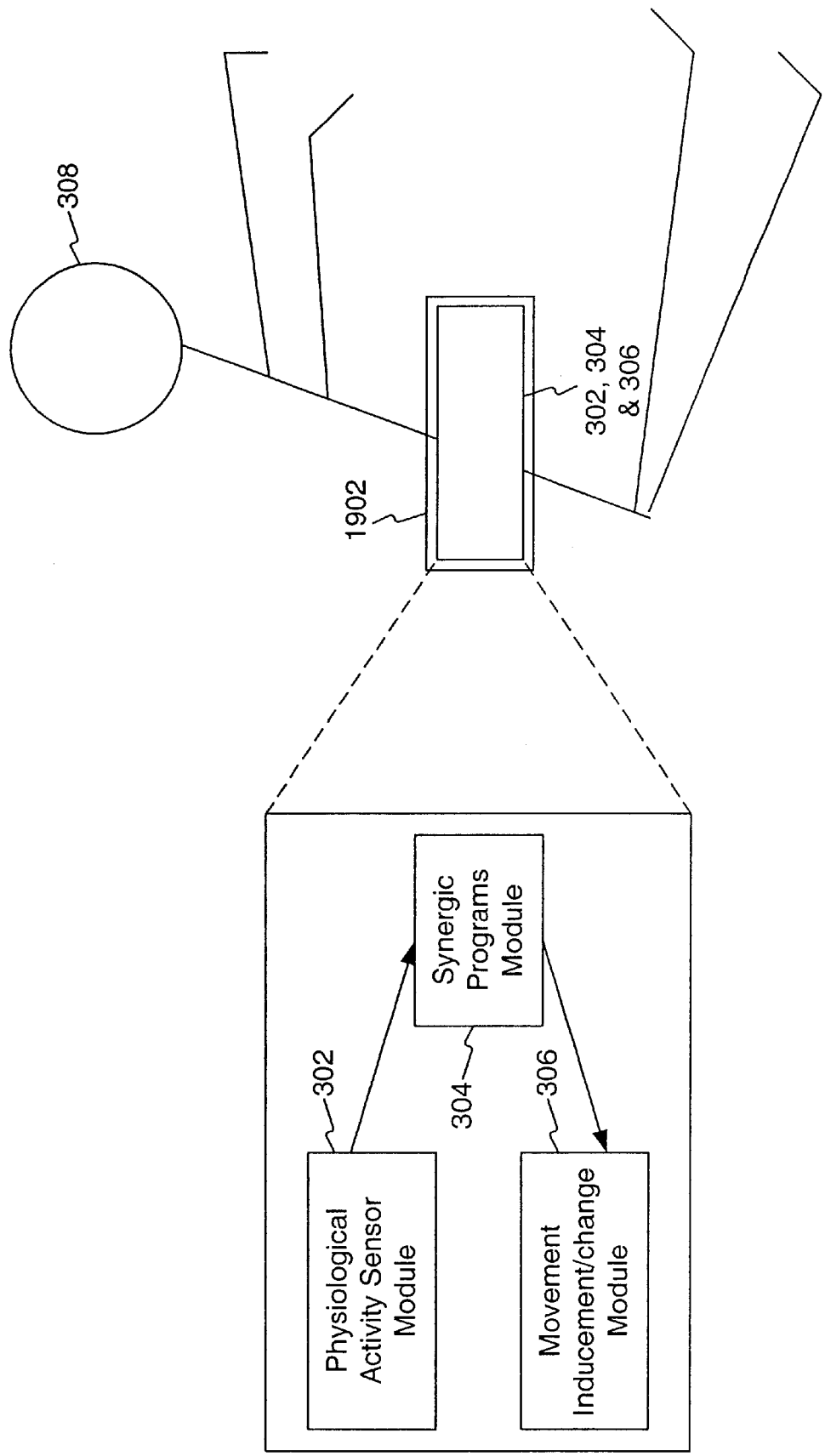

FIG. 19 illustrates an embodiment involving voluntary/active combination as implemented via stretching according to an embodiment of the invention.

Figure 20:
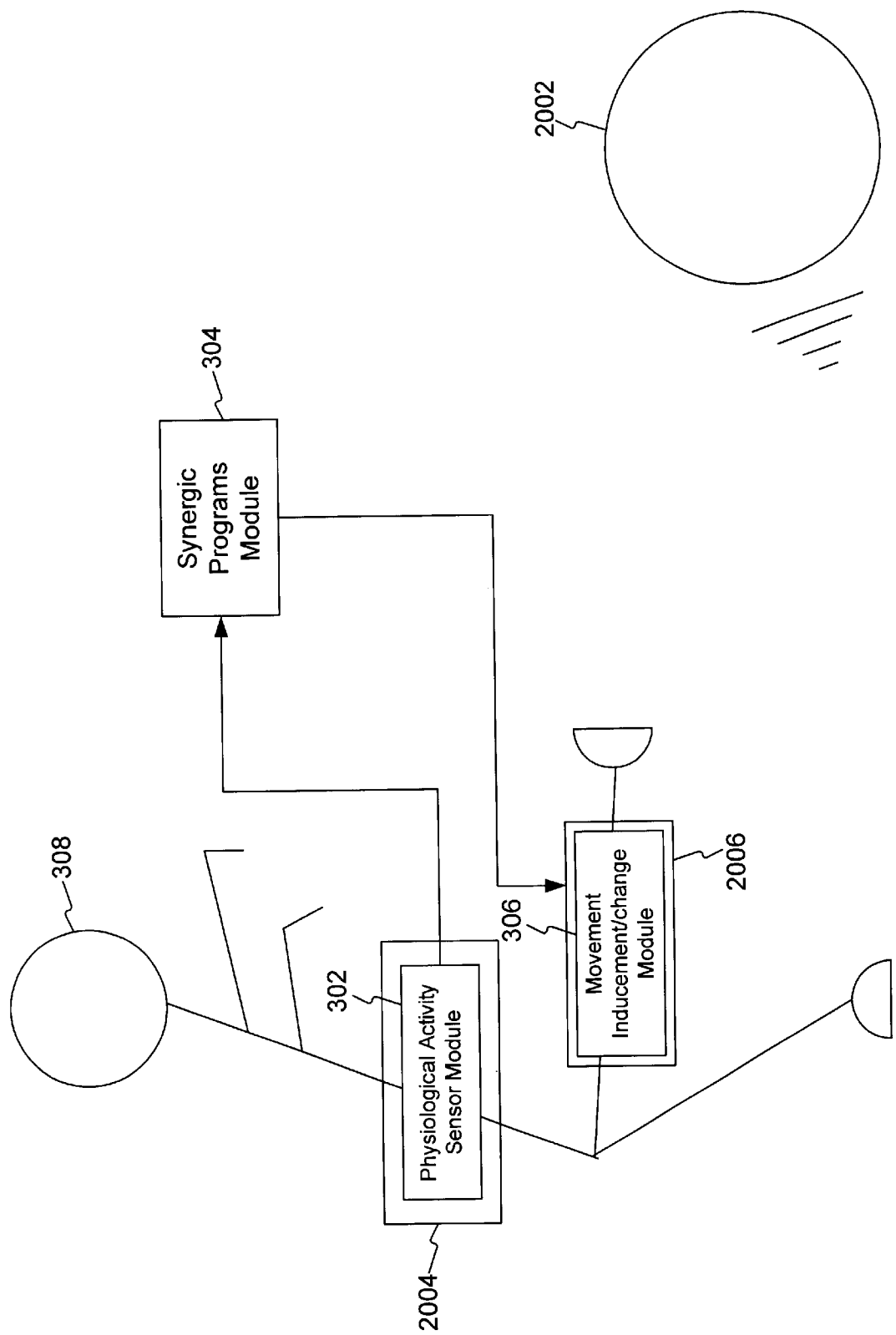

FIG. 20 illustrates an embodiment involving voluntary/active combination as implemented by kicking a ball according to an embodiment of the invention.

Figure 21:
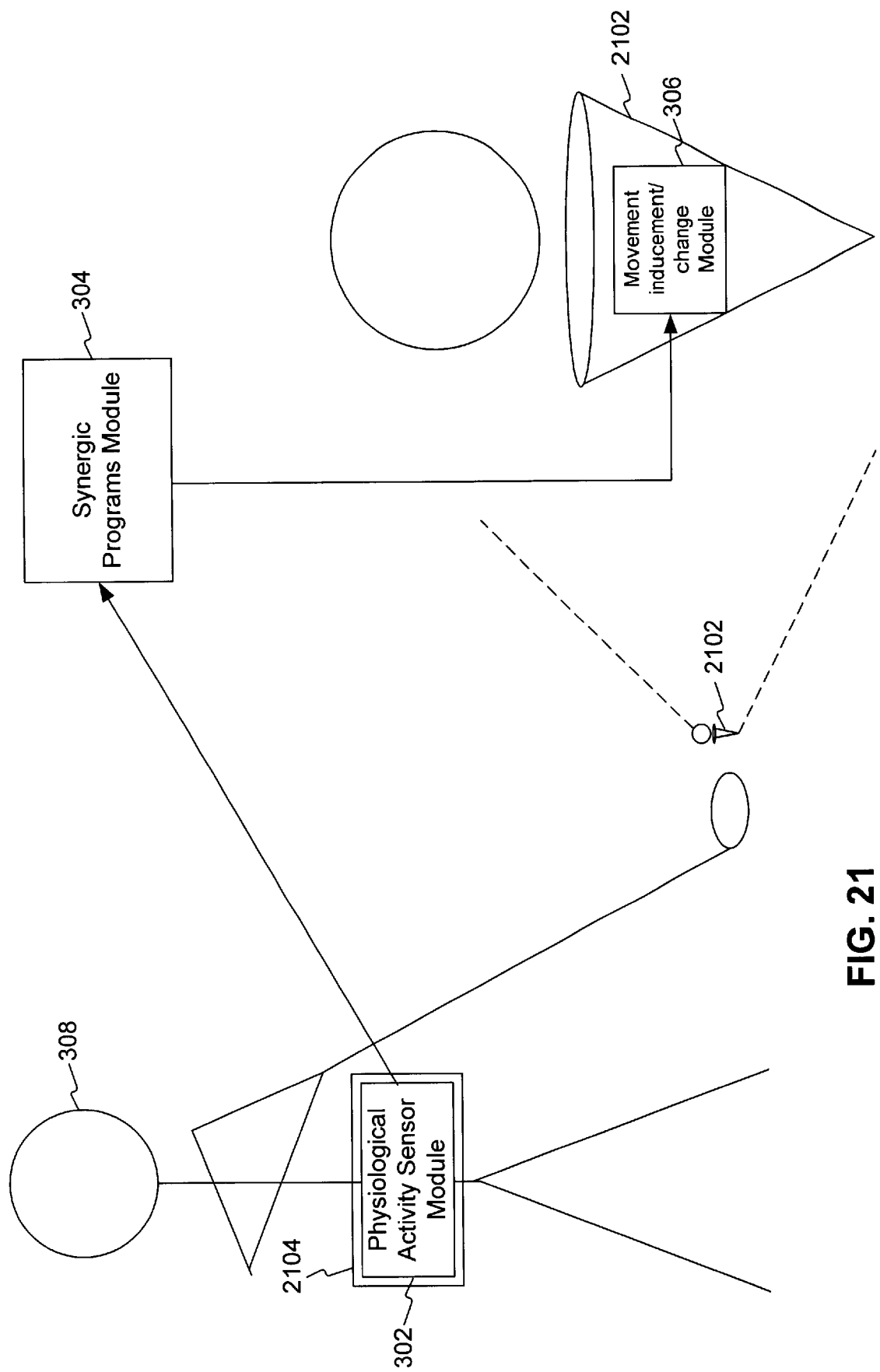

FIG. 21 illustrates an embodiment involving voluntary/active combination as implemented by swinging a golf club according to an embodiment of the invention.

Figure 22:
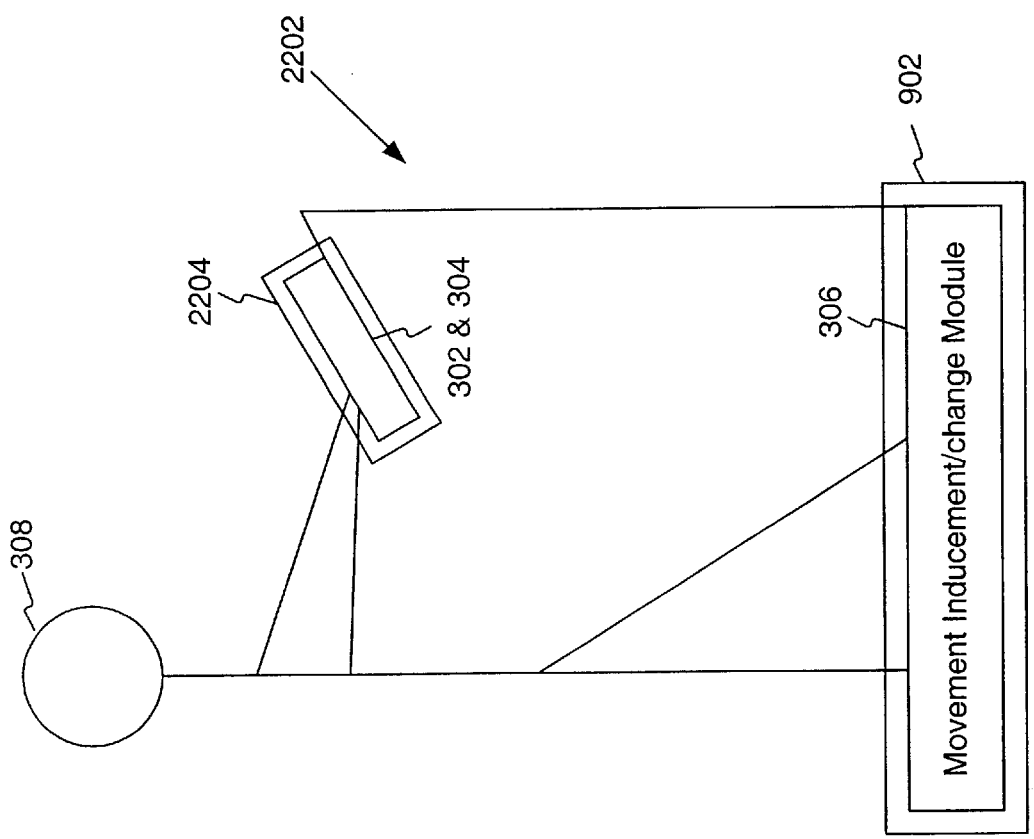

FIG. 22 illustrates an embodiment involving voluntary/reactive combination as implemented in a treadmill according to an embodiment of the invention.

Figure 23:
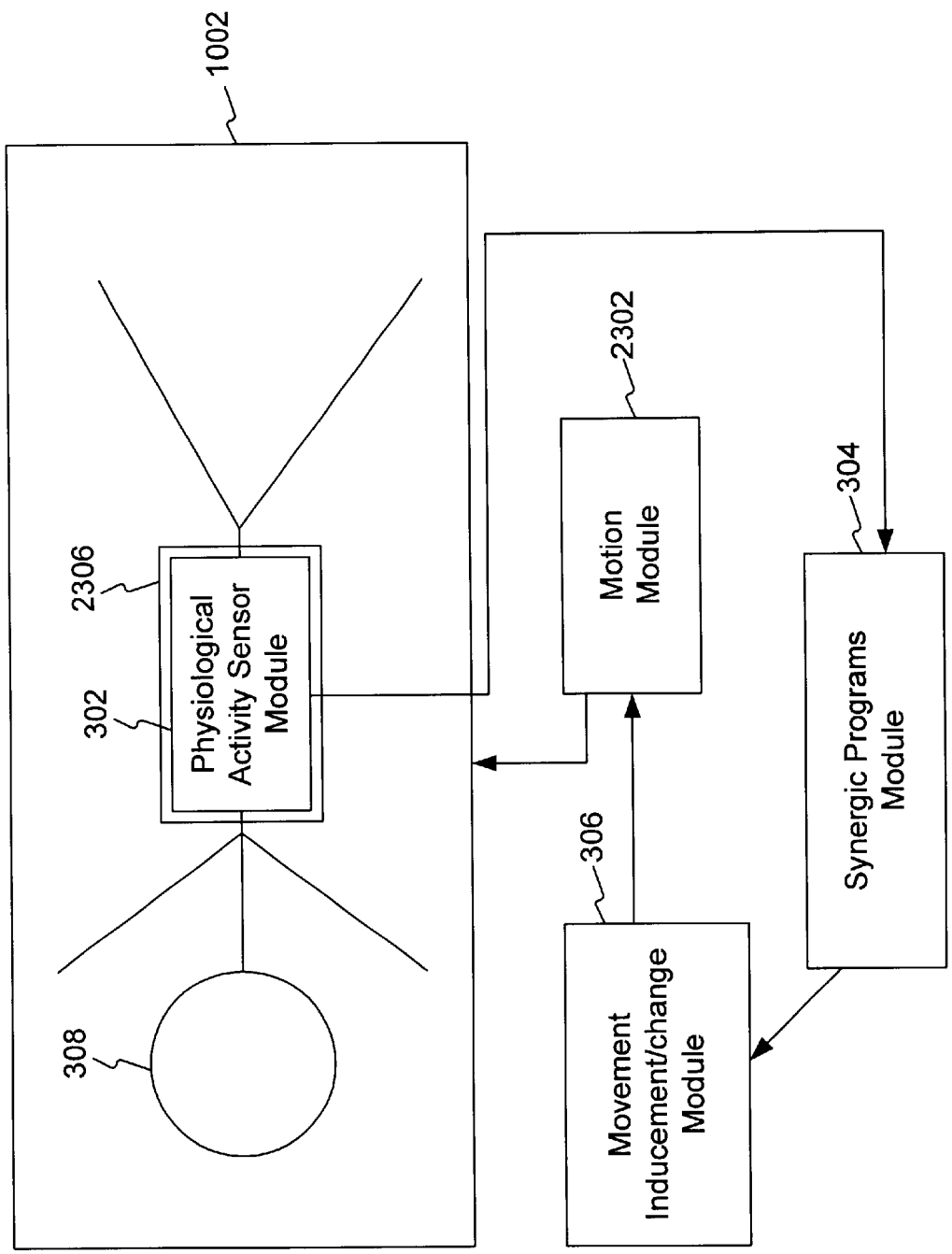

FIG. 23 illustrates an embodiment involving involuntary/passive combination as implemented in a bed according to an embodiment of the invention.

Figure 24:
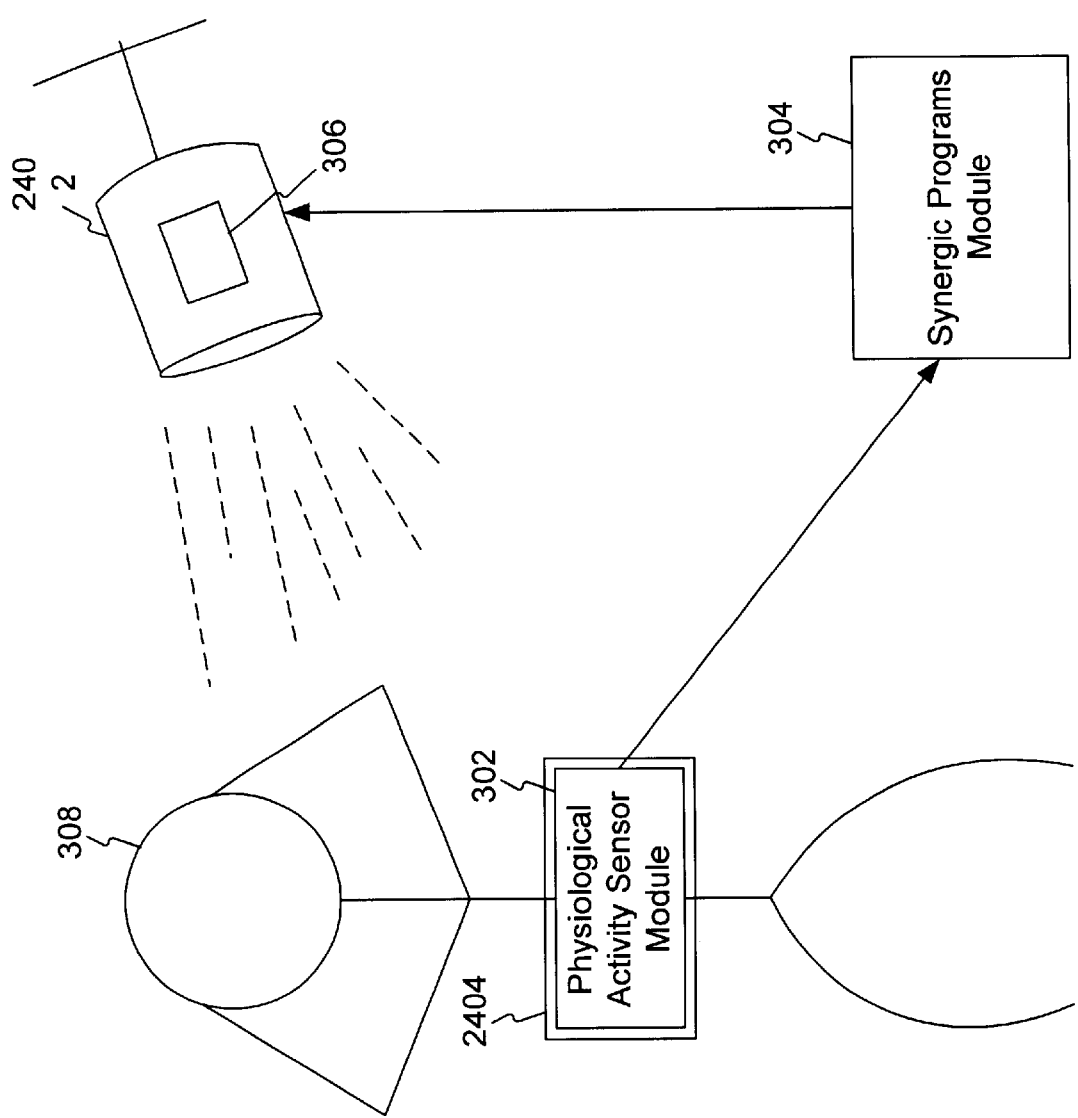

FIG. 24 illustrates an embodiment involving involuntary/reflexive combination as implemented in a shower head according to an embodiment of the invention.

Figure 25:
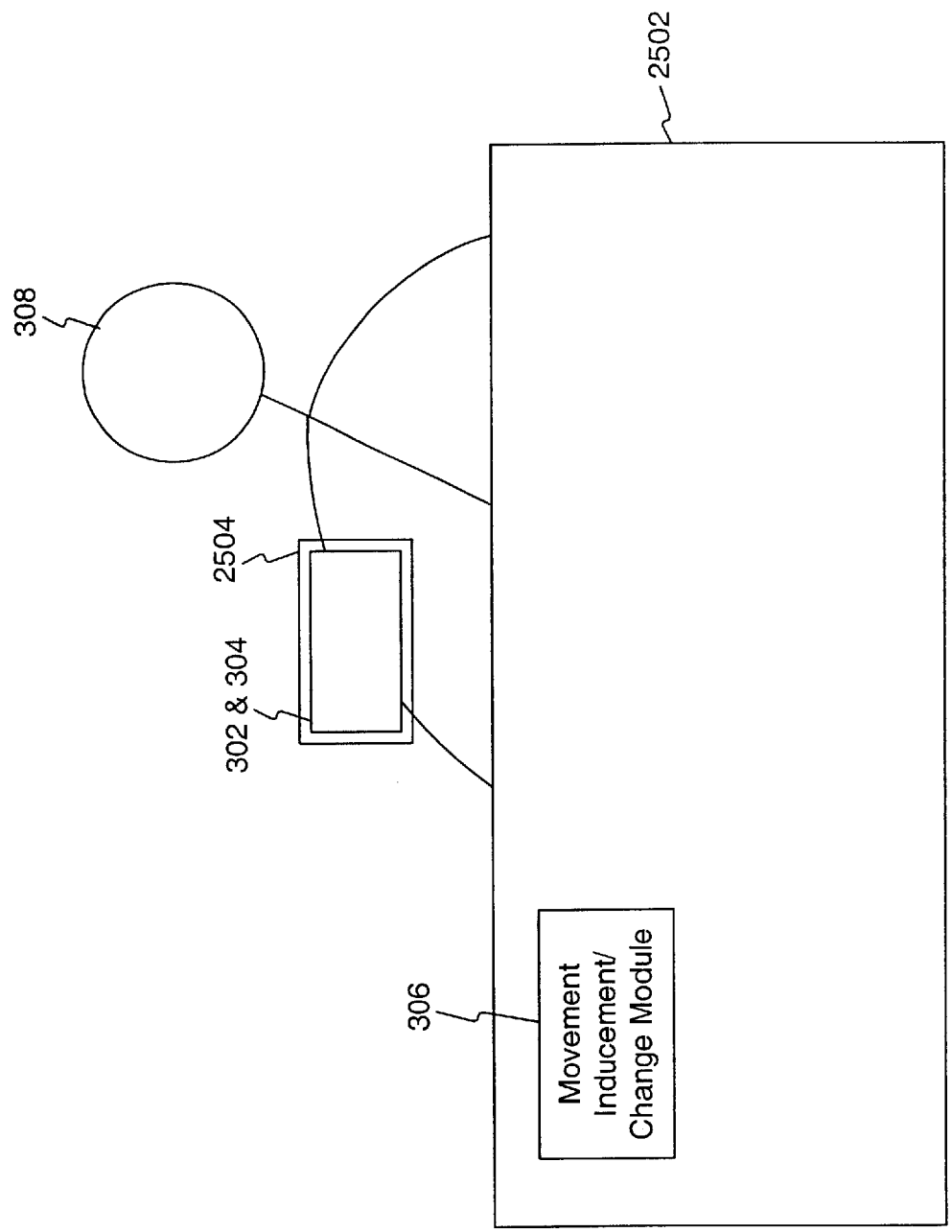

FIG. 25 illustrates an embodiment involving involuntary/reflexive combination as implemented in a hydrotherapy bath according to an embodiment of the invention.

Figure 26:
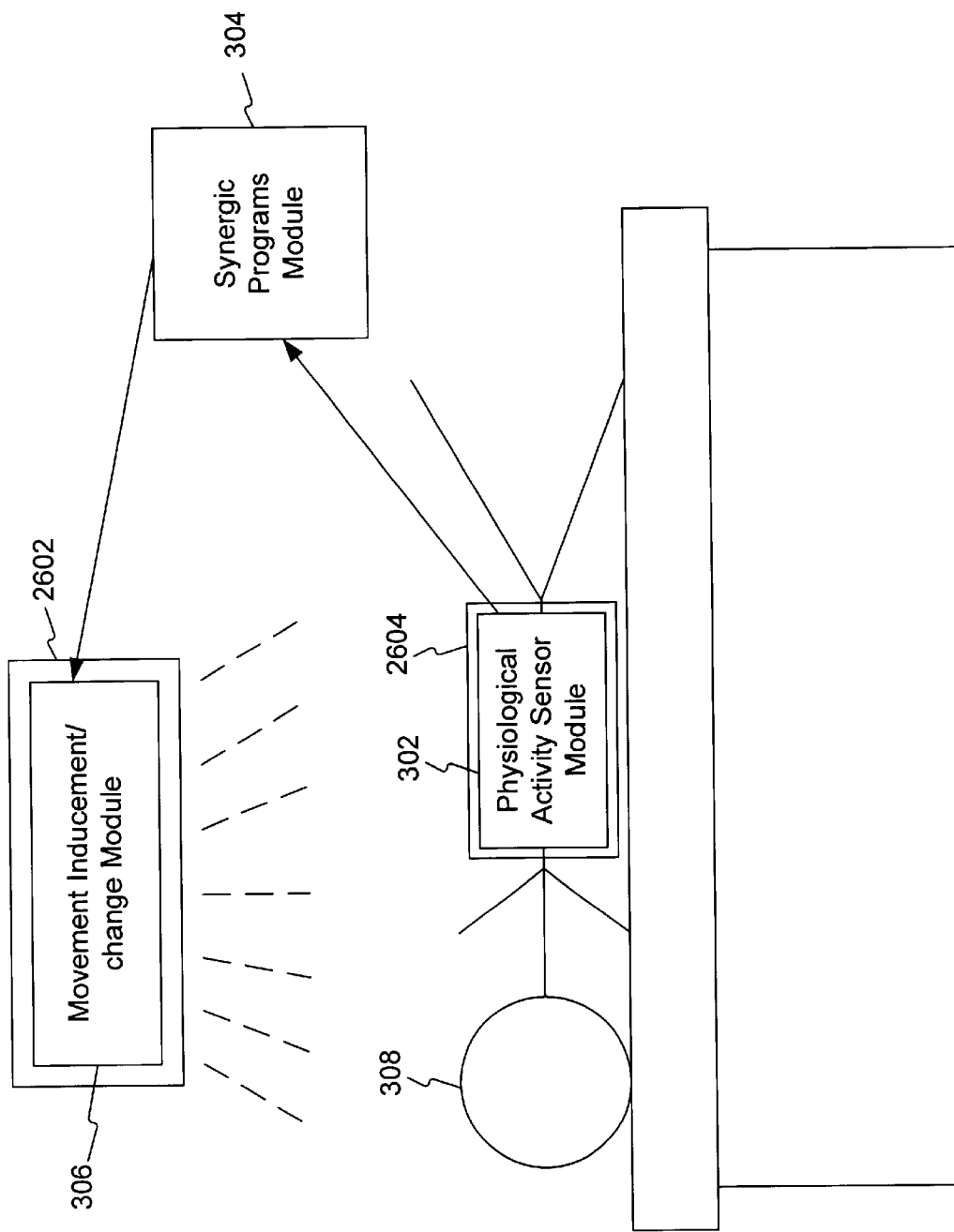

FIG. 26 illustrates an embodiment involving involuntary/reflexive combination as implemented by light that emits radiative energy according to an embodiment of the invention.

Figure 27:
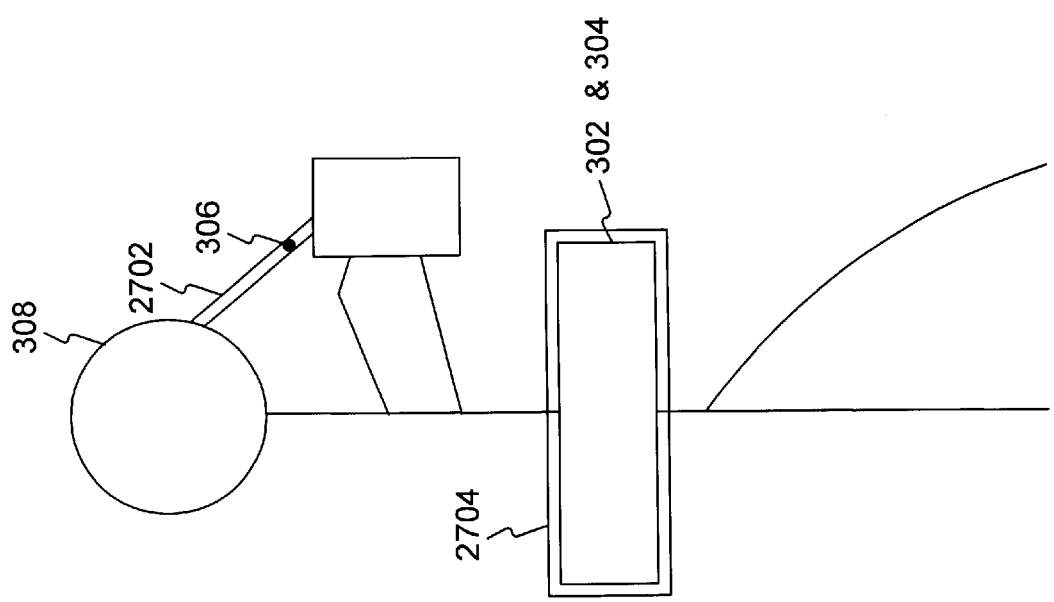

FIG. 27 illustrates an embodiment involving involuntary/reflexive combination as implemented via a straw according to an embodiment of the invention.

Figure 28:
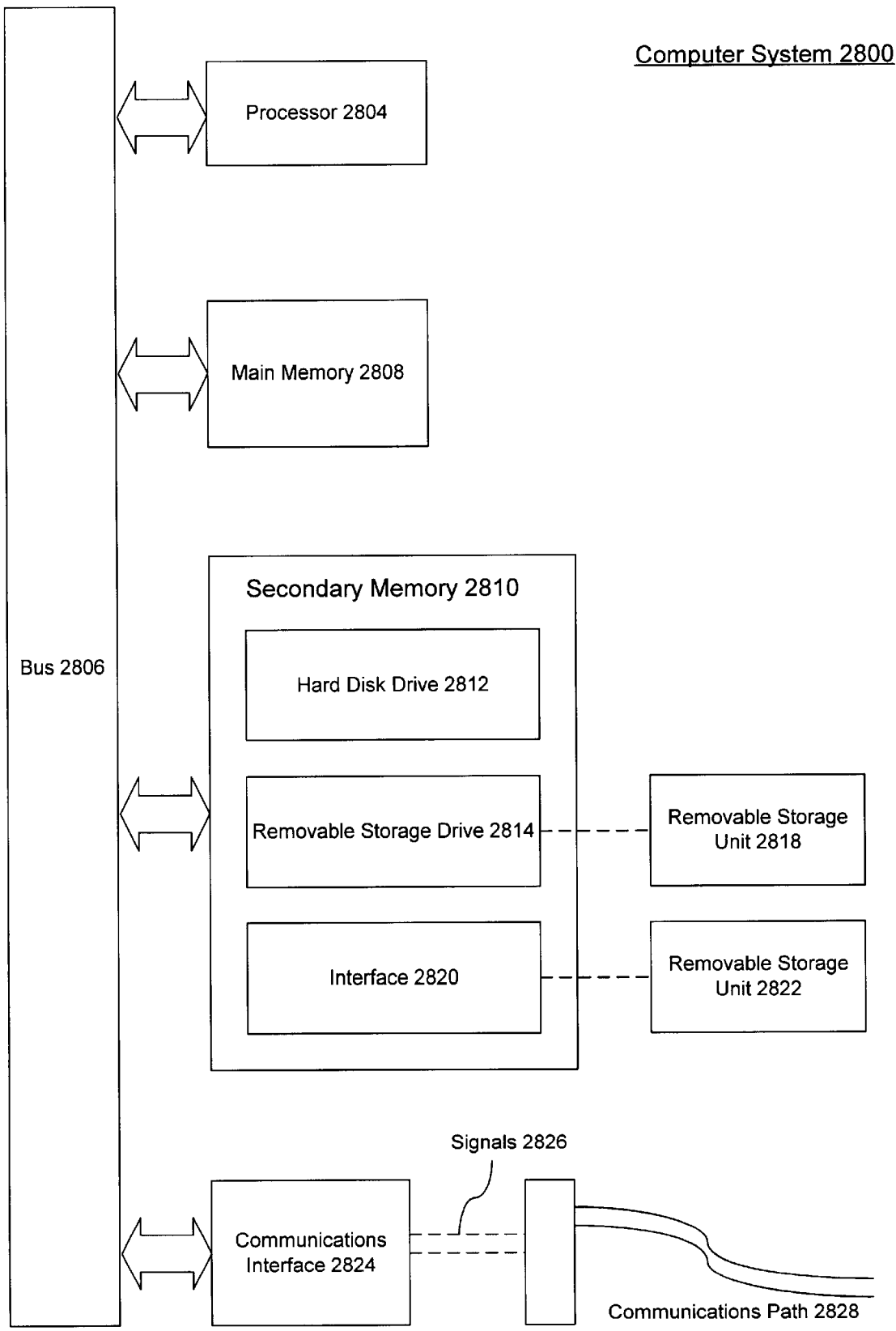

FIG. 28 illustrates a computer system that may be used to implement the synergic engine, as well as other modules, according to an embodiment of the invention.

Figure 29:
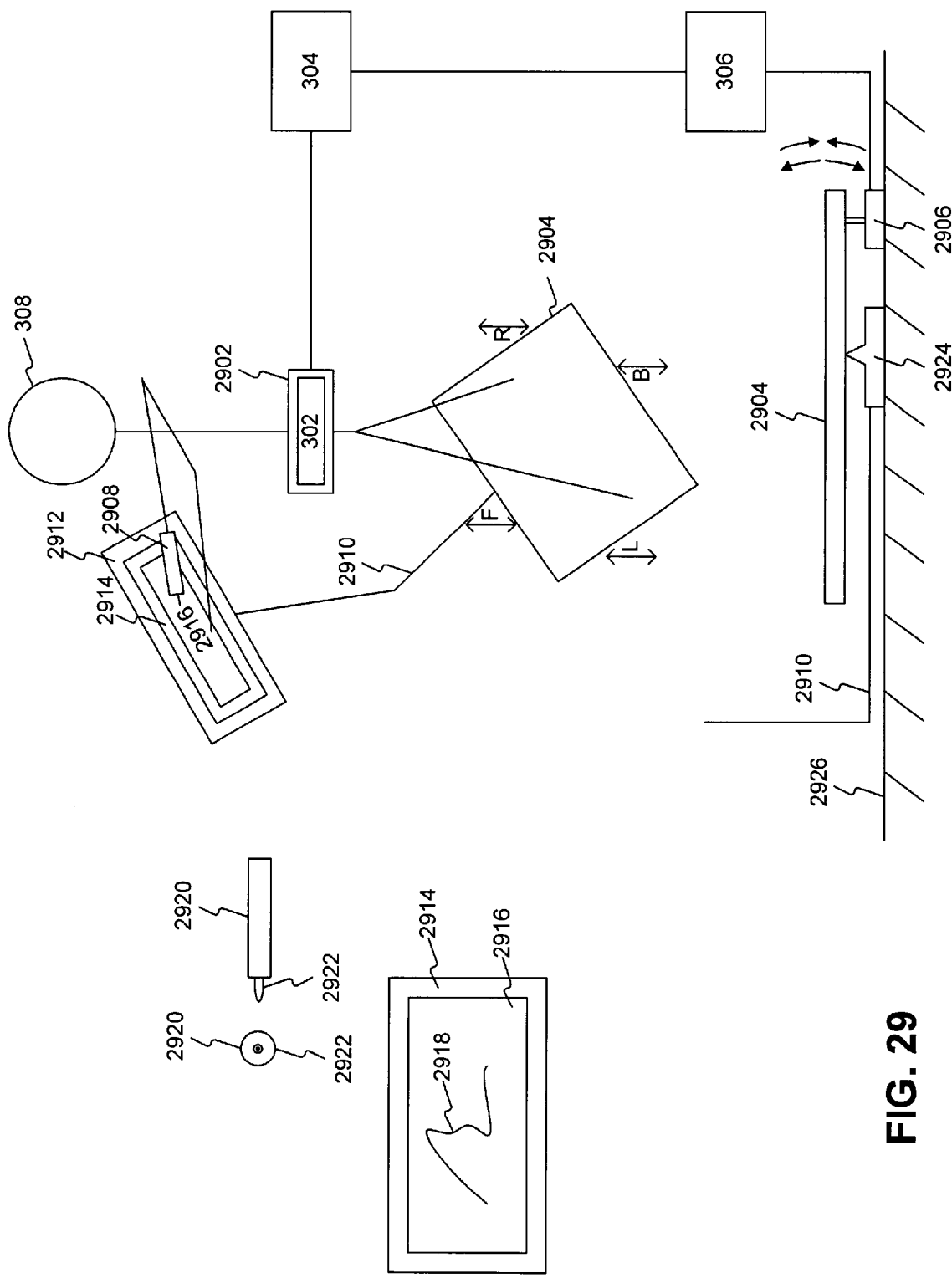

FIG. 29 illustrates an embodiment of the invention relating to learning disabilities.

Figure 30:
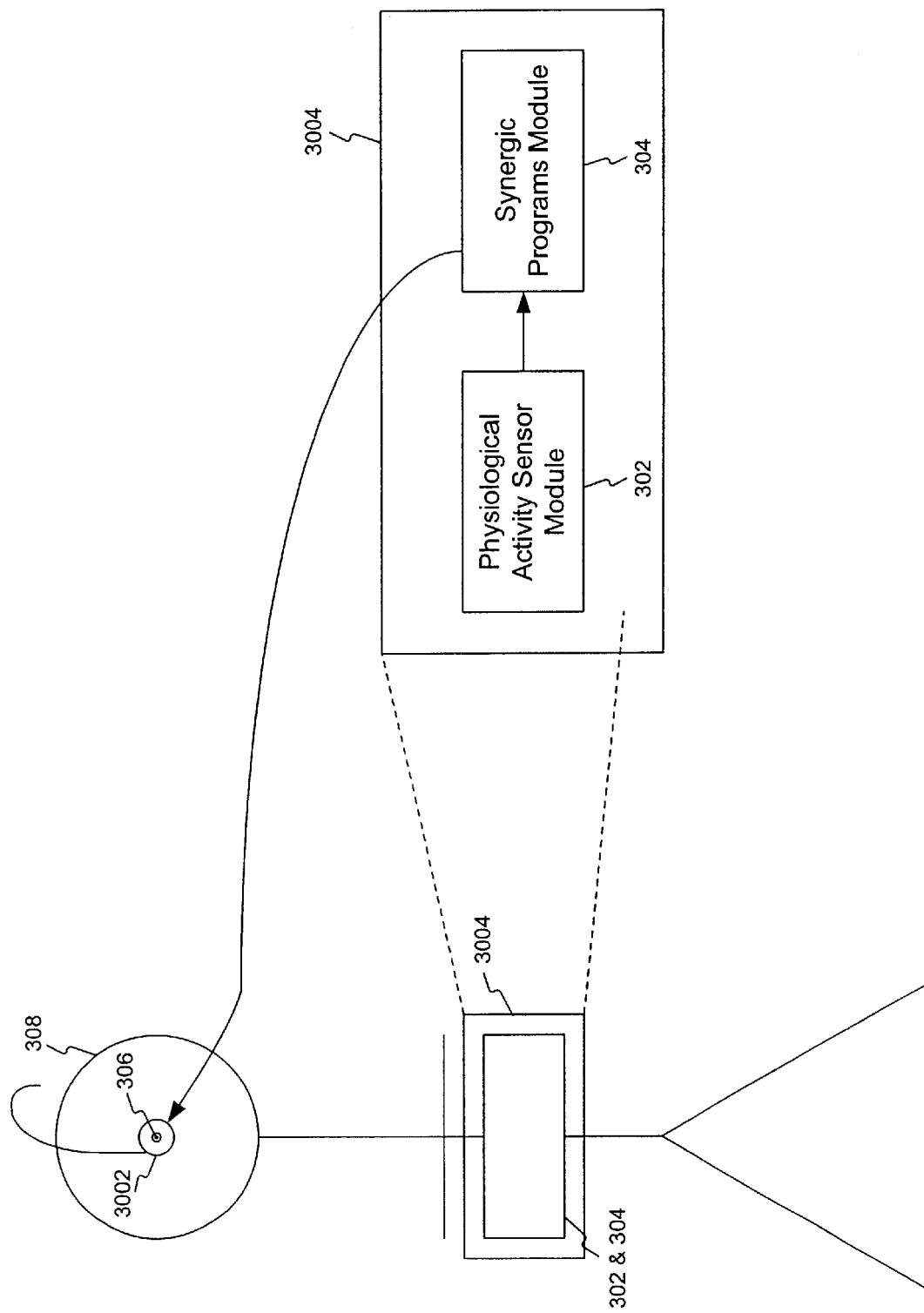

FIG. 30 illustrates an embodiment involving voluntary/active combination as implemented via music according to an embodiment of the invention.

Figure 31:
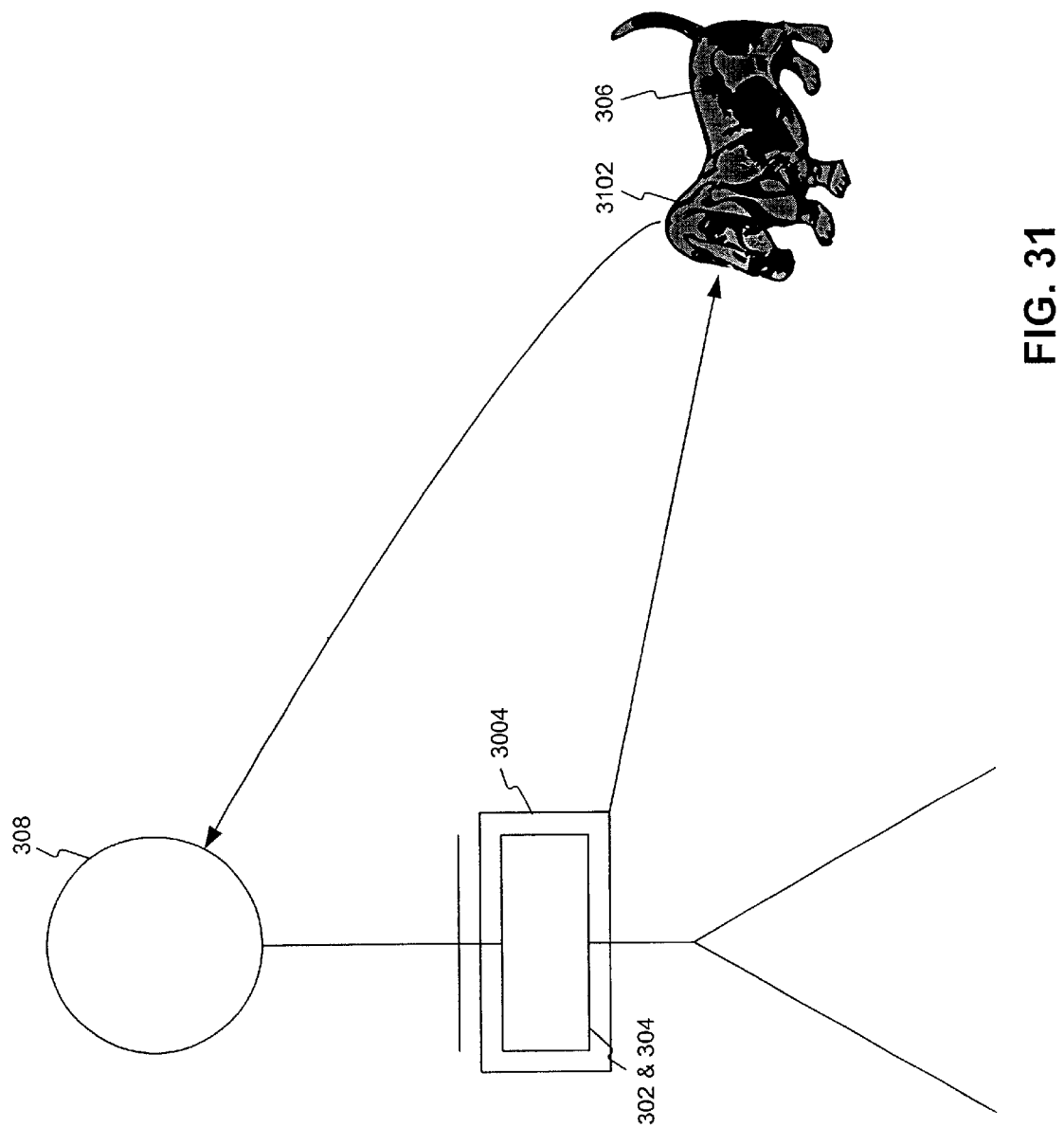

FIG. 31 illustrates an embodiment involving involuntary/reflexive combination as implemented via a toy according to an embodiment of the invention.

Figure 32:
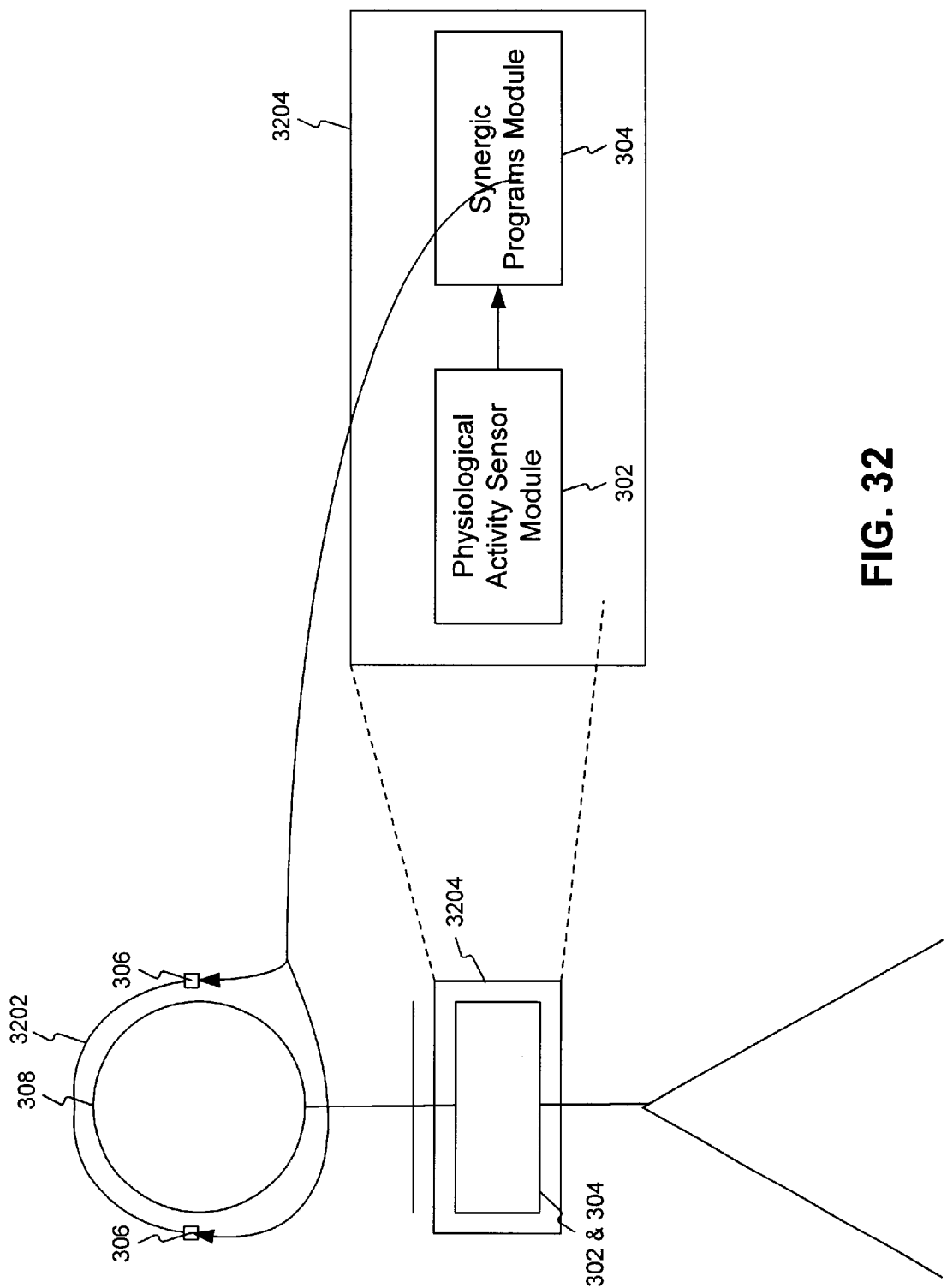

FIG. 32 illustrates an embodiment involving a hybrid that starts in the involuntary class/passive subclass and transitions to the involuntary class/reflexive subclass as implemented via sound according to an embodiment of the invention.

Embodiments of the invention are described with reference to the figures where like reference numbers generally indicate identical or functionally similar elements. Also in the figures, generally, the left most digit(s) (either the first digit or first two digits) of each reference number identify the figure in which the reference number is first used.

DETAILED DESCRIPTION OF THE INVENTION

Table of Contents

1. Theoretical Overview
   1.1. Definitions
2. Overview of Invention
   2.1. Physiological Activity
   2.2. Movements
   2.3. Synergic Timed Correlation of Physiological Activity and Movements
   2.4. Renunciation
3. System Architecture Overview
   3.1. Physiological activity sensor module
      3.1.1. Physiological Sensor
      3.1.2. Signal Conditioning Module
   3.2. Synergic Programs Module
      3.2.1. Signals Library Options Module
      3.2.2. Synergic Programs Options Module
      3.2.3. Synergic Engine
   3.3. Movement Inducement/Change Module
4. System Architecture - Voluntary Class Involvement
   4.1. Active Subclass
      4.2. Reactive Subclass
5. System Architecture - Involuntary Class Involvement
   5.1. Passive Subclass
   5.2. Reflexive Subclass
6. Operation of the Present Invention
   6.1. High Level Operation of the Invention: Obtaining Synergic Timed Correlation of Physiological Activity and Movements -continued Table of Contents 6.2. Developing a Program for a Subject: Populating Synergic Programs Options Module
   6.3. Executing a Program for a Subject
      6.3.1. Monitoring Physiological Activity of a Subject
   6.4. Example - Determining Trigger Timing so as to Correlate with Physiological Activity
7. Embodiments of the Present Invention
   7.1. Class: Voluntary; Subclass: Active
      7.1.1. Tools
      7.1.2. Fitness
      7.1.3. Sports
   7.2. Class: Voluntary; Subclass: Reactive
   7.3. Class: Involuntary; Subclass: Passive
   7.4. Class: Involuntary; Subclass: Reflexive
8. Embodiment of the Present Invention for Learning Disabilities
9. Implementation of the Present Invention in Pacemakers and Biomechanics
10. Conclusion

1. Theoretical Overview

In an embodiment, the apparatus of the present invention is utilized to preferably correlate a gross motor activity involving minimal or no attention, induced to be performed in a temporally varying fashion with an intrinsically varying cyclical physiological activity, the apparatus comprising a physiological activity sensor module, a synergic programs module and a movement inducement/change module.

The present invention also provides a method for correlating a gross motor activity preferably involving low-cognitive activity with minimal or no attention that is performed in a temporally varying fashion with a physiological activity, the method comprising (a) providing signals to a subject using a signals library options module; and (b) performing motor movements requiring low-cognitive activity involving minimal or no attention, according to a program provided by a synergic programs options module. In embodiments, as a result of such correlation, the subject will exhibit an improvement in a condition. One goal of the invention is to improve biomechanical performance.

For illustrative purposes, the invention is described herein as correlating movement with a physiological activity in a target organ and/or physiological system in a time varying fashion. More generally, the invention is directed to correlating movements with a physiological activity in some varying fashion, where time is an example of a variable that may be varied. It is noted that the invention is not limited to this example embodiment involving only time, but may also involve spatial coordination.

The apparatus and methods of the present invention utilize a multidimensional approach to body movements not taught or suggested prior to the invention, namely, a) not prompted by the subject's volition; b) use preferably movements (including but not limited to motor activities) that require or are associated with minimal or no attentional involvement; and c) produce or induce movements in kinematical correlation with internal cyclical or periodical physiological activity. The kinematical correlation is directed towards fulfilling the conditions of: i) reducing attention involvement; ii) improving perceptual attentional mechanisms; iii) minimizing or reducing the loss of degrees of freedom due to the introduction of some degree of synchronic correlation in the timing components of movement; and iv) inducing or producing fluctuations (or also known as qualitative changes) in the timing of synchronized movements, aimed to promote synergic correlation between one or more body parts movement and internal physiological activity.

1.1. Definitions

This section provides definitions of terms used herein. Such definitions are provided in this section for the convenience of the reader, although it is noted that these terms are further described in other sections contained herein. Modifications and/or extensions of the following definitions applicable to the present invention will be apparent to persons skilled in the relevant art(s) based at least on the teachings contained herein.

In the following, the definitions are discussed in the context of the present invention, such that the theoretical overview of the invention is continued in this section.

"Correlation" refers to the timing and/or coordination of a movement that is performed in a varying fashion (such as a temporally and/or spatial varying fashion) with an intrinsically varying physiological activity in a target organ and/or physiological system. In a preferred embodiment, varying correlation refers to the timing of one or more gross motor activities requiring minimal or no attention with one or more intrinsically varying physiological activities.

"Dyslexia" refers to a neuro-developmental disorder that is associated with difficulty of learning, reading, and writing. Dyslexia is characterized by deficits at biological, cognitive and behavioral levels, localized mainly, but not exclusively, in phonological and reading processes. Dyslexia afflicts around five (5) percent of the general population. To date, no practical and effective treatment has been found.

"ECG" is a display of electrocardiographic events. See FIG. 15A. An ECG monitor can provide either a visual (e.g., digital) display or a printed display.

"EEG" is a display of electroencephalographic events. An EEG monitor can provide either a visual (e.g., digital) display or a printed display. For example, an EEG can depict alpha wave activity and beta wave activity.

Alpha waves are slow waves that exhibit an average frequency of about 10 Hz, and beta waves are faster waves that exhibit an average frequency of about 20 Hz and a lower amplitude than alpha waves. See *Physiology*, Berne R. M. and M. N. Levy, Eds., C. V. Mosby Co., St. Louis, p. 266 (1988), and see FIG. 19–9 therein for a depiction of alpha waves and beta waves. The transition from a high attentional involvement state to a low attentional involvement state is reflected by a decrease in beta wave activity and an increase in alpha wave activity.

"Fine motor activity" is an art-recognized term that refers to motor activity that involves fine motor skills such as writing. Fine motor activities require significant attention, so that body parts can be moved in a coordinated fashion. More precisely, fine motor control is characterized by small, generally precise coordinated movements, and many fine motor activities involve the use of the small muscles of the hands. In those cases where these movements have been internalized or learnt, only low attention will be required. Examples of fine motor activities are writing, cutting with scissors, drawing, pouring water and precisely pointing to a small item with one finger instead of waving an arm toward the general area.

"Gross motor activity" is an art-recognized term that refers to motor activity that does not involve fine motor skills, but instead involves the coordinated effort of the large muscle groups and their joints, and here is also considered to involve balance and general patterns of movement. Gross motor activities require minimal or no attention. In contrast to fine motor activity, gross motor activity is characterized by general, large movements, such as waiving an arm, lifting a leg, and throwing a ball.

"Heart cycle" refers to the ejection of blood into the arterial tree from the left ventricle of the heart. In the systolic or initial phase of the heart cycle the heart contraction takes place and arterial blood is ejected from the left ventricle into the aorta, by which the aorta and its arterial branches distend to accommodate to an increase in the demand of blood flow. The diastolic phase follows to the systolic phase to complete the heart cycle. More precisely, it occurs when the ventricle walls expand to receive back approximately the same amount of blood emptied during the previous systole.

A "high-cognitive state" is characterized by a high perceptual attentional involvement. The electroencephalogram shows beta wave activity in the parietal and/or occipital lobes of the brain in a conscious subject. For a subject to perform new fine motor movements, a highly cognitive state is required. Furthermore, mathematical and abstract thinking can only occur in the highly cognitive state.

"Intrinsically varying physiological activity" refers broadly to any cyclical physiological event that is under automatic control and that is characterized by intrinsic variability. Indeed, one characteristic of physiological activity is to exhibit intrinsic temporal variability, i.e., a varying frequency of occurrence over time. In general, physiological activity is regulated by the dynamic balance between sympathetic and parasympathetic neurophysiological control mechanisms. Still more preferably, the term physiological activity refers here to at least one of the breathing cycle, heart cycle, blood pressure wave, pulse wave, hormonal cycle and brain wave activity, although the invention is conceived with physiological activity and is not limited to these examples.

A "low-cognitive state" is characterized by a low cognitive—low sensorial attention involvement. The electroencephalogram shows alpha wave activity in the parietal and/or occipital lobes of the brain in a conscious subject. For a subject to perform gross motor movements, no more than a low cognitive state is required. Learned fine motor movements do not require high sensorial attention processes.

A "low cognitive attention biological region" is here defined as one that mainly deals with gross motoric movements but also may extend to include such fine motoric movements that do not require high sensorial attentional processes because they have been internalized or learnt. It is expected then, that a low cognitive attentional biological region will not heavily tax the neuronal activity of the subject. That is, a relatively reduced level of physiological stress will result from activities associated to low cognitive attentional biological processing.

"Movement" refers broadly to movement by a subject and/or of any of his anatomical parts through space. It may involve muscle participation in a biomechanical process including the corresponding joints, and/or of any muscles, tendons, cartilage, and other tissue taking place in a way which is not independent of sensorial activity. The movement can involve any part or all of the body of a subject. More specifically, it refers to those not fully automated movements involving or correlating to sensorial awareness. Thus, movement in this patent application is distinguished from a movement initiated and sustained by physiological activities that are under full automatic control, such as peristalsis, heart cycle, etc. Movement is here considered to be voluntary, involuntary, active, or passive.

A voluntary movement is one that is performed, for example, by pushing a button, or changing one's activity from seating to walking. In this invention, involuntary movements produced by physical forces are designated as passive, whereas those generated by physiological adaptations or processes are designated as reflexive. Any sensations, feelings or emotions are here considered as resulting from physiological processes. Therefore, movement in all or any part of the body issued involuntarily as a result of those sensations, feelings or emotions are here considered as reflexive movements.

An involuntary movement that is performed reflexively by a subject, includes for example, those taking place in response to tickling. According to the invention, an important involuntary reflexive movement is the one taking place in the oculomotor system when an object inside the field of vision moves away or approaches the eyes, or when the eyes increase the focus on zones where a rapid change in brightness takes place. A passive movement is movement in which the subject or any of the subject's parts are moved by a force acting from outside or from inside the subject, e.g. rocking in a swing. In this patent application, for involuntary passive movements to take place, the subject is not required to initiate any movement, but his/her sensorial system is required to produce some degree of sensorial awareness of the movements to which the body is being subjected. This awareness may result from afferent and/or efferent neural activity. In this invention, physical forces include, but are not limited to, those of mechanical, electromechanical, cohesional, elastical, frantational, electrostatical, electrical, magnetical, electromagnetical, and centrifugal character.

A "cycle" of a physiological activity is the completion of one occurrence of the physiological activity. For example, a cycle of a heart is one heart contraction and expansion (or heart beat), i.e., systole and diastole. Occurrence of a respiratory cycle is one inspiration and one expiration. A cycle of a brain wave is one wave (e.g., alpha, beta, etc.) or any other periodical process in the electrocortical activity.

A "quantified time interval" is a measured time interval of finite duration. One example of a quantified time interval is the R to R interval in an electrocardiogram. See FIG. 15B. In physiological activities that are inherently variable, the duration of the quantified time interval varies over time. For example, for a given subject, even if the average heart rate remains constant (i.e. a constant 60 beats/minute), the R to R interval varies over time (i.e. each RR time interval is different in duration from the next one).

"Performing a movement" refers to the execution and/or realization of the movement. The performance can be voluntary or involuntary, and can be active or passive, reactive or reflexive.

"R to R interval" is the time interval between the peaks of two consecutive R-waves in the QRS complex of the electrocardiogram (ECG). See FIG. 15B. The QRS complex is that portion of an ECG display that reflects ventricular depolarization, see *Physiology*, Beme R. M. and M. N. Levy, Eds., C. V. Mosby Co., St. Louis, p. 420 (1988), and is depicted in that text in FIG. 27–33 at page 422.

"Sensorial indicia" are herein those signals with some level of cognitive content related to the activity to be performed, like when the form of a hand is shown on a screen to indicate to the subject that this particular part of the body has to be moved. The term "signal" may nevertheless be used in this patent application, instead of "sensorial indicia," unless otherwise required for the sake of the explanation. "Sub-interval" is a subset of time within a time interval.

"Synergy" is one among several possible cooperative states observed in open dynamical complex systems. Synergy more specifically refers to the cooperative action of components toward a common goal, such that the effect of the combination of those components gives place to a result having aspects or characteristics not previously contained in each separate component alone. Cooperation attained via synergism is not the same thing as cooperation attained via synchronization and/or entrainment and involves more complex phenomena. Synergism is synonymous of self-emerging cooperation. Open dynamical systems may manifest stability properties in the presence of noise or perturbations in ways resembling those observed in living systems. A precondition for their stability in the presence of noise or perturbations depends on a special cooperation, which they keep among its parts, a synergism characterized by a type of cooperation, which has been denominated "relative coordination" (RC). In the absence of RC, a system under perturbation may disintegrate and/or enter into various forms of chaotic states. In the presence of RC the system will go away from unstable condition and enter into more stable ones in an intermittent fashion of successive spontaneous reconfigurations known in the art under the name of self-organization. An RC is manifested by a dynamical system as long as their separate parts will, despite perturbations, fulfill the following conditions: i) maintain their own intrinsic degrees of freedom; and ii) some degree of limited cooperation such as synchronization in time and/or correlation in space with other parts. Notice that, even if condition ii) imposes a decrease in the degrees of freedom of the cooperating parts, the changing character of the time and/or space correlations among parts goes in the direction of compensating this loss in their degrees of freedom. These changes are the main integrating factor of the parts, having a periodical nature known under the term of "fluctuations".

Thus, synergism is a cooperative end state attained by parts in a non-linear and open dynamical system whose relative spatial-temporal coordination status (primary correlation), it has been destabilize by (incoming/outgoing) perturbations (such but not limited to random perturbations characterized as taking place in the form of fluctuations) (secondary correlation), via the openness of the system.

Because fluctuations in dynamic systems are qualitative in nature (qualitative changes), what is important is the change itself and not the nature of what is changing.

Performing a movement in a "temporally varying fashion" refers to performing the repetition of the movement at different time points inside a quantified time interval of at least two cycles of a physiological activity. For example, if a movement is correlated with the heart cycle, and if the movement is performed once during an R to R quantified time interval in an electrocardiogram, then the length of time after the first R wave in the R to R quantified time interval in which a given repetition of the movement is performed is different than (a) the length of time after the first R wave in the R to R quantified time interval in which the previous repetition was performed, and/or (b) the length of time after the first R wave in the R to R quantified time interval in which the next repetition will be performed.

"Relative coordination" explains cooperation as a particular kind of relationship were, each individual participant component conserves its own identity (its own intrinsic degrees of freedom) nevertheless, constantly aiming, towards some restricted degree of temporal synchronization (frequency lock or amplitude lock, but not both) or some restricted spatial coordination.

The concept encapsulated in 'relative coordination', accomplishes in fusing two apparently non-conciliatory behaviors, that of the parts maintaining their individual freedom-identity, with that of each part interacting as if cooperating to form a larger pattern (a system). The reason for currently treating relative coordination as a non-conciliatory behavior is because it was confused with the trivial concept of 'cooperation' in linear systems (non-complex systems). Cooperation or synchronization in non-complex system, is understood as representing the outcome of a process were the parts have relinquished (waiver) their self-identity (internal freedom) in favor of acquiring a new self-identity namely, that of a "system".

In the methods of the present invention, movement activity is variably by default, because it is correlated with an intrinsically varying physiological activity. In embodiments of the present invention a change in the dynamic balance between sympathetic and parasympathetic control mechanisms can take place. In some embodiments of the invention, the dynamic balance is tilted in favor of an increased parasympathetic control.

The present invention provides a method of producing or performing a movement, the method comprising the execution and/or realization of the movement in a temporally varying fashion and in correlation with the occurrence of an intrinsically varying physiological activity. In an embodiment, the subsequent repetition of the movement is performed or initiated at a time point within a quantified time interval between two cycles of the physiological activity, wherein the time point is different than (a) the time point in the time interval that the previous repetition of the movement was performed, and/or (b) the time point in the time interval that the subsequent repetition of the movement will be performed.

In another preferred embodiment, the execution and/or realization comprises a repetition of the movement at a time point within a predetermined sub-interval of the quantified time interval. More preferably, the subsequent repetition of the movement is performed and/or initiated at a time point in a sub-interval, wherein that time point when the movement was initiated is different than (a) the time point in the sub-interval of the time interval where the previous repetition of the movement was performed and/or initiated, and/or (b) the time point in the sub-interval of the time interval where the subsequent repetition of the movement will be performed and/or initiated.

In the method of the present invention, during some finite period of time in which more than one cycle of the physiological activity occurs, a repetition of the movement can be performed during an interval inside each successive cycle of the physiological activity. For example, if the physiological activity with which the movement is correlated in a temporally varying fashion is heart cycle monitored by electrocardiogram, a repetition of the movement can be performed after every heart cycle, e.g., one repetition per R to R interval in the electrocardiogram.

Alternatively, during some finite period of time, a repetition of the movement can be performed after fewer than each cycle of the physiological activity. For example, a repetition of the movement can be performed after a given heart cycle, but not performed; after each of one or more subsequent heart cycles. The frequency of movement repetition, relative to the frequency of the occurrence of the physiological activity can be varied in any way desired by the administrator (herein an administrator is a person or entity that operates the present invention, e.g., an expert system, a human operator, and so forth). A discrete ratio of the occurrence of a physiological activity to the repetition of the movement can be set. For example, if the physiological activity is heart cycle, a repetition of the movement can be performed during every fourth R to R interval (a 1 to 4 ratio), every fifth R to R interval (a 1 to 5 ratio), every sixth R to R interval (a 1 to 6 ratio), etc. Alternatively, the frequency of movement repetition, relative to the frequency of the occurrence of the physiological activity can be varied in a non-discrete way, such that a discrete ratio of the occurrence of a physiological activity to the repetition of the movement is not set, or alternatively, set by a random or any mathematical function.

In an example method of the present invention, the movement is preferably a gross motor movement. In the method of the present invention, the physiological activity with which a temporally varying movement is correlated is characterized by intrinsic temporal variability. That is, the occurrence of the physiological activity varies over time, such that the frequency of the occurrence of the physiological activity is variable. Physiological activities to which the movement can be correlated include, but are not limited to, heart cycle, the breathing cycle, the hormonal cycle and brain wave activity.

If the physiological activity is the heart cycle, it can be monitored by any suitable method. Suitable methods available to those skilled in the art include, but are not limited to, monitoring electrocardiogram, blood pressure, and pulse. In a preferred embodiment, heart cycles are monitored by electrocardiography (ECG), using any suitable ECG monitor. Such monitors are well known to those skilled in the art, and can be purchased, for example, from KahnTact USA, Inc. (Hillsdale, Ill.), P. M. S. (Instruments) Ltd. (Berkshire, UK). The ECG monitor can be stationary or portable (e.g., a Holter monitor). Preferably, the subject either wears a heart chest strap device that contains one or more ECG electrodes, or the subject is connected to an ECG monitor by skin electrodes. In an embodiment, the subject wears a heart chest strap that contains one or more ECG electrodes. (Biopac Systems, Inc.: ECG100C Electrocardiogram Amplifier with Multilead ECG cable TSD155C and Vernier Software & Technology (for non medical applications): EKG-BTA Sensor or EKG-DIN Sensor.)

In an embodiment, the movement is correlated with heart cycle by performing the movement during a predefined sub-interval inside the R to R interval. Movement variability is established by performing a given repetition of the movement during a time interval within an R to R interval that is different than the time interval in the R to R interval that the previous repetition of the movement was performed, and/or the time interval that the subsequent repetition of the movement will be performed.

In an alternative embodiment, movement variability is established by performing a given repetition of the movement from a time point within a sub-interval of the R to R interval that is different than the time point in the sub-interval of R to R interval that the previous repetition of the movement was performed, and/or the time point in the sub-interval of the R to R interval that the subsequent repetition of the movement will be performed.

Alternatively, heart cycle can be monitored by monitoring blood pressure waves. A suitable monitor is one that allows the administrator or automated by signal processing computer means to discriminate between the systolic and the diastolic phases of the heart cycle. Such monitors are well known to those skilled in the art, and can be purchased, for their direct use or after adaptation to a particular embodiment. Diagnostic devices can be purchased from Medis Medizinische Messtechnik GmbH (www.medis-de.com). Example models are rheoscreen compact for an impedance plethysmographic technique or Rheoscreen light for photoplethysmographic technique. Another manufacturer is Biopac Systems, Inc, which produces Model NIBP1OO, a noninvasive blood pressure amplifier.

Alternatively, the heart cycle can be monitored using a pulse monitor. A suitable monitor is one that allows the administrator or by automated signal processing computer means to discriminate between the systolic and the diastolic phases of the heart cycle. Such monitors are well known to those skilled in the art, and can be purchased for their direct use or after adaptation to a particular embodiment. For example, from Biopac Systems Inc, Transducer TSD200 for photoelectric pulse plethysmograph. If the physiological activity is the breathing cycle, it can be monitored by any suitable method, including but not limited to, a respiratory monitor that allows the administrator or by automated signal processing computer means to distinguish between inspiration and expiration of the subject. Suitable respiratory monitors are well known to those of ordinary skill in the art, and are available for their direct use or after adaptation to a particular embodiment, from manufacturers such as Biopac Systems Inc., namely TSD201 Respiratory Effort Transducer or Vernier Software & Technology, (for non medical applications), namely Respiration Monitor Belt RMB with Gas Pressure Sensor. If the physiological activity is any electrocortical brain wave cycle (i.e. its frequency and/or amplitude), it can be monitored by any suitable method used by those of ordinary skill in the art, including, but not limited to, monitors for electroencephalography (EEG). Suitable EEG monitors are well known to those of ordinary skill in the art. For example, EEG monitors that are available from manufacturers such as W. R. Electronics Co. (Stillwater, Minn.), Nicolet Biomedical, Inc. (Madison, Wis.), Oxford Instruments Medical (Surrey, UK), Walter Graphtek GmbH (Leubeck, Germany), and Neuro Scan Labs (Sterling, Va.). Biopac Systems, Inc manufactures EEG100C Electroencephalogram Amplifier and CAP 100C EEG Electrode Cap.

In an embodiment of the invention, the predetermined sub-interval is an interval of time that begins at an R-wave in the QRS complex of an electrocardiogram and ends prior to the R-wave in the subsequent QRS complex.

In an embodiment of the present invention, the movement is preferably performed while in a low attention state. More precisely, when minimal or no attention is required. Thus, the method of performing a movement comprises repeatedly performing the movement in temporally varying correlation with the occurrence of an intrinsically varying physiological activity, wherein the movement is performed while in a low attention state, wherein the time points where the movement starts and/or ends is different than (a) the time points in the sub-interval of the time interval that the previous repetition of the movement was performed, and/or (b) the time points in the sub-interval of the time interval that the subsequent repetition of the movement will be performed, and wherein during a finite period of time in which more than one occurrence of the physiological activity occurs. A repetition of the movement is not always performed after each occurrence of the physiological activity. In an embodiment, the movement is a gross motor movement.

If the movement is correlated with the heart cycle, the method comprises repeatedly performing the motor movement in temporally varying correlation with the heart cycle, wherein the movement is performed while in a low attention state implying minimal or no attention effort, wherein a repetition of the movement is performed between time points within a predetermined sub-interval of time in the R to R interval, wherein the subsequent repetition of the movement is performed between time points in a sub-interval that are different than (a) the time points in the sub-interval of the R to R interval that the previous repetition of the movement was performed, and/or (b) the time points in the sub-interval of the R to R interval that the subsequent repetition of the movement will be performed, and wherein a repetition of the movement may not always be performed during each R to R interval. In another embodiment, the movement is a gross motor movement.

The apparatus and methods of the present invention utilize a multidimensional approach to body movements not taught or suggested previously, a) not prompted by the subject's volition; b) use preferably motor activities that require or are associated with minimal or no attentional involvement; and c) produce or induce motor activities in kinematical correlation with cyclical or periodical physiological activity. The kinematical correlation is directed towards fulfilling the conditions of: i) reducing attention involvement; ii) improving perceptual attentional mechanisms; iii) minimizing or reducing the loss of degrees of freedom due to the introduction of synchronic correlation in the timing components of movement; and iv) inducing or producing fluctuations in the timing of synchronized movements, aimed to promote synergic correlation between one or more body parts movement and/or physiological activity.

For most subjects, the variability of a physiological activity, e.g., heart cycle, is decreased when attention is focused, and the variability of the physiological activity increases going back to its basal value, when attention ceased to be focused. In an embodiment where voluntary movements are directed by incoming sensorial signals, the subject is induced to move from a higher attention state towards a lower attention state. In order for the subject's attention to change towards a lower cognitive state, the subject is induced to "renounce" to his current higher-cognition state. To accomplish some degree of renunciation of his/her relatively higher-cognition state, a series of sensory signals are presented to the subject in a random fashion or in a specially preselected sequence. Each signal is different than the previous signal. The subject is instructed to start and/or end a preferably simple motor movement in response to the start and end of each signal. For example, the subject starts and stops moving a computer mouse in response to each signal.

The signals can be any single or multiple sensorial signals, e.g., aural, visual, or tactile signals, or any combination thereof. When the subject is first presented with the novel signals, and in order to execute the movement the subject focuses his attention on the signals, and naturally wishes to predict what the next signal will be, when the next signal will arrive, and from where the next signal will emanate. Because the signals, their type and location, are changed at random, or in a complex preselected series, it is difficult for the subject to predict the particulars (when, what, where, etc.) of the next novel signal. The subject may "jump the gun," i.e., will perform the motor movement, for example, depressing a button, before the next signal has been presented.

The longer the subject is exposed to novel signals, the wearier he becomes with trying to predict the occurrence of the next novel signal in order to start and/or end the indicated movement. Eventually, the subject stops trying to predict the particulars of the next signal, and only will follow its timings in order to execute the movement. By this process, the subject renounces to cognitive efforts related with the signals and is therefore driven from a higher-attention state toward a more relaxed, lower-cognition state. (Note when the subject goes from a higher-attention state to a lower-attention state the subject also renounces herein.) The process of moving from a higher-cognition attention state to a lower-cognition attention state is called herein "renunciation" of the high-cognition state. Once renunciation has occurred, the subject has entered a lower-cognition state. The subject will more easily internalize the motor movement, and will perform the movement more effectively in response to incoming signals, i.e., without "jumping the gun."

In an embodiment, the subject entering into a low-cognition state also implies entering into a low-emotional state with respect to the signals, forces, and/or stimuli being presented to the subject. This may involve, for example, selecting those signals, forces and/or stimuli that the subject is not emotionally attached and/or presenting the signals, forces and/or stimuli such that the subject's emotional attachment is diluted over time, and thus furthers the renunciation process.

Renunciation will occur more quickly in response to combined types of novel signals, than in response to a single type of novel signal. For example, a subject to whom a combination of novel aural and visual signals are provided will renounce the high-cognition attention state more quickly than he will if presented with only novel visual signals or only novel aural signals, because it is more difficult to anticipate their combinations than each one of them separately.

The subject has renounced the higher-cognition attention state and entered the lower-cognition attention state, while the novel signals are timed with a physiological activity, such as the heart cycle. Thus, the movement is correlated with the physiological activity with a low taxation to attentional mechanisms.

Assume the heart cycle is the physiological activity with which the induced movement is to enter a state of relative coordination (RC) in order to achieve synergism. In an embodiment, the signals will be delivered, and the movement performed, at the same sub-section in each heart cycle, for example, during diastole (but at different intervals within the diastole) and not at every RR interval, in order to introduce some degree of fluctuations in the time synchronization, as it is required to achieve RC. For example, after repeated sessions the subject may experience a measurable improvement in his learning disability condition. This improvement is correlated to an improved "synergy" between his movements and physiological activity, e.g., hand-oculomotor coordination in synergic correlation with the heart cycle.

2. Overview of Invention

Figure 1:
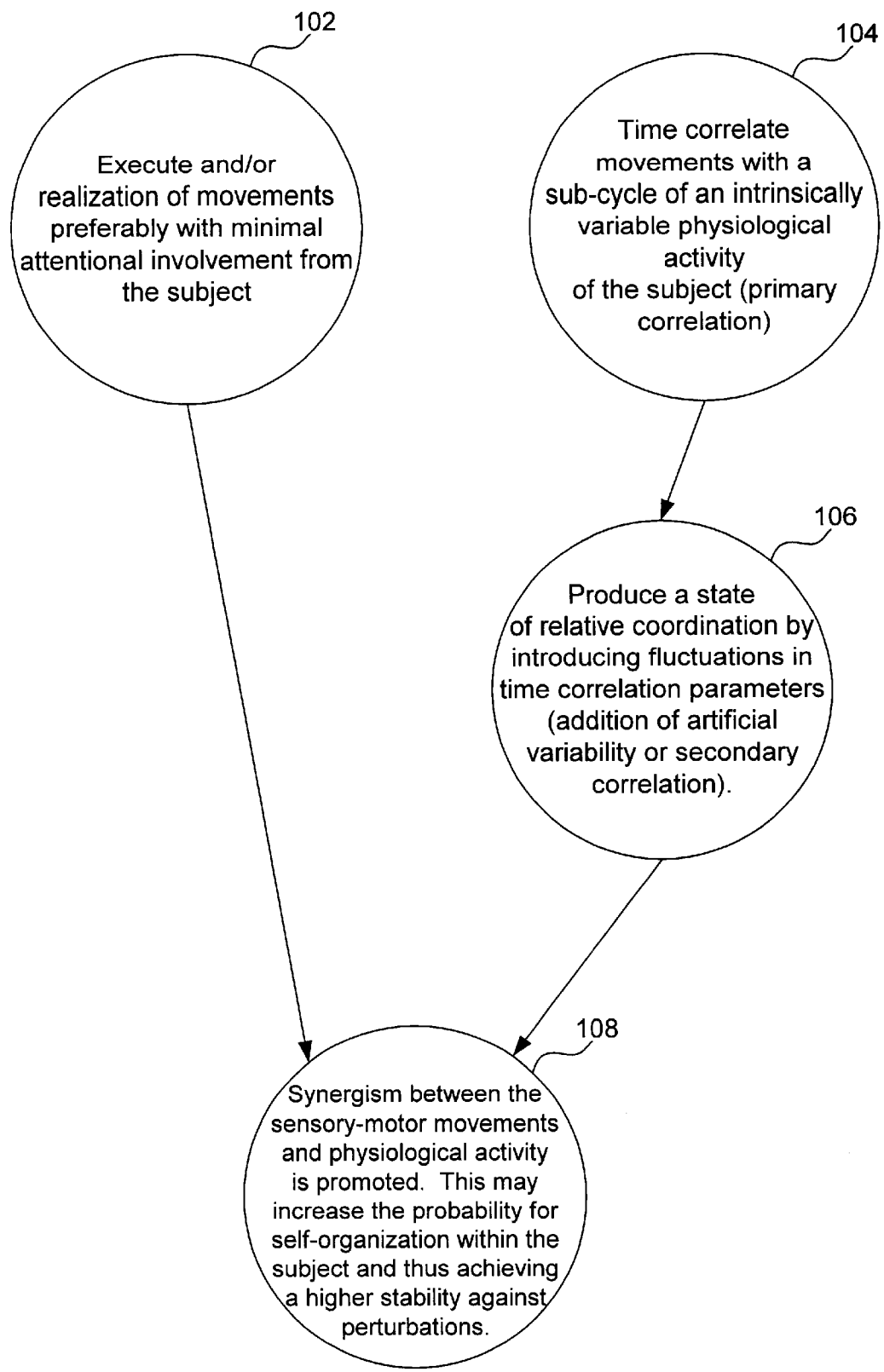
FIG. 1 illustrates a high level representation of the invention according to an embodiment of the invention.

The present invention provides an apparatus, method and computer program product to produce or direct movements in synergic timed correlation with an intrinsically varying physiological activity of a subject. An embodiment of the present invention promotes synergism between voluntary and/or involuntary movements of a subject's anatomical parts, with ongoing changes in one or more selected physiological activities of the subject, including but not limited to the heart, lungs, brain, hormonal and neural activity. A high level representation of the invention is illustrated in FIG. 1. Referring to FIG. 1, reference number 102 refers to, in general, execution and/or realization of movements by a subject with preferably minimal attentional processing and/or emotional involvement. More particularly, with preferably minimal attentional effort. In the case when movements are voluntarily executed by paying attention to sensorial signals, the invention provides means by which a reduction in attentional and/or emotional effort can be achieved via the concept of renunciation. Reference number 104 indicates that the movements are done in timed correlation with physiological cyclical activity of the subject (primary correlation). According to embodiments of the present invention, reference number 106 illustrates the additional and necessary condition (fluctuations in time correlation parameters) to achieve relative coordination between the movement and physiological activity, in order to have some probability that synergism will be triggered between the movements and physiological activity of the subject (addition of artificial variability or secondary correlation). This synergism (or synergic timed correlation) may increase the probability for self-organization within the subject and then of achieving a higher stability against perturbations (108). This higher stability within the subject may help the subject to overcome certain problems or limitations or conditions of the subject. Furthermore, movements can be performed by a higher degree of automatism by which energy consumption by the subject for the same task may be reduced (e.g., jog better and longer). Some among the many embodiments of this invention represents a new research tool to study and to influence the living body, which is here considered as an open dynamical system. In alternative embodiments, only the primary correlation step 104 is used to promote the synergism of step 108.

More specifically, synergic timed correlation involves at least two major steps (see FIG. 14). First, achieve some degree of synchronization between the movement and the physiological activity (which is naturally variable) (step 1402). Second, assign an artificial and additional variability to the timings of the induced movement (step 1404). In an embodiment, such variability is based on one or more variables. For example, if such variability is represented by V, then V can be represented as follows (although four variables are shown in the following example, in practice any number of variables could be used to represent V):

$$V = A + B + C + D$$

Each variable can be arbitrarily established, or can be established by any random or mathematical function. Because fluctuations in dynamic systems are qualitative in nature, what is important is the change itself and not the nature of what is changing. For example, the value of variable A can be determined according to any random or mathematical function, or can be arbitrarily established, or can be otherwise set.

Each variable can itself be based on any number of variables. For example, variable A can be represented as follows (although four variables are shown in the following example, in practice any number of variables could be used to represent A):

$$A = A1 + A2 + A3 + A4$$

Each of these variables can be arbitrarily established, or can be established by any random or mathematical function. As it is well known in the relevant arts, each of the variables may have a range of possible values.

This range of possible values may be pre-calculated and pre-stored in a table for look-up by the present invention as necessary. Alternatively, the value of each variable may be generated on-the-fly via an algorithm.

The above operation of the invention can be extended to any level. Thus, for example, any of variables A1, A2, A3, and/or A4 can each be based on any number of variables, and any of those variables can be arbitrarily established, or can be established by any random or mathematical function.

In some embodiments, the invention is aimed to optimize and/or correct and/or improve and/or modify human physiological and/or cognitive related activity which could be facilitated or benefited by promoting synergism between the movements of all or any body parts, and physiological activity. To aid in the understanding of the present invention, three main concepts utilized herein will be described, including: (1) intrinsically varying cyclical physiological activity, (2) motoric or any other movements, and (3) the synergic timed correlation between (1) and (2).

2.1. Physiological Activity

Physiological activities are well known to persons skilled in the relevant art(s) and include but are not limited to the hormonal cycle, the breathing cycle, the heart cycle, most neurological activity, and so forth. One common trait of physiological activities is the temporal variability in their cycles. This is sometimes herein referred to as "intrinsic temporal variability of a physiological activity." Another common trait is the automatic nature of the physiological activity, where the activity happens without any attention or cognitive participation on behalf of the subject. In fact, physiological activities automatically occur in all species. Although physiological activities are not directly concerned with the environmental events that occur outside the body itself, cognitive or attentive activities by the subject generally done by his interactions with the environment, may decrease the variability in the cycles of the physiological activities.

2.2. Movements

The present invention focuses on the movements of any part of the subject's body, such as those produced by the skeletal muscles involved in the biomechanical balance and general movements, including both the voluntary and involuntary movements of the subject's anatomical parts. In an embodiment, the present invention is concerned with promoting balancing and gross motoric movements (as well as a better relationship in motor perceptual processing) and also to facilitate fine motoric movement of the subject, all of which are described next.

In very young children, gross motoric movements are automatic and require little sensorial external attention from the subject. Gross motoric movements include, but are not limited to, postural modes (e.g., seating, flipping over on to back, side or stomach, crawling), mechanical activity perturbations towards the environment of subject's limbs (e.g., sucking, touching, holding, nibbling), and phonological capabilities (e.g., making sound, crying, pronunciation of vowels). In humans, the biological development of the gross motoric stage occurs from inside the womb to about 2½ years old.

Once learned, fine motoric movements involve the subject's low cognitive attention capabilities and require little sensorial external attention from the subject. Fine motoric movements include, but are not limited to, limbic motoric activity involved with maintaining postural balance such as standing, walking, running, etc., phonological pronunciation of consonants (e.g., b, p, m), and propioceptive activities. In humans, the biological development of the fine motoric (after learning involves low cognitive attentional) stage occurs from around 2½ to 7 or 8 years of age.

In general, gross and fine motoric movements may include any one or more of the body's muscles, groups of muscles or groups of muscle joints, like the facial muscles or those in the oculomotor system, or those involved in the chewing process, or those controlling the vocal cords, as well as any anatomical part or parts of the body like the eyes, eardrums (hammer, anvil and stirrup), hands, feet and/or any of their fingers, the arms and forearms, both legs, neck, head, and so on.

2.3. Synergic Timed Correlation of Physiological Activity and Movements

"Synergic timed correlation" relates to the correlation of a temporally varying movement with an intrinsically varying physiological activity. The variability in a cycle of a physiological activity of the subject is monitored, and the subject is induced to perform a movement in a variably timed fashion. This variably timed fashion is such that the time variability of the movement is correlated with the variability of the physiological activity cycle in such a way that the total variability of the movement is different and higher than the temporal variability of the physiological activity alone.

To obtain synergic timed correlation, some degree of coordination of movement must be first obtained, with respect to the intrinsically varying physiological activity. Then, additional temporal variability is assigned to the movement. The temporal variability of the movement is correlated to the temporal variability of the physiological activity, but the timing of the movement never becomes synchronized with the timing of the occurrence of the physiological activity, such that its variability will be higher than the intrinsic physiological variability with which it was correlated.

In this invention, movements are typically correlated with physiological timings. Nevertheless, they can be interrupted when for example physiological thresholds measured or calculated by those same timings are reached. In some embodiments, physiological timings may drive forces that will in turn produce involuntary movements in the body. Combination of physiological timings values with their changes can be used, through dedicated algorithms, to produce new and artificial timings derived from the natural cycles of the organism in order to induce or produce correlated body movements. Nevertheless, movements are always an end product, the net effect of time correlation. An instrumental feedback link to the physiological timings is not necessarily provided. In most embodiments, if changes in the physiological timings will take place as a consequence of the movements they will be the result of normal physical effort and/or of synergism, but not of an instrumental feedback process. Nevertheless, some embodiments may include instrumental feedback.

The teachings of this invention, promoting synergism in the organism, by correlating movements with physiological functions, clearly departs from the concepts and understandings conveyed in the practice/instrumentation of 'Biofeedback'.

The practice proposed by this patent application aims to accomplish synergism by producing fluctuations between modes of synchronization (or of entrainment) between movements of the body and physiological activity and modes of complex (but deterministic) relationships between them. These fluctuations between opposite modes of correlations are here assumed to characterize a synergic mode, thus preventing all absolute entrainment or coherent modes to take place. Nevertheless, the entrainment mode could be the ground state from where a syngeric mode could be achieved.

The level or degree of entrainment among physiological activities has recently become a preferred way for monitoring a successful outcome of instrumental biofeedback (e.g., EEG and ECG). In instrumental biofeedback the subject directs his or her volitional efforts according to cognitive goals and/or emotional desires. To the contrary, this patent application teaches a way of synergism between movements and physiological activity by means of lowering the involvement of cognitive and emotional factors.

Moreover, in the present invention, 'volition' plays no essential role. This invention is mainly geared toward promoting the correlation of movements with physiological functions by gradually attenuating and eventually totally disengaging from the active role played by the subject's perception or will power (decision making) during the execution and realization of movements.

In general, intention-volitive mechanism plays an essential role in the practice of biofeedback. In the present invention, the volitive-intention factor is systematically played down while promoting correlation of movements with physiological functions.

Our invention treats interactive components in the process of execution and realization of movements as parts of a real dynamical non-linear system (high degrees of freedom).

In contrast, we see biofeedback as an approach that treats the biological system as if possessing a low complexity meaning, that the interaction among its components can be treated as if in a linear system (few degrees of freedom). In biofeedback, aiming for synchronization to influence the biological system is consistent with this approach.

In order to further clarify differences between a synergic emergent process, and that of an instrumental biofeedback process, whenever the term "Synchronization" (temporal entrainment) or "Coordination" (spatial entrainment) appears herein, it should not be confused or exchange with the term "Relative Coordination" (RC), a critical step in promoting synergism, in the present invention.

Relative coordination explains cooperation as a particular kind of relationship where, each individual participant component conserves its own identity (its own intrinsic degrees of freedom) nevertheless, constantly aiming, towards some restricted degree of temporal synchronization (frequency lock or amplitude lock but not both) or some restricted spatial coordination.

The concept encapsulated in 'relative coordination', accomplishes in fusing two apparently non-conciliatory behaviors, that of the parts maintaining their individual freedom-identity, with that of each part interacting as if cooperating to form a larger pattern (a system). The reason for currently treating relative coordination as a non-conciliatory behavior is because it was confused with the trivial concept of 'cooperation' in linear systems (non-complex systems). Cooperation or synchronization in non-complex system, is understood as representing the outcome of a process were the parts have relinquished (waiver) their self-identity (internal freedom) in favor of acquiring a new self-identity namely, that of a "system".

In some embodiments, the variability of the movement and the variability of the physiological activity differ at all times. In other embodiments, the variability of the movement and the variability of the physiological activity differ during some cycles of the physiological activity, but are the same during other cycles of the physiological activity. Also, the variable that is varied may differ from embodiment to embodiment (that is, embodiments may utilize variables other than those related to time).

In order for the movement to be performed in a "variably timed fashion" there must be some sort of signal, stimuli or force inducing the movement to occur that is directed towards the subject.

A synergic state is, by definition, more immune to perturbations and therefore implies that the execution of a biomechanical process, if cognitive processing is assumed to remain constant, will require less energy to be accomplished. To fulfill a task in a synergic way implies an improvement of the work being performed. This improvement, geared to reduce energy consumption, is in fact a main goal of normal parasympathetic nervous system activity. Promotions of synergism in the body will generally be reflected, under equal conditions in perceptual attention mechanisms, in an improvement of parasympathetic activity and this can be measured in several ways, well known for those versed in the art.

In the present invention, movements are variably correlated with an intrinsically varying physiological activity, such that the dynamic balance between sympathetic and parasympathetic control mechanisms can, in some embodiments, be tilted in favor of parasympathetic control.

The present invention involves both the correlated voluntary and/or involuntary movements of the subject, resulting in various embodiments of the present invention. These various embodiments are introduced in Table 1 below and are described in detail herein.

TABLE 1

| Type of Subject Involvement | |
| --- | --- |
| Class | Sub-class |
| Voluntary | Active |
|  | Reactive |
| Involuntary | Passive |
|  | Reflexive |

As shown in Table 1, embodiments of the present invention are divided into two classes, including voluntary and involuntary. The voluntary class is further divided into two sub-classes, including active and reactive. Likewise, the involuntary class is further divided into two sub-classes, including passive and reflexive. Thus, an embodiment of the present invention provides the means and methods by which the subject can consciously or voluntarily be involved in the execution and/or realization of the correlated movement, either by participating in active involvement or reactive involvement. Active voluntary involvement is described below with reference to FIG. 8. Reactive voluntary involvement is described below with reference to FIG. 9.

Another embodiment of the present invention provides the means and methods by which the subject is involuntarily involved in the correlated movement. The involuntary involvement is broken into passive involvement and reflexive involvement, both of which are described below with reference to FIG. 10.

2.4. Renunciation

Renunciation is here defined as some degree of disengagement from the cognitive and/or emotional process associated with the execution of a voluntary movement. As referred to above, a transition from a non-synergic to a synergic state goes together with a reduction in the energy consumption required for the execution of the same task, as long as attention-perceptual processes are kept at the same level of effort. Nevertheless, to execute voluntary movements triggered by the perception of different sensorial signals, an attention process related to the cognitive content of those signals will be necessarily involved, in addition to the attention effort related with starting and/or ending movement according to signals and their timings. Repetition of the same identical signal for triggering the movement may appear to be a simple solution to avoid extra attention efforts. Nevertheless, invariance of the signal plays in here the role of a negative factor because synergism strongly depends upon fluctuations (also referred to as qualitative changes). Repetitions of any sort are bound to generate processes diminishing variability and therefore preventing fluctuations, which in turn may strongly decrease chances for a synergic process to take place.

During the execution of voluntary correlated movement, the mechanisms of attention can be nevertheless driven away from their natural cognitive and normal environmental oriented tasking, and be bound instead to simply follow an "internal physiological timing automatism". With the present invention, attention mechanisms of the subject are driven towards looking "inwards" (i.e., to the internal physiological activity) and not "outwards" (i.e., to environmental changes). When attention to sequential sensorial indicia or signals is required, each successive indicia is made to change at random but from a pool of many possibilities (or, alternatively, in a pre-selected order given by a deterministic algorithm involving those for stochastic processes) such as to make almost impossible for the subject to predict what the next indicia will be, when the next indicia will occur, or from where the next indicia will emanate, therefore driving cognitive attention mechanisms towards a relaxation state. Indeed, the subject's cognitive attention mechanisms associated with the different signals triggering the movements are gradually induced to "give up" and relax. This process is referred to herein as "renunciation" (see 202 of FIG. 2). As a result, the probability that the correlation of the movement with the physiological activity will enter into a synergic mode will be higher. Renunciation is further described next with reference to FIG. 2.

Figure 2:
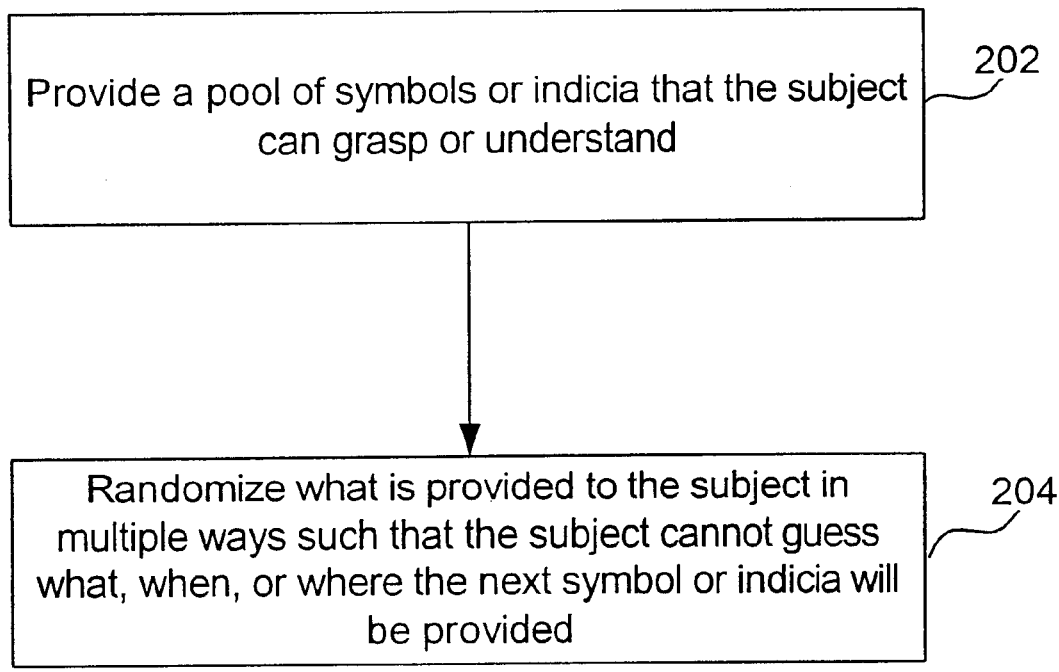
FIG. 2 illustrates a renunciation concept according to an embodiment of the invention.

Referring to FIG. 2, control starts at step 202. In step 202, the present invention provides a pool of indicia (e.g., symbols) that the subject can grasp or understand. A subject can renounce to be engaged in those cognitive processes for which, in the first place, he is able to grasp or understand. The subject cannot renounce subject matter which he cannot grasp or understand. For this reason, a particular process of "renunciation" can be induced by way of exposing the subject to a high variability of what considered separately, are for him affordable and understandable mental processes. For mental retarded subjects, signals should be much more simple than for normal subjects, for example. Control then passes to step 204.

In step 204, indicia are provided in multiple ways to the subject in such a way that the subject cannot guess or predict what the next indicia (e.g., symbol) will be, when the next indicia will occur, or from where the next indicia will emanate. The flowchart in FIG. 2 ends at this point. Thus, the variable timing of symbols or indicia determines when a movement is performed.

Accordingly, embodiments of the present invention provide means and methods to make possible a synergic association between movements (such as but not limited to motoric) and intrinsically varying physiological activity, while also gradually attenuating the subject's normal attentional cognitive and/or emotional participation in motor control. Furthermore, embodiments of the invention make possible the execution of a new kind of movements (such as but not limited to motoric) in which the subject will enter into some degree of renunciation for grasping the meaning content of the indicia being displayed in order to trigger voluntary movements.

Further, embodiments of the present invention provide a means and method for an auto-observation mechanism that occurs mainly at a low cognitive attention biological region, allowing only a passive cognitive attention awareness of the timed indicia that are synergically correlating the movement with a physiological activity. As defined above, "low cognitive attention biological region" is here defined as one that mainly deals with gross motoric movements but also may extend to include such fine motoric movements that do not require high sensorial attentional processes because they have been internalized or learnt. It is expected then, that a low cognitive attentional biological region will not heavily tax the neuronal activity of the subject. That is, a relatively reduced level of physiological stress will result from activities associated to low cognitive attentional biological processing. Thus, the present invention is characterized by: (1) providing means and methods to induce synergic correlation of a temporally varying movement with an intrinsically varying physiological activity; and (2) in embodiments for the execution of voluntary movements it can reduce involvement of cognitive, sensory-attentional processes. The system architecture of the present invention is described next.

3. System Architecture Overview

Figure 3:
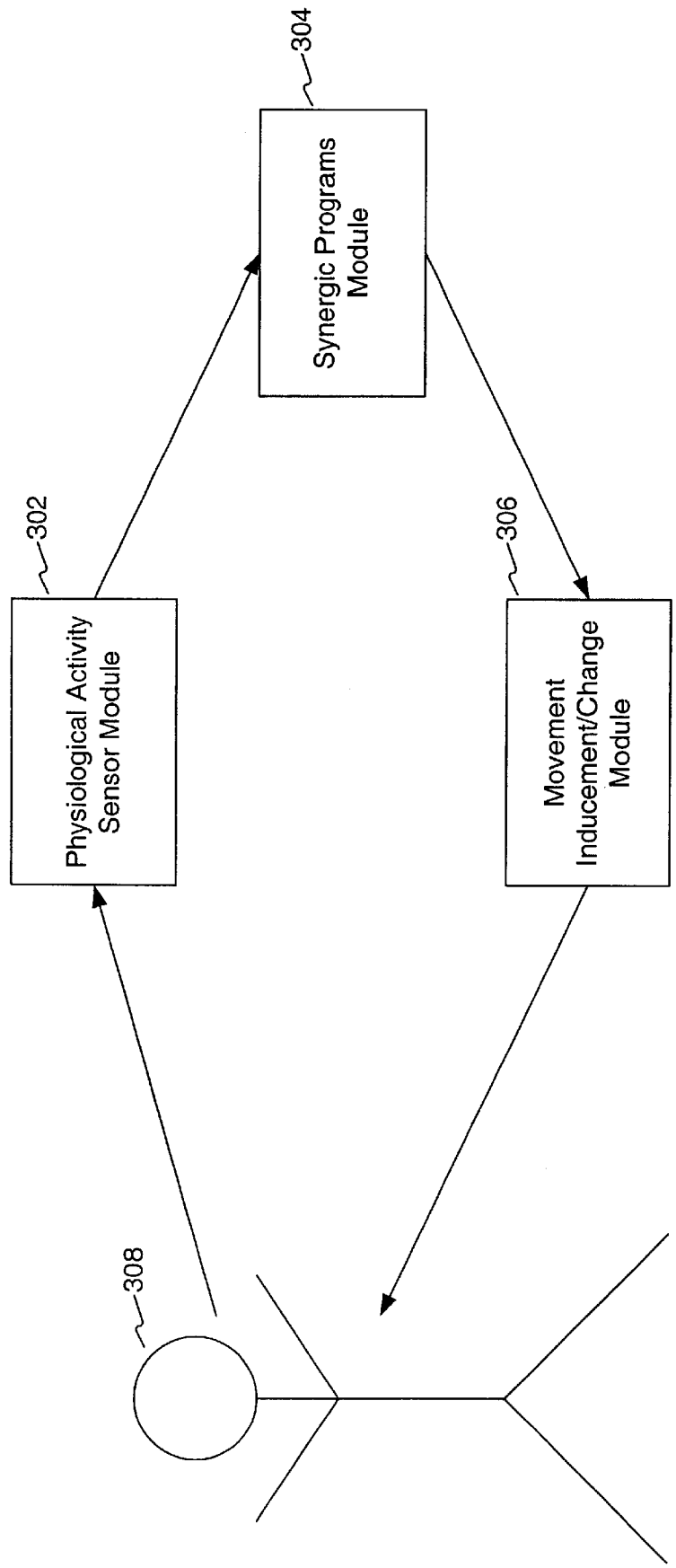
FIG. 3 is a block diagram representing an example operating environment according to an embodiment of the invention.

FIG. 3 is a block diagram representing an example operating environment of the present invention. It should be understood that the example operating environment in FIG. 3 is shown for illustrative purposes only and does not limit the invention. Other implementations of the operating environment described herein will be apparent to persons skilled in the relevant art(s) based on the teachings contained herein, and the invention is directed to such other implementations. Referring to FIG. 3, a physiological activity sensor module 302 (hereafter sensor module 302), a synergic programs module 304 (hereafter programs module 304), a movement inducement/change module 306 (hereafter movement module 306) and a subject 308 are shown.

At a high level, sensor module 302 monitors the physiological activity of subject 308 and receives signals regarding the particular physiological activity it is monitoring. Sensor module 302 processes, preferably in real time (although the invention is not limited to real time processing), the physiological activity signals to derive the necessary information used by programs module 304. Programs module 304 receives this information from sensor module 302 and identifies a program for subject 308 that will direct movements (such as but not limited to motoric) in synergic timed correlation with physiological activity being monitored. Based on the program determined by programs module 304, movement module 306 conveys or triggers the appropriate signal, stimuli or force that will direct the movement (such as but not limited to motoric). Next, each of these modules are described in more detail.

3.1. Physiological Activity Sensor Module

Figure 4:
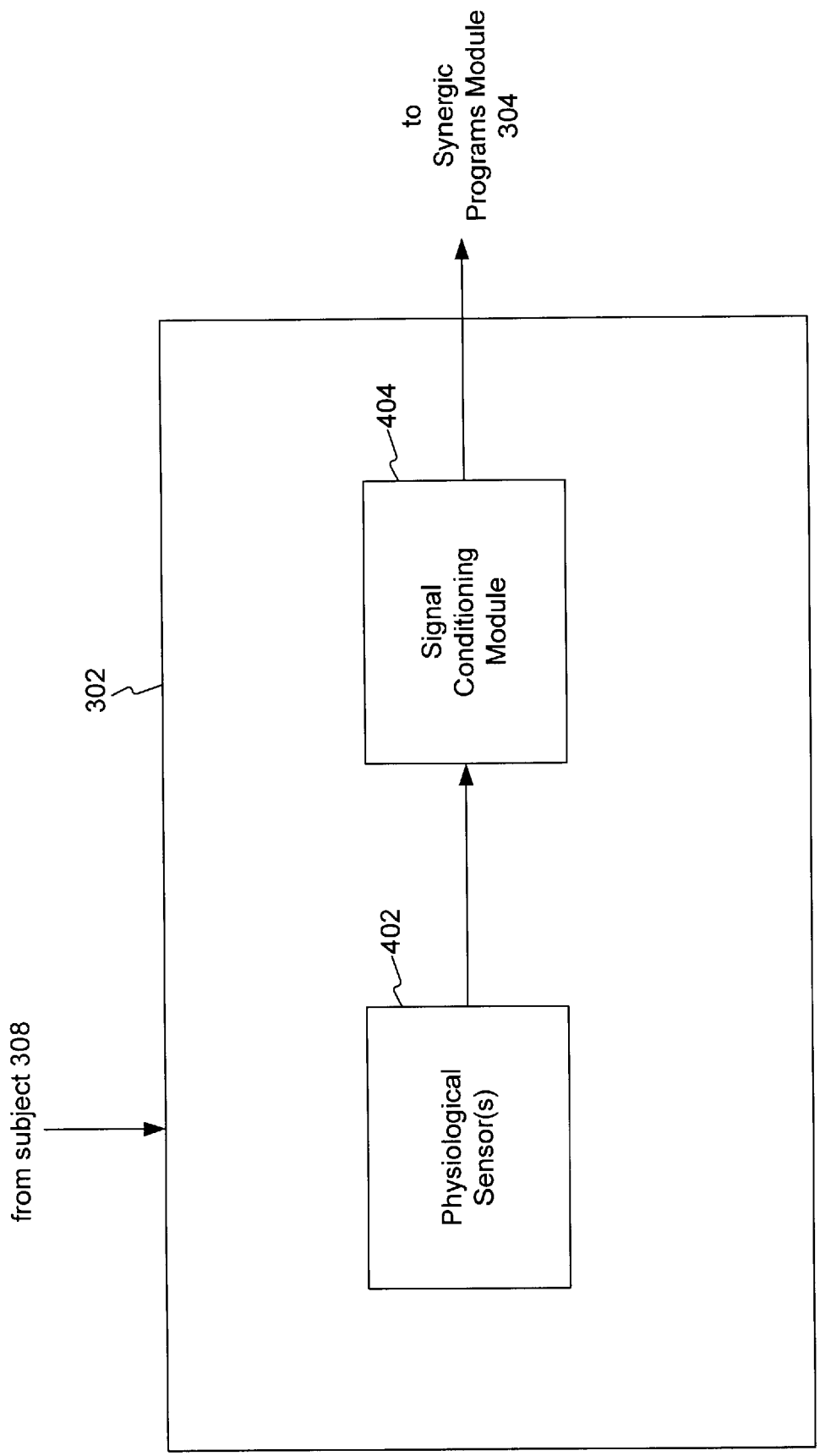
FIG. 4 illustrates a sensor module that includes one or more physiological sensor(s) and a signal conditioning module according to an embodiment of the invention.

As stated above, sensor module 302 monitors a physiological activity of subject 308. Sensor module 302 processes, preferably in real time, the physiological activity signals to derive the necessary information used by programs module 304. Referring to FIG. 4, sensor module 302 is comprised of one or more physiological sensor(s) 402 and a signal-conditioning module 404. Both of these are described in more detail below.

3.1.1. Physiological Sensor

One or more of physiological sensor 402 is utilized for detecting, transducing or deriving signals related to the physiological activity being monitored. Physiological sensors 402 may be comprised of one or more of those currently used in the art, including but not limited to, those used in reography or doppler techniques and/or in photoplethysmography devices to detect the arterial and/or venous pulse, and/or those used to detect changes in galvanic skin resistance and/or those to measure blood pressure, and/or those used to currently detect the ECG or those to detect electrocortical EEG activity and/or those to detect the periodic chest movements due to the breathing activity. Physiological sensors 402 encompass the above examples and also, in general, any other sensors currently existing or to be developed in the future and by which signals representative of physiological activity of the heart and/or brain and/or lungs and/or the autonomic nervous system and/or hormonal activity and/or of any other physiological activities could be directly or indirectly detected. The physiological activity detected by physiological sensor 402 is forwarded to signal condition module 404, which is described next.

3.1.2. Signal Conditioning Module

Signal conditioning module 404 provides preferably real time conditioning and processing of signals produced or derived from the physiological activity being monitored. Signal conditioning module 404 performs a number of well known steps in the relevant art(s) comprising, but not limited by, the steps of amplifying, filtering, multiplexing and converting analog signals to digital signals or vice versa, protocol conversion, etc. The digital signals are then transmitted directly or by wireless means to programs module 304 (FIG. 3). Depending on the particular embodiment, signal-conditioning module 404 may be physically located within programs module 304. It is noted that while the processing of sensor module 302 has been described as operating in real time, in some embodiments such processing does not occur in real time. Next, programs module 304 is described.

3.2. Synergic Programs Module

Figure 5:
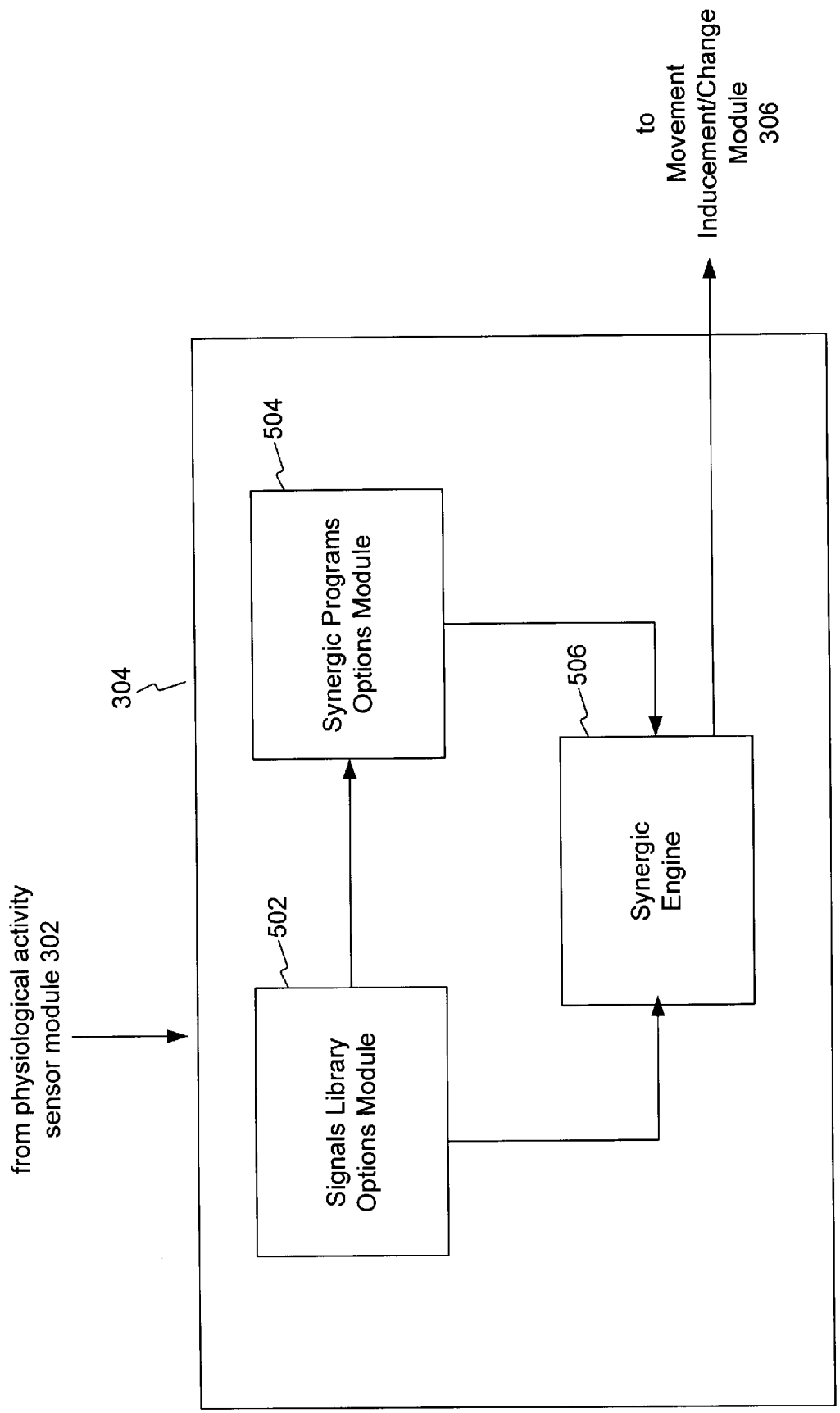
FIG. 5 illustrates a programs module that includes a signals library options module, a synergic programs options module and a synergic engine according to an embodiment of the invention.

Programs module 304 receives information regarding the monitored physiological activity from sensor module 302 and identifies the particular type of program for subject 308 that will direct movements (such as but not limited to motoric) in synergic timed correlation with physiological activity being monitored. Referring to FIG. 5, in an embodiment of the present invention programs module 304 is comprised of a signals library options module 502, a synergic programs options module 504 and a synergic engine 506. Each of these components is described next.

3.2.1. Signals Library Options Module

Signals library options module 502 is a library (such as but not limited to a software or firmware library) of different types of sensorial signals or stimuli, utilized by the present invention to trigger the practice of voluntary correlated movements. The signals are directed to subject 308 in order to i) indicate the subject when to produce the correlated movement and ii) to induce in the subject the phenomena of "renunciation" as explained below. Because this renunciation to cognitive attentional process depends on various conditions of the subject (i.e. literacy, learning disabilities, etc.) several options for the type of signals to be used are provided. As stated above, "synergic timed correlation" relates to monitoring the variability in the cycle of a physiological activity of subject 308 and then inducing subject 308 to perform a movement (such as but not limited to motoric) in a variably timed fashion, such that the temporal variability of the movement is correlated to the temporal variability of the physiological activity, but the timing of the movement never enters into a continuous mode of synchronization or entrainment with the timing of the occurrence of the physiological activity, because the movement contains an extra, additional variability arising from a secondary correlation aimed to facilitate a synergic correlation to take place.

In order for the movement (such as but not limited to motoric) to be performed in a "variably timed fashion" there must be some sort of signal, stimuli or force inducing the movement to occur. As will be described below, synergic engine 506 utilizes signals library options module 502 to determine what signal or stimuli will be used to prompt the performance of the correlated movement. An example snapshot of data that may be stored in signals library options module 502 where subject 308 is voluntarily involved in the practice of correlated movements is shown with reference to FIG. 6.

FIG. 6 illustrates an example table 600 containing sensorial signals and stimuli that prompt subject 308 to voluntary perform a movement. Table 600 is for illustration purposes only and is not intended to limit the present invention.

Table 600 illustrates that the signals or stimuli may be either of the aural type 602 or of the visual type 604. (Although not shown, other types are possible, including but not limited to tactile, heat and pressure types.) For each type, table 600 includes columns indicating group classification 606, main features 608, examples 610, quantity of group members 612, particular features for randomization 614 and global number of random changes 616. Particular features for randomization 614 are further broken down into three columns including type/example 618, partials 620 and total options 622. It should be remarked that main feature 608 shows few examples among many others that are also possible and that the roman numbers for group classification 606 are arbitrary. Quantity of group members 612 and type/example 618 of particular features of randomization 614 are also arbitrary and that other possibilities can be considered. Nevertheless, there is an underlying basic concept in this table, which consists in providing sets of signals, and stimuli, which could be perceived and/or grasped and/or understood by the subject in accordance to his/her perceptual/cognitive capabilities.

Table 600 is an example, but only generally applicable for people considered to be normal and older than 8 years of age (and of course FIG. 6 is provided for example purposes only and other tables would be applicable to other persons of other given ages and/or limitations). A child 6 years old cannot grasp or understand for example, the differences between 12 different geometrical forms (Group I) or 26 different letters (Groups III and IV), and therefore the desired process of "renunciation" will not take place. Similarly, four different lines structures and two different thickness for drawing the geometric forms could be too many variations to be grasped by a child suffering for example of learning disabilities. Signal library options 502 will contain libraries adapted for different levels of literacy, cognitive processing and perceptual capabilities. The total option column 622 is obtained by multiplying the numbers for each particular feature like 4 types of lines and 2 types of thickness giving a total variety of 8. Column 616 is calculated by multiplying the values of column 622 and 612 first and then by 108 for visual types and by 9 if for aural types of signals. Twelve colors, 3 brightness levels and 3 sizes give a total number of 108 possibilities (12×3×3) for visual signals and similarly is obtained the 9 possibilities for aural signals. It should again be remarked that for small children of 6 to 8 years old, the global number of random changes (column 616) will be significantly lower than those shown in Table 600.

An example of visual type 604 is illustrated in table 600 by row 626. The group classification 606 is "I", the main feature 608 is "two dimensional geometric forms" and examples 610 include "≡" and "Δ". The quantity of group members 612 is "12". As stated above, randomization of the signals or stimuli facilitates renunciation by subject 308. Here, the particular features for randomization 614 include "line structure" and "line thickness" for type/example 618, "4" and "2" for partials 620 and "8" for total options 622. Finally, the global number of random changes 616 is "10,368" for row 626 (12×8×108).

An example of aural type 602 is illustrated in table 600 by row 630. Here, the group classification 606 is "I" and the main feature 608 is "vowels". Examples 610 include "a", "e", "i", "o" and "u". Therefore, the quantity of group members 610 is "5". Finally, the global number of random changes is "45" (5×9).

Table 600 also illustrates the general random features 624 of visual type 604 and aural type 602. The general random features 624 of visual type 604 is "108". The general random features 624 of aural type 602 is "9".

As stated above with reference to voluntary involvement by subject 308, when attention to sensorial indicia or signals is required, each successive indicia is made to change in a random or a quasi-random fashion, therefore making it almost impossible for the subject to predict what the next indicia will be, when the next indicia will occur, or from where the next indicia will emanate driving the cognitive attentional mechanisms of subject 308 towards a relaxation state. The result is that the cognitive mechanisms of subject 308 can be induced to give up and relax (i.e., subject 308 renounces to engage in cognitive attentional processes related to the signals), thus increasing the probability for the existence of synergic timed correlation between the monitored physiological activity and the movement of subject 308. Synergic programs options module 504 is described next.

3.2.2. Synergic Programs Options Module

Synergic programs options module 504 is software or firmware of various programs and methods including options for different signals stimuli or forces, which can be utilized for the practice of correlated movements. These programs and methods indicate what type of movements (either of the voluntary or involuntary involvement type) and which type of signals stimuli and/or force may be used in order for subject 308 to practice the correlated movements of the present invention. Section 6.2 below describes in detail the types of information that is stored in synergic programs options module 504.

3.2.3. Synergic Engine

Synergic engine 506 receives inputs from signals library options module 502, synergic programs options module 504 and physiological activity sensor module 302. The administrator and/or an expert system within the synergic program module 304 or directly within synergic engine 506 then determines (1) what type of signal, stimuli or force should be used to trigger the movement, (2) one or more of the synchronization timings to trigger the signal, stimuli or force like if during systole and/or diastole (or primary correlation), (3) the timing fluctuation program (or secondary correlation), and (4) the types of movement itself in order for subject 308 to practice the correlated movements of the present invention. The synchronization timing of the primary correlation is based on the monitored physiological activity of subject 308. Synergic engine 506 provides input to movement module 306 regarding the determined signal, stimuli or force that will be used to trigger subject 308 and all the timings of the trigger.

Timings of these signals, stimuli or forces for the primary and secondary correlations may be randomized or preselected. The boundaries for the timings of primary correlations are given by the extent of the time cycle of the selected physiological activity as well as by the extent and time location of the sub-intervals in which the cycle is considered to be divided. The time boundaries for the secondary correlations are given by the extent of the said sub-intervals, the magnitude of the fluctuations assigned to selected time periods within the sub-interval in which signals, stimuli or force will induce or produce the synergic movements, as well as the maximum number of physiological cycles at which the following signal, stimuli or force may come up in order to induce or produce the synergic movement. All the time series of events resulting from the secondary correlations can be obtained by random and/or by preselected mathematical series modes. As noted above, in an embodiment such variability is based on one or more variables. For example, if such variability is represented by V, then V can be represented as follows (although four variables are shown in the following example, in practice any number of variables could be used to represent V):

$$V=A+B+C+D$$

Each variable can be arbitrarily established, or can be established by any random or mathematical function. For example, the value of variable A can be determined according to any random or mathematical function, or can be arbitrarily established, or can be otherwise set.

Each variable can itself be based on any number of variables. For example, variable A can be represented as follows (although four variables are shown in the following example, in practice any number of variables could be used to represent A):

$$A=A1+A2+A3+A4$$

Each of these variables can be arbitrarily established, or can be established by any random or mathematical function.

The above operation of the invention can be extended to any level. Thus, for example, any of variables A1, A2, A3, and/or A4 can be based on any number of variables, and any of those variables can be arbitrarily established, or can be established by any random or mathematical function.

This preselected mathematical series can take any form.

According to each particular embodiment and/or each subject's particular case, experience and/or experimental research will determine the best mathematical modes as well as the best primary and secondary correlation mode as well as the best type of movements to be recommended for each case. The following Table 2 builds on Table 1 above and includes the distinctions between the type of body parts involvement and an example for modes of physiological sub-cycle or primary correlation. Type of body parts involvement relates to the number of body parts involved in the correlated movement. Voluntary correlated movement can be practiced by utilizing one or more parts of the human body. In an embodiment of the present invention, multiple correlated movement consists in the correlation, with an intrinsically varying physiological activity, of one or more muscle groups and/or muscle joint groups movements of at least two main anatomical parts into which the human body is divided. For example, multiple correlated movements may take place by coordinating eye(s)-hand or hand-hand or leg-leg, eye-leg, etc., movements, with physiological activity.

The mode of physiological sub-cycle correlation relates to the time interval during the cycle of the physiological activity that the movement will be prompted, including in either the early cycle (M1) or the late cycle (M2). M1 and M2 represent two examples for modes of timing a movement within a sub-cycle of physiological activity of subject 308. The invention is not limited to this example because more than two sub-cycles could be considered. Furthermore, the movement may be timed to occur in any portion of sub-cycles M1 and/or M2, or outside of M1 or M2, or in any case the placement of the movement may be specified. As it is well known in the art, the heart and respiratory cycles, for example, can be divided in more than two periods of physiological significance. Synergic timed correlations can be established with all of them. Table 3 illustrates the timing of the signals, stimuli or force, either pre-selected or randomized for type of body parts and modes of primary correlation. Tables 2–3 are for illustration purposes only and are not intended to limit the present invention.

TABLE 2

Distinction Between Both Type of Body Parts Involvement and the Mode of Physiological Sub-Cycles Primary Correlation

| Class | Sub-class | Type Body parts Involvement | Example Modes for sub-cycles of Physiological activity (primary correlation) |
|---|---|---|---|
| Voluntary | Active Reactive | Unitary (U) | Early Cycle (M1) |
| Involuntary | Reflexive Passive | Multiple (M) | Late Cycle (M2) |

TABLE 3

Program Sequence

| Of Types | | Of Modes | |
|---|---|---|---|
| Pre-selected | Randomized | Pre-selected m1 and/or m2 | Randomized m1 & m2 |

Table 4 illustrates various unitary types of movements that may be executed by the subject while practicing the present invention.

TABLE 4

Unitary Types of Movements

| Body Part | Movement Specification |
|---|---|
| Eyebrows | Surprise |
| Face | Smile |
| Eyes | Left-right; up-down |
| Head | Rotation; left-right |
| Head | Flexion, up-down |
| Vocal cords | Vowels vocalization |
| Arm | Front-back; up-down |
| Forearm | Left-right; up-down |
| Hand | Handgrip |
| Hand | Rotation; left-right |
| Hand | Flexion; up-down |
| Thumb | Rotation; flexion; opposition; taping |
| Finger | Rotation; flexion; taping |
| Upper leg | Up; inside-outside |
| Leg | Inside-outside; extension-flexion |
| Foot | Inside-outside; up-down |
| Toe | Up-down; rotation |

Synergic engine 506 should be understood in its broader sense to be a programmable machine. Synergic engine 506 may perform high speed processing of data. Therefore, synergic engine 506 may involve a micro-controller, a microprocessor, a specially programmed machine incorporating instructions in ROM, PROM or other firmware, a specially programmed machine incorporating instructions, which are hardwired in, or a general-purpose computer together with a computer program. This computer program may have many forms including but not limited to an entertainment program, an interactive game program or an informative communication program.

In fact, synergic engine 506 could be implemented using one of more of the computer systems described next with reference to FIG. 28. The computer system 2800 includes one or more processors, such as processor 2804. The processor 2804 is connected to a communication bus 2806. Various software embodiments are described in terms of this example computer system. After reading this description, it will become apparent to a person skilled in the relevant art how to implement the invention using other computer systems and/or computer architectures.

Computer system 2800 also includes a main memory 2808, preferably random access memory (RAM), and can also include a secondary memory 2810. The secondary memory 2810 can include, for example, a hard disk drive 2812 and/or a removable storage drive 2814, representing a floppy disk drive, a magnetic tape drive, an optical disk drive, etc. The removable storage drive 2814 reads from and/or writes to a removable storage unit 2818 in a well-known manner. Removable storage unit 2818, represents a floppy disk, magnetic tape, optical disk, etc. which is read by and written to by removable storage drive 2814. As will be appreciated, the removable storage unit 2818 includes a computer usable storage medium having stored therein computer software and/or data.

In alternative embodiments, secondary memory 2810 may include other similar means for allowing computer programs or other instructions to be loaded into computer system 2800. Such means can include, for example, a removable storage unit 2822 and an interface 2820. Examples of such can include a program cartridge and cartridge interface (such as that found in video game devices, video camcorder, and so forth), a removable memory chip (such as an EPROM, or PROM) and associated socket, and other removable storage units 2822 and interfaces 2820 which allow software and data to be transferred from the removable storage unit 2818 to computer system 2800.

Computer system 2800 can also include a communications interface 2824. Communications interface 2824 allows software and data to be transferred between computer system 2800 and external devices. Examples of communications interface 2824 can include a modem, a network interface (such as an Ethernet card), a communications port, a PCMCIA slot and card, etc. Software and data transferred via communications interface 2824 are in the form of signals 2826 which can be electronic, electromagnetic, optical or other signals capable of being received by communications interface 2824. These signals 2826 are provided to communications interface via a channel or path 2828. This channel 2828 carries signals 2826 and can be implemented using wire or cable, fiber optics, a phone line, a cellular phone link, an RF link and other communications channels.

In this document, the terms "computer program medium" and "computer usable medium" are used to generally refer to media such as removable storage device 2818, a hard disk installed in hard disk drive 2812, and signals 2826. These computer program products are means for providing software to computer system 2800.

Computer programs (also called computer control logic) are stored in main memory and/or secondary memory 2810. Computer programs can also be received via communications interface 2824. Such computer programs, when executed, enable the computer system 2800 to perform the features of the present invention as discussed herein. In particular, the computer programs, when executed, enable the processor 2804 to perform the features of the present invention. Accordingly, such computer programs represent controllers of the computer system 2800.

In an embodiment where the invention is implemented using software, the software may be stored in a computer program product and loaded into computer system 2800 using removable storage drive 2814, hard drive 2812 or communications interface 2824. The control logic (software), when executed by the processor 2804, causes the processor 2804 to perform the functions of the invention as described herein.

In another embodiment, the invention is implemented primarily in hardware using, for example, hardware components such as application specific integrated circuits (ASICs). Implementation of the hardware state machine so as to perform the functions described herein will be apparent to persons skilled in the relevant art(s). In yet another embodiment, the invention is implemented using a combination of both hardware and software. Movement module 306 is described next.

3.3. Movement Inducement/Change Module

Figure 7:
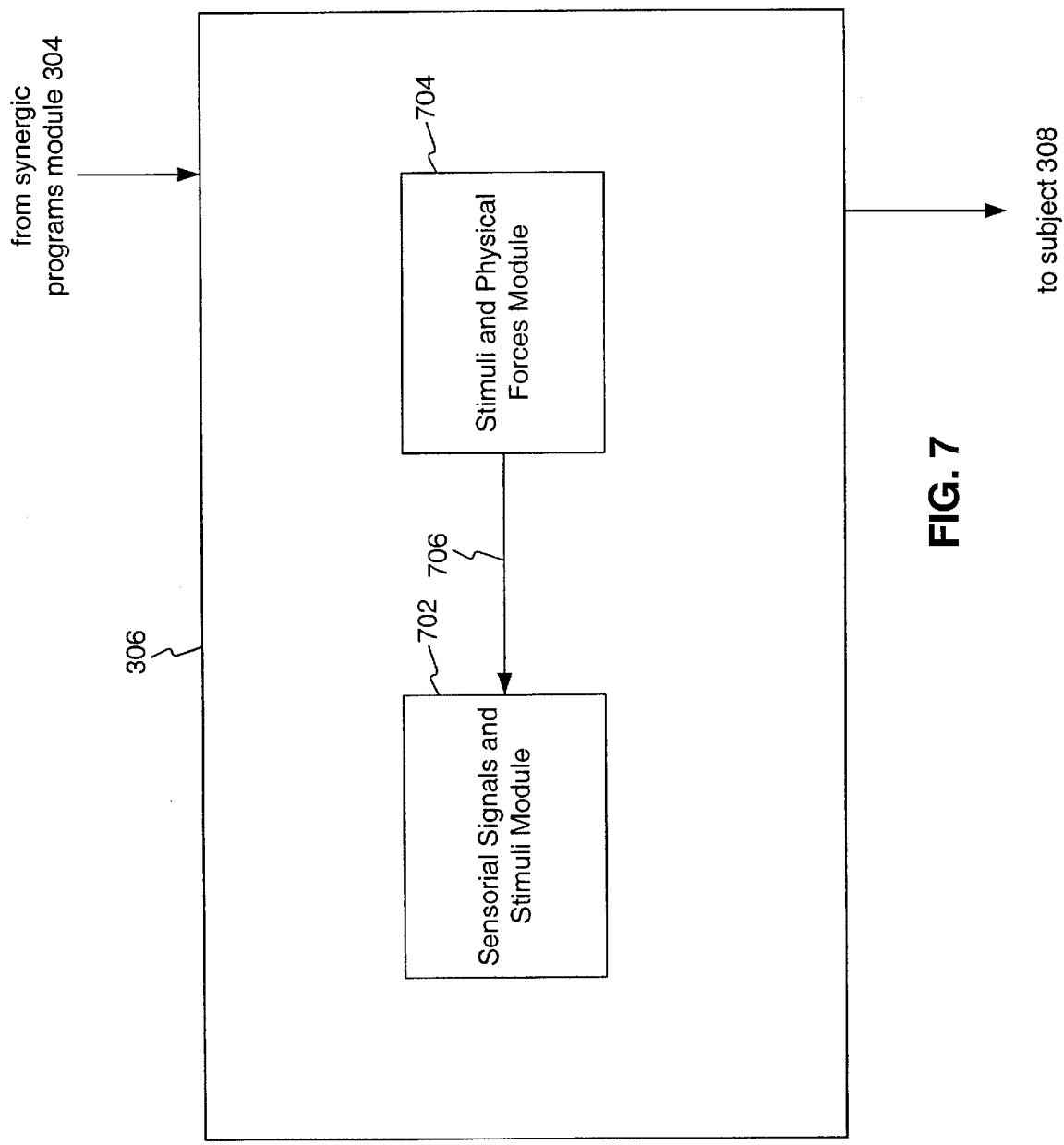
FIG. 7 illustrates a movement inducement/change module that includes sensorial signals and stimuli module as well as stimuli and physical forces module according to an embodiment of the invention.

Movement module 306, controlled by synergic program module 304, conveys the appropriate signal, stimuli or force to subject 308 that will direct the movement (such as but not limited to motoric). As shown in FIG. 7, movement module 306 is comprised of sensorial signals and stimuli module 702 and stimuli and physical forces module 704.

In an embodiment of the present invention, sensorial signals and stimuli module 702 is a computer (such as that shown in FIG. 28, for example) that produces and controls source generators of sensorial signals or stimuli. In an embodiment of the present invention, stimuli and physical forces module 704 is a computer that controls a generator of physical forces aimed to induce movements or change the state of movement on all the body or in any of its parts, as well as in the signal and/or stimuli generator. Note that arrow 706 indicates a relative movement force where stimuli and physical forces module 704 causes sensorial signals and stimuli module 702 to be physically moved in an embodiment of the invention.

As will be described below in FIG. 8, sensorial signals and stimuli module 702 is utilized in the voluntary/active involvement embodiment of the present invention. Likewise, as described below with reference to FIG.9, stimuli and physical forces module 704 is utilized in the voluntary class, reactive subclass involvement embodiment of the present invention. Finally, as described below with reference to FIG. 10, stimuli and physical forces module 704 is utilized in the involuntary class, passive and reflexive subclasses involvement embodiments of the present invention. These embodiments are discussed herein for illustrative purposes only and are not meant to limit the present invention. In this invention, physical forces include, but are not limited to, those of mechanical, electromechanical, cohesional, elastical, frantational, electrostatical, electrical, magnetical, electromagnetical, and centrifugal character.

4. System Architecture—Voluntary Class Involvement

In an embodiment of the present invention, for the conscious/voluntary involvement of the correlated movement, the point in time that the movement is prompted may be given by one or more of: (1) sensorial indicia by way of a selected set of signals and/or stimuli produced and controlled by the apparatus of present invention; (2) specific rules that subject 308 has learned; and (3) efforts to keep the body at balance and in physical equilibrium at any medium within a gravitational field and/or to maintain the body's motor coordination, when the total body or any of its parts is directly or indirectly subjected to inertial or any other forces produced and controlled by the apparatus of the present invention. The above are provided for purposes of example and do not limit the invention.

During the execution of voluntary correlated movement, the mechanisms of attention of subject 308 can be driven away from their natural cognitive attentional involvement, and be bound instead to follow only an "internal-physiological timing automatism", which is of a lower cognitive attentional level. As described above, this is referred to by the present invention as renunciation by subject 308. With the present invention, attention mechanisms of subject 308 are driven towards looking "inwards" (i.e., to the intrinsically varying physiological activity) and not "outwards" (i.e., to the environmental changes). For example, each successive signal or indicia is made to change at random (or, alternatively, as pre-selected), making almost impossible for subject 308 to predict what the next signal or indicia will be, when the next signal or indicia will occur, or from where the next signal or indicia will emanate therefore driving cognitive attentional mechanisms to renounce attaining knowledge about the signals which will result in an increased relaxation state in subject 308. To facilitate this process, signals are as far as possible from emotional content in relation to subject 308.

The voluntary class is subdivided into two subclasses, including active and reactive. The active subclass is described next with reference to FIG. 8. Following, the reactive subclass is described with reference to FIG. 9.

4.1. Active Subclass

Figure 8:
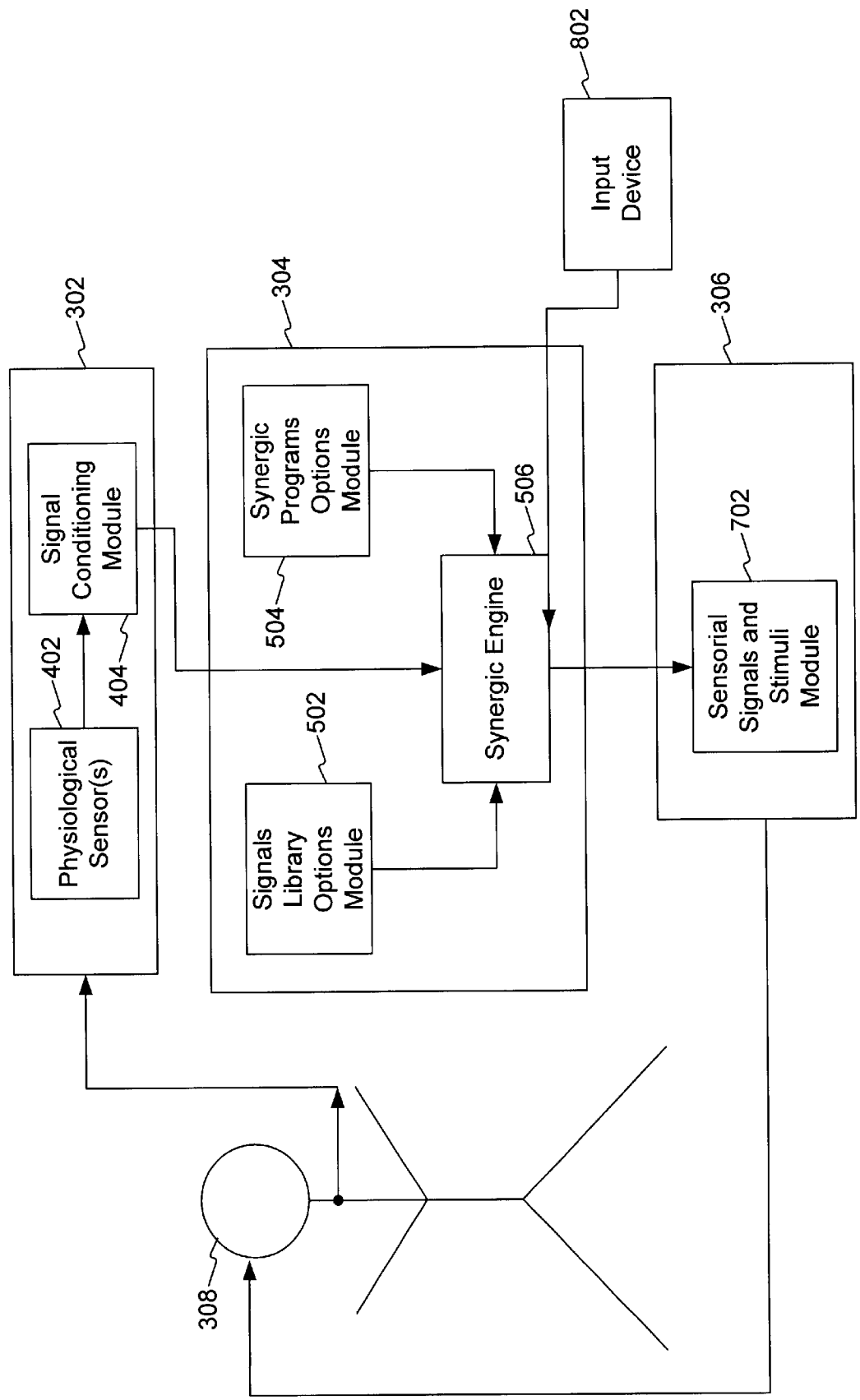
FIG. 8 illustrates an example operating environment of the voluntary class, active subclass involvement embodiment of the present invention.

FIG. 8 is a block diagram representing an example-operating environment of the present invention where subject 308 is required to have active voluntary involvement in the correlated movement. In FIG. 8, subject 308; physiological sensor 402 and signal conditioning module 404 of physiological activity sensor module 302; signals library options module 502, synergic programs options module 504 and synergic engine 506 of synergic programs module 304; an input device 802 and sensorial signals and stimuli module 702 of movement inducement/change module 306 are shown.

For illustration purposes only, it is assumed that physiological sensor 402 is an ECG machine from where the heart cycle of subject 308 can be monitored. In addition, it is assumed that indicia or signals from sensorial signals and stimuli module 702 is comprised of visual signals displayed on a screen. In this embodiment, the indicia generated at sensorial signals and stimuli module 702 can be optionally correlated with either the early portion of the heart contraction cycle (M1 from Table 2 above) or with the late portion of the heart contraction cycle (M2 from Table 2), or any portion thereof (as determined by the invention). By non-invasively monitoring (e.g., the arterial pressure wave on the carotid, sub-clavia or radial artery) it can be directly shown the subject's systolic and diastolic phases of the heart cycle. This can also be done non-invasively with piezo-electric sensors. Also by photopletismographic transducer methods the subject's pulse can directly be obtained and thereby monitor systolic and diastolic phases of the heart cycle.

The ECG does not directly show the early and late portions of the heart contraction cycle, known under the names of mechanical systole and mechanical diastole. Nevertheless they can be obtained with sufficient approximation for the purpose of some embodiments of this invention, by way of a mathematical function depending only upon the gender and mean heart rate of the subject. The above mathematical functions were obtained from data on large sample groups. The main electrical ECG events characterizing the heart function are shown in FIG. 15B. The QRS complex shows the ventricular depolarization, the Pwave, the depolarization of the atria, and the Twave the repolarization of the ventricules. The pre-ejection period (PEP) goes from the Q point in the ECG until few tens of milliseconds behind the S point in the ECG. The end of PEP marks the start of the mechanical systole of the ventricules (MS), and the MS ends around the end of the Twave. The mechanical diastole of the ventricules starts where MS ends and ends in the next Q point, after the P wave. Expressions defining the three main sub-cyles of the ventricular or heart cycle are given below, as a function of gender (M or F) and the mean heart rate (mHR), as shown below in Table 5.

TABLE 5

Sub-Cycles length (msc) of the Heart Period as a function of Heart Rate (HR) in beats/min

| Sub-Cycle | Man | Women |
| --- | --- | --- |
| Left ventricular Ejection Time or Mechanical Systole (MS)* | 413 - 1.7 HR | 418 - 1.6 HR |
| Pre-ejection Period (PEP) | 131 - 0.4 HR | 133 - 0.4 HR |
| Refilling of Left Ventricle or Mechanical Diastole (MD) | 2.1 HR + 6x $10^4$/ HR - 544 | 2 HR + 6x $10^4$/ HR - 551 |

Obtained from 121 Man and 90 Women by:
  Weissler et al, Bedsides techniques for the evaluation of ventricular function in man. Amer J. Cardiol 23:577, 1969.
  Weissler et al, Systolic time intervals in heart failure in man, Circulation 37:149,1968.

Methodological, technological and economic considerations in relation to each particular embodiment will indicate the system to be followed in order to monitor the sub-cycles of visceral periodical function. In addition, synergic programs options module 504 can decide to either pre-select or randomize a chosen sequence of correlated movements like those shown in Table 4.

It is also assumed that subject 308 is previously instructed to practice, for example, a handgrip type of correlated movement, as simultaneously as possible with the start and end of an aural signal and/or of the visual signal perceived on the screen. Additionally or alternatively, the need to execute a handgrip type of correlated movement can be also shown to the subject in the screen via input device 802 like for example, a keyboard. Operation of the embodiment of FIG. 8 is further described below with reference to FIGS. 12A and 12B. Other examples of active correlated movement are given below with reference to FIGS. 17–21 where specific tools utilized to practice the present invention are described. The reactive subclass of the voluntary involvement embodiment of the present invention is described next.

4.2. Reactive Subclass

Figure 9:
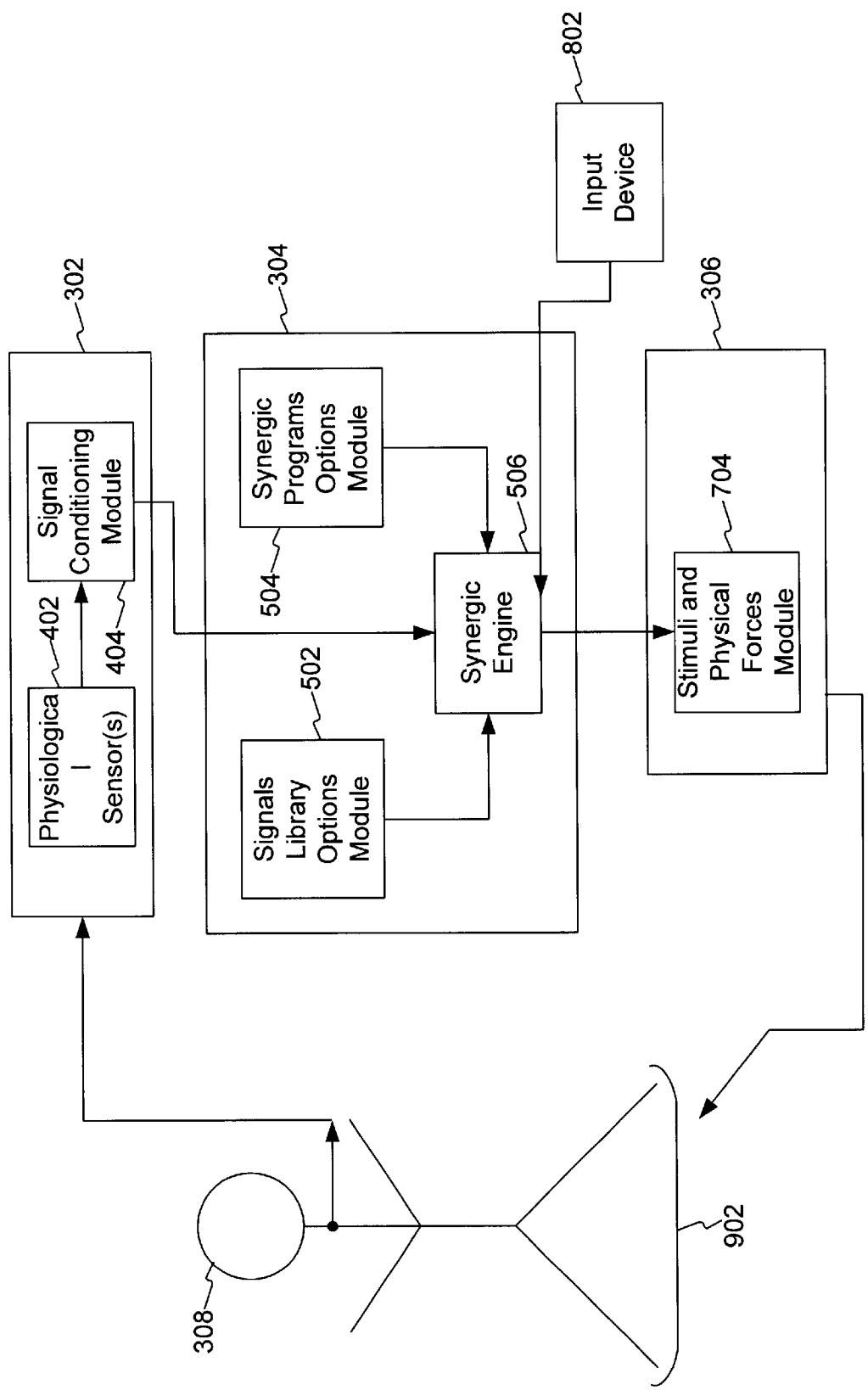
FIG. 9 illustrates an example operating environment of the voluntary class, reactive subclass involvement embodiment of the present invention.

FIG. 9 is a block diagram representing an example operating environment of the present invention where subject 308 is required to have reactive voluntary involvement in performing the correlated movement of the present invention. In FIG. 9, subject 308, physiological sensor 402 and signal conditioning module 404 of physiological activity sensor module 302, signals library options module 502, synergic programs options module 504 and synergic engine 506 of synergic programs module 304, input device 802, stimuli and physical forces module 704 of movement inducement/change module 306 and platform 902 are shown. An example of the reactive subclass is similar to the active subclass described above, except subject 308 is required to react to a physical force, such as a change (increase or decrease) in the resistance of an exercise bike or the increased or decreased speed of a treadmill (represented as platform 902). This requires a voluntary adaptation to intermittent changes in spatial and/or temporal bio-motoric conditions. Here, through input device 802 may consist of a keyboard, different option could be entered in modulus 504 regarding timings as well as changes in resistance or speed. Other examples of reactive correlated movement are given below with reference to FIGS. 22 and 30 where specific tools utilized to practice the present invention are described. Operation of the embodiment of FIG. 9 is described below with reference to FIGS. 12A and 12B. .5. System Architecture—Involuntary Class Involvement In an embodiment of the present invention for the involuntary involvement of the correlated movement, the present invention produces and/or controls physical forces and/or stimuli capable of influencing all the body or any of its parts in order to induce one or more of the following: (1) synergic movements when subject 308 is in a passive condition, and/or (2) synergic movements triggered by the body's reflexive neural mechanisms and/or by other physiological adaptations or processes.

In contrast to the voluntary involvement embodiments of the present invention, in which attentive or cognitive mechanisms are introduced but automatically decreased or eliminated soon later by resorting to a methodology which brings about the phenomena of renunciation as described earlier, in the involuntary involvement embodiment of the invention, attentive and cognitive mechanisms are either not introduced, or are minimally introduced. In the involuntary class, attention and cognitive processing are reduced to a minimal level resulting from minimal body awareness associated to sensorial inputs coming mainly from one or more of touch, pressure, heat and propioceptive neural pathways. The involuntary class is subdivided into two subclasses, including passive and reflexive. Both the passive and reflexive subclass are described below with reference to FIG. 10.

5.1. Passive Subclass

Figure 10:
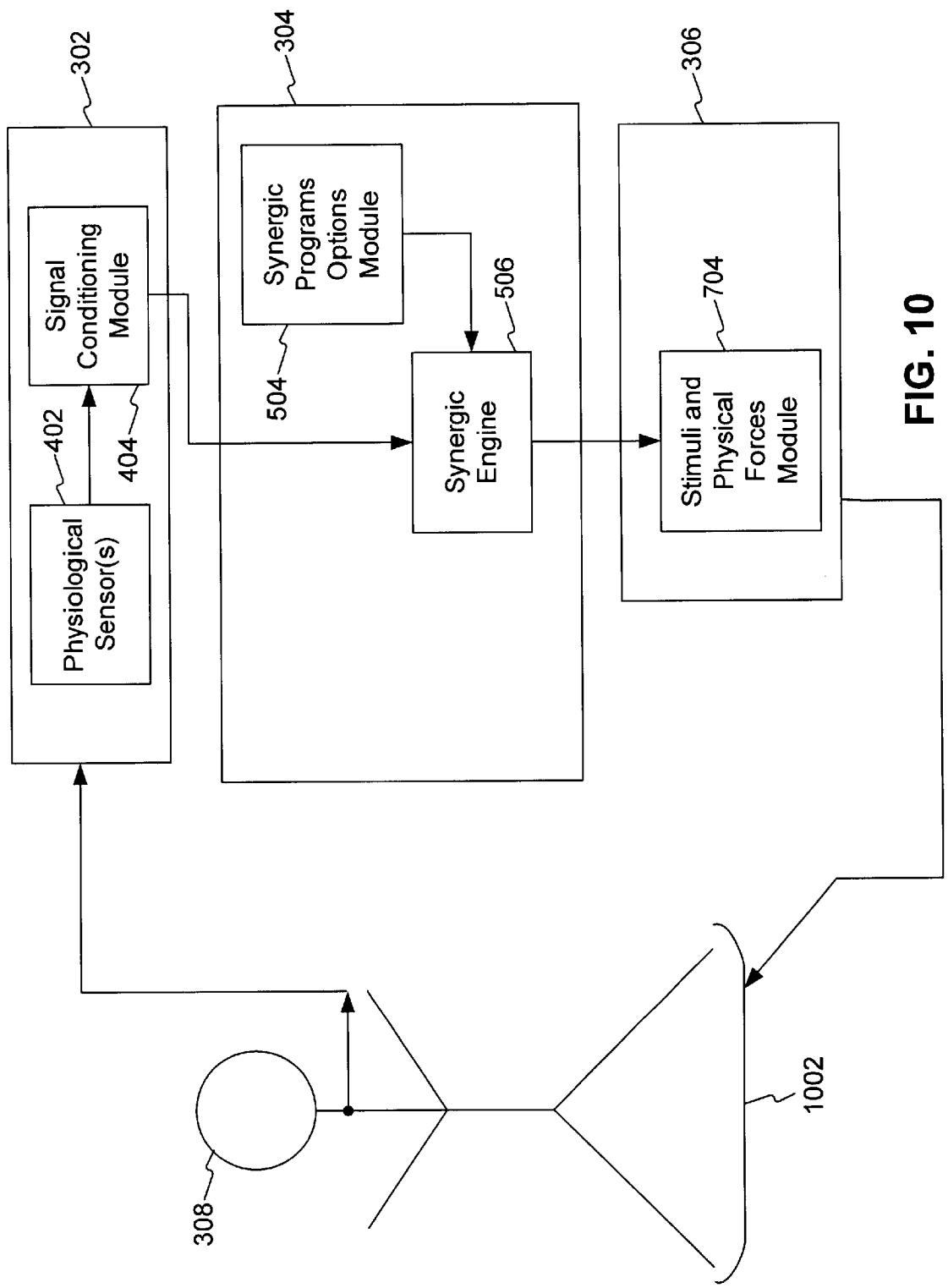
FIG. 10 illustrates an example operating environment of the involuntary class, passive and reflexive subclasses involvement embodiment of the present invention.

FIG. 10 is a block diagram representing an exemplary operating environment of the present invention where subject 308 is engaged in passive involvement in the correlated movement of the present invention. In FIG. 10, subject 308; physiological sensor 402 and signal conditioning module 404 of physiological activity sensor module 302; synergic programs options module 504 and synergic engine 506 of synergic programs module 304; stimuli and physical forces module 704 of movement inducement/change module 306 and platform 1002 are shown. Signals library options module 502 is not generally required for the involuntary class. An example of passive correlated movement includes an intermittent rocking (via, for example, a rocking chair represented as platform 1002) of subject 308 in one or more timed correlation with specific sub-cycle of cyclical physiological activity. There is no input or active participation required by subject 308. Examples of passive correlated movement are given below with reference to FIG. 23 where specific tools utilized to practice the present invention are described. Operation of the embodiment of FIG. 10 is described below with reference to FIGS. 12A and 12B.

5.2. Reflexive Subclass

FIG. 10 also illustrates the reflexive subclass embodiment of the present invention. Like the passive subclass, there is no input or active participation required by subject 308. The correlated movement results from the natural physiological mechanisms of subject 308 resulting, for example, from physical stimuli such as tickling or from physical forces such as a sudden increase or decrease of temperature on all or part of the body surface. Other examples of reflexive correlated movement are given below with reference to FIGS. 24–27, 31 and 32 where specific tools utilized to practice the present invention are described.

6. Operation of the Present Invention 6.1. High Level Operation of the Invention: Obtaining Synergic Timed Correlation Between Physiological Activity and Movements FIG. 14 is a flowchart illustrating the high level operation of an embodiment of the present invention to obtain synergic timed correlation between physiological activity and movements. In FIG. 14, control starts at step 1402. In step 1402, the present invention achieves some level of synchronization of the subject's movement with the naturally variable cycles of physiological activity. This is a first level of time correlation (called here primary correlation) in which the movement is programmed to be done at specific one or more sub-cycles of the intrinsically variable cycle of the chosen physiological activity with which that movement is intended to achieve synergic correlation. Notice that this primary correlation implies synchronization bound to necessarily decrease the time degrees of freedom of the movement, a circumstance not favorable for synergism to be achieved. Nevertheless, this reduction in freedom will be at least partially compensated with a secondary correlation to be shown at step 1404. Notice that the method of inducing renunciation explained more above, upon cognitive attention mechanism, is a compensatory process for the particular case of embodiments to execute synergic voluntary movements, where the subject is bound to follow signals with cognitive and eventual emotional content, aimed to direct those movements. Therefore, in some embodiments the triggering signals or stimuli will necessarily have or generate additional cognitive attention mechanisms and eventual emotional reflexive mechanisms, which are not desirable. In order to neutralize these factors a compensatory method is introduced, leading to renunciation, as more above explained. In all the embodiments of the invention, an absolute time and/or space correlation (synchronization—entrainment and/or complete spatial coordination) are permissible, but only intermittently, during some but not all of the time.

Absolute synchronization (or entrainment) relates to simultaneous lock of main frequency (and/or its harmonics), as well as amplitude lock. Complete spatial coordination relates to zero degree of phase in movement coordination. Control then passes to step 1404.

In step 1404, the present invention assigns an additional and artificial temporal variability to the subject's movement by adding it to the movement after following (in step 1402) the intrinsic temporal variability of the physiological activity, pointing in the direction of enabling the movement to conserve its own level of freedom. This additional temporal variability is achieved by assigning fluctuations to the timings of signals, stimuli or forces taking place during the sub-cycles defined in the step 1402 as well as to the timings of the intervals between one induced movement and the next one. These additional time fluctuations are here designed as secondary correlations, by which a "relative coordination" between physiological activity and the executed or realized movements can then take place and by it to make possible that a state of synergism could be achieved. To achieve synergisms not only some timed correlation among cooperative parts are needed, also some degree of space coordination of movements is required, for which some degree of variety should also be assigned to the executed or realized movements. To achieve that, movements should not be strictly repetitive. For example, more than one type of movement in Table 4 should be executed or realized and/or changes should be introduced in the spatial parameters of the same movement type. The flowchart in FIG. 14 ends at this point. This will be described in more detail below with reference to FIGS. 15 and 16, which illustrate how synergic engine 506 determines the timings of the prompt in order to synergically correlate the movement with the physiological activity of subject 308.

Figure 11:
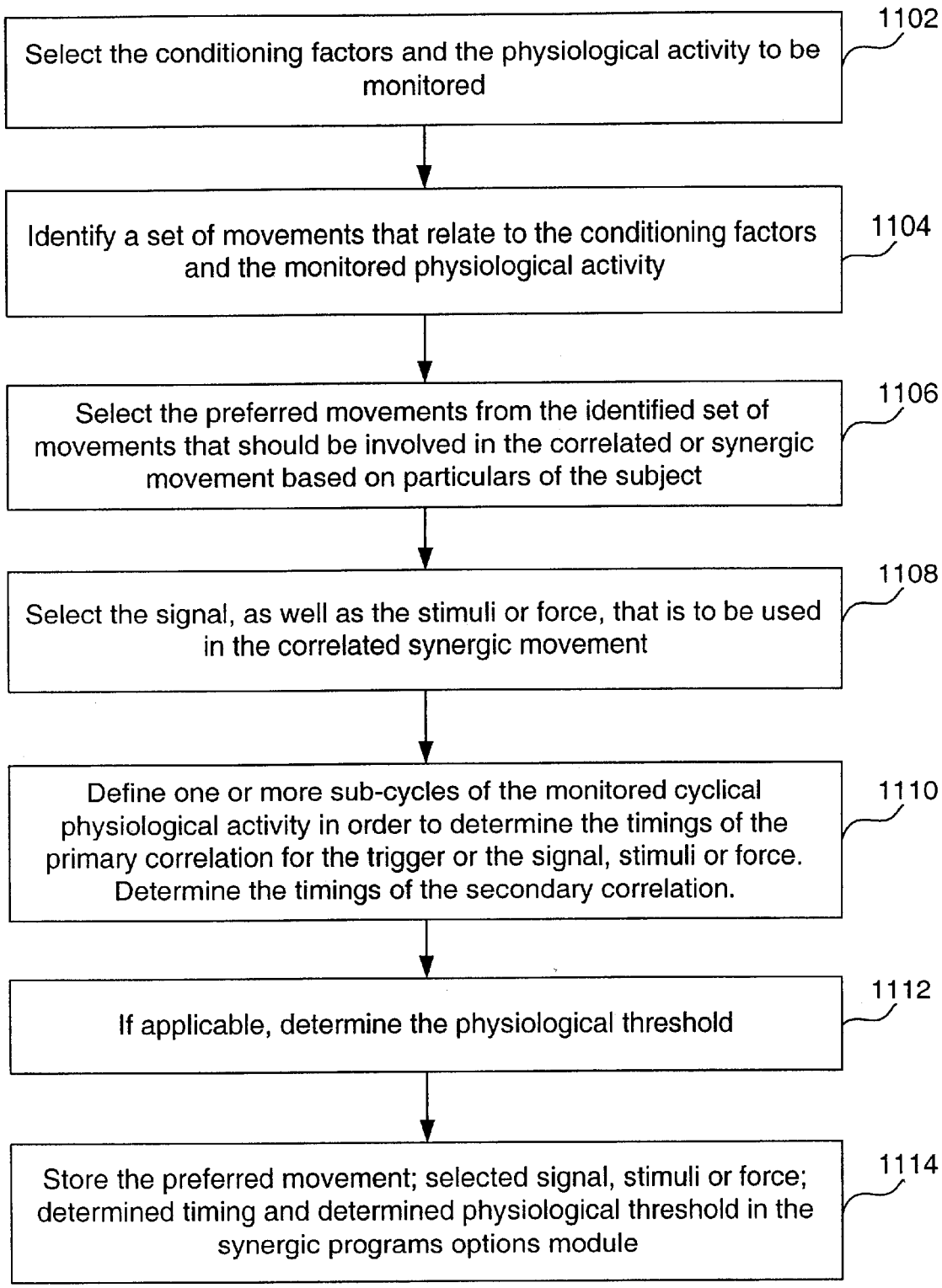
FIG. 11 represents the operation of the invention when developing a program for a particular subject according to an embodiment of the invention.

6.2. Developing a Program for a Subject: Populating Synergic Programs Options Module FIG. 11 is a flowchart that illustrates the operation of an embodiment of the present invention when populating synergic programs options module 504 (FIG. 5). Essentially, FIG. 11 represents the operation of the invention when developing a program for a particular subject 308. In developing this program, a number of factors are first considered (the conditioning factors), such as age group, gender, handedness, dominate/inferior limb, the literacy and physical condition, traits, characteristics, abilities, etc., of subject 308. A plurality of programs may be developed for a particular subject 308.

In FIG. 11, control starts at step 1102. In step 1102, the conditioning factors of subject 308 (FIG. 3) and the physiological activity that is to be monitored are selected. In an embodiment of the present invention, selection in step 1102 of the conditioning factors and physiological activity to monitor has to be approved by an administrator of synergic programs module 304. In this context, the administrator represents a human, synergic engine 506, or some combination of the two, which is currently known as an expert system. As stated above, the physiological activity to monitor may include, but is not limited to, the hormonal cycle, the breathing cycle, the heart cycle and most neurological activity. Control then passes to step 1104.

In step 1104, the administrator and/or module 506 identifies a set of movements from option program module 504 that relate generally to the entered conditioning factors of subject 308 and, to the monitored physiological activity. Age groups are important in the present invention due to the different embodiments of involvement in the correlated and synergic movement of the present invention. For example, a child that is two years of age cannot react to a change in resistance in an exercise bike, or to stimuli envolving letters of the alphabet, in the same way that an adult would react. Control then passes to step 1106.

In step 1106, based on further particulars of subject 308, the administrator and/or modules 506 select the preferred movement/s from the identified set of movements (from step 1104) that should be involved in the correlated movement. Particulars of subject 308 could be, for example, physical, cultural, cognitive, emotional, etc., characteristics of subject 308. For example, consider a touch screen. Even though a typical eight-year old could touch a screen when signaled, this particular tool might not be effective if subject 308 is paralyzed from the waist up.

An embodiment of the present invention is more concerned with gross motoric than with fine motoric movements of subject 308. Gross motoric movements require minimal or no sensorial external attention from subject 308, whereas fine motoric movements engage the high cognitive attentional capabilities of subject 308.

Accordingly, in selecting the preferred movement/s in step 1106, the administrator and/or engine 506 considers the ability of subject 308 to perform the correlated movements as well as their variability and order of execution or realization. The present invention involves the voluntary and/or involuntary (correlated) movements of the subject, resulting in various embodiments of the present invention. As stated above, the voluntary class of envolvement is divided into two subclasses, including active and reactive. The involuntary class of involvement is divided into two subclasses, including passive and reflexive. Control then passes to step 1108.

In step 1108, the administrator and/or synergic engine 506 selects the set of signals from signals library options module 502 and the stimuli or force from the options program modulus 504 that are to be used in the correlated movements. Selection of the set of signals may be made from a table such as that shown in FIG. 6. Again, the particular traits and abilities of subject 308 are considered when performing step 1108. Control then passes to step 1110.

In step 1110, the administrator and/or engine 506 determines the timings of the signal, stimuli or force from modulus 502 and 504 that prompts the subject to perform the movement. In other words, the administrator and/or engine 506 determines the temporal sequence over which the signal, stimuli or force is applied. The timing of the prompt may be dependent on, but is not limited to its synchronization with a particular sub-cycle of the monitored physiological activity or primary correlation, like for example with the early cycle (M1) or the late cycle (M2) of the monitored physiological activity, or any portion thereof, or in some embodiments outside those cycles (as determined by the invention).

The timing of the prompt may also be dependant on whether it is pre-selected or randomized among several possible options. The timings of the primary correlation of the prompt may be determined by taking into consideration when, if attention mechanisms are involved, the preferred movement can be performed by or performed on subject 308 such that there is a minimal taxation in the monitored cyclical intrinsically variable physiological activity (i.e. minimal reduction in its variability). The administrator and/or engine 506 will now define the timings of the secondary correlations. This secondary correlation consists in fluctuations of the starting time and end time defining the duration of signals and/or stimuli and/or forces promoting the movements, as well as in fluctuations in the number of physiological cycles between two successive movements. These fluctuations will be expressed by a series of values. These values can be obtained by using random and/or preselected series. This preselected series can be obtained from any mathematical function, as described herein. There is some experimental evidence that synergism of movement can be associated to simple correlations obeying proportions resulting from the quotient between integer numbers. It follows, that if such discrete quantic correlations are chosen by the administrator and/or engine 506, not any type of mathematical function can be used. Control then passes to step 1112.

The administrator and/or engine 506 may decide to correlate interruptions on the synergic movements being performed to some physiological thresholds being achieved in subject 308. This option will be established at modulus 504. In this case, and at step 1112, synergic engine 506 calculates in real time when that physiological threshold has been reached. Physiological threshold refers to values of physiological variables that may be influenced by the execution of synergic movements like, for example, those reflecting the stress condition of the subject. The administrator and/or engine 506 may decide engagements in synergic movements only inside preselected boundaries of those variables, like between certain values in heart rate, for example. In an embodiment of the present invention, once subject 308 reaches some physiological threshold the correlated or synergy movement is discontinued. Control then passes to step 1114.

In step 1114, the preferred movements (step 1106); selected signal, selected stimuli or force (step 1108); trigger timings (step 1110) for primary and secondary correlations and eventually determined physiological threshold (step 1112) are stored in synergic programs options module 504 to be used in the future with subject 308. The flowchart in FIG. 11 ends at this point.

FIG. 11 represents pre-determining and pre-storing a particular program for subject 308 for future use. FIG. 11 could be executed multiple times to develop multiple programs for subject 308.

Alternatively, the program could be determined on-the-fly by synergic engine 506. Indeed, in that case the expert system will depend almost entirely on programs stored at modulus 502, 504, 506 and with little dependence on decisions of the human administrator, programs can be executed on the fly, in real time, by modulus 304. Extensive use of embodiments of this invention, accumulated data and eventual experimental research with these new tools, will permit the attainment of automated "on-the-fly" synergic programs. In the case where the expert system is performing the operations described above, the expert system performs the steps of FIG. 11. Although, in other embodiments the expert system operates according to other methods.

6.3. Executing a Program for a Subject

Figure 12A:
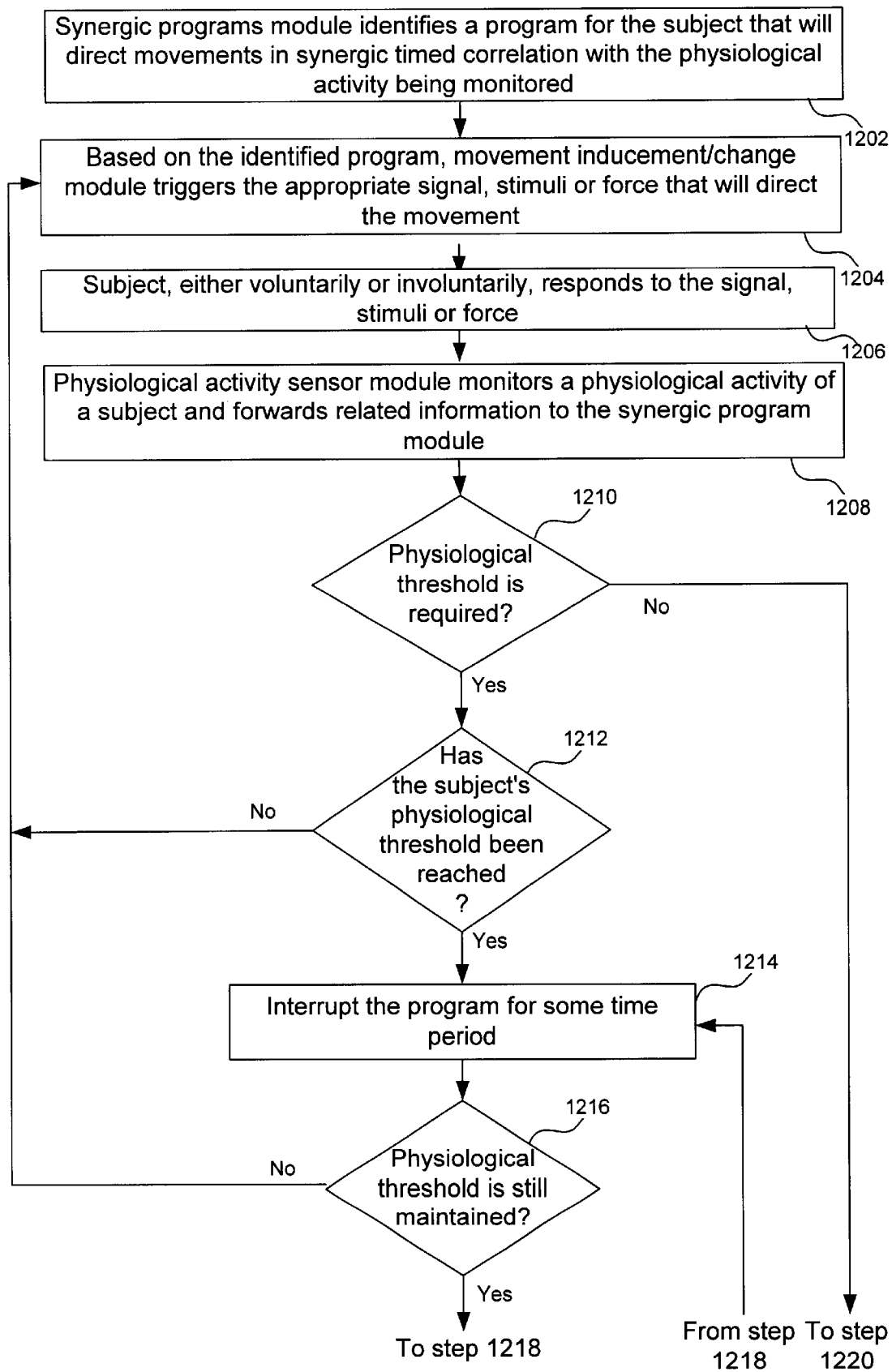
FIGS. 12A and 12B represent the operation of an embodiment of the invention when executing a program for a particular subject according to an embodiment of the invention.
Figure 12B:
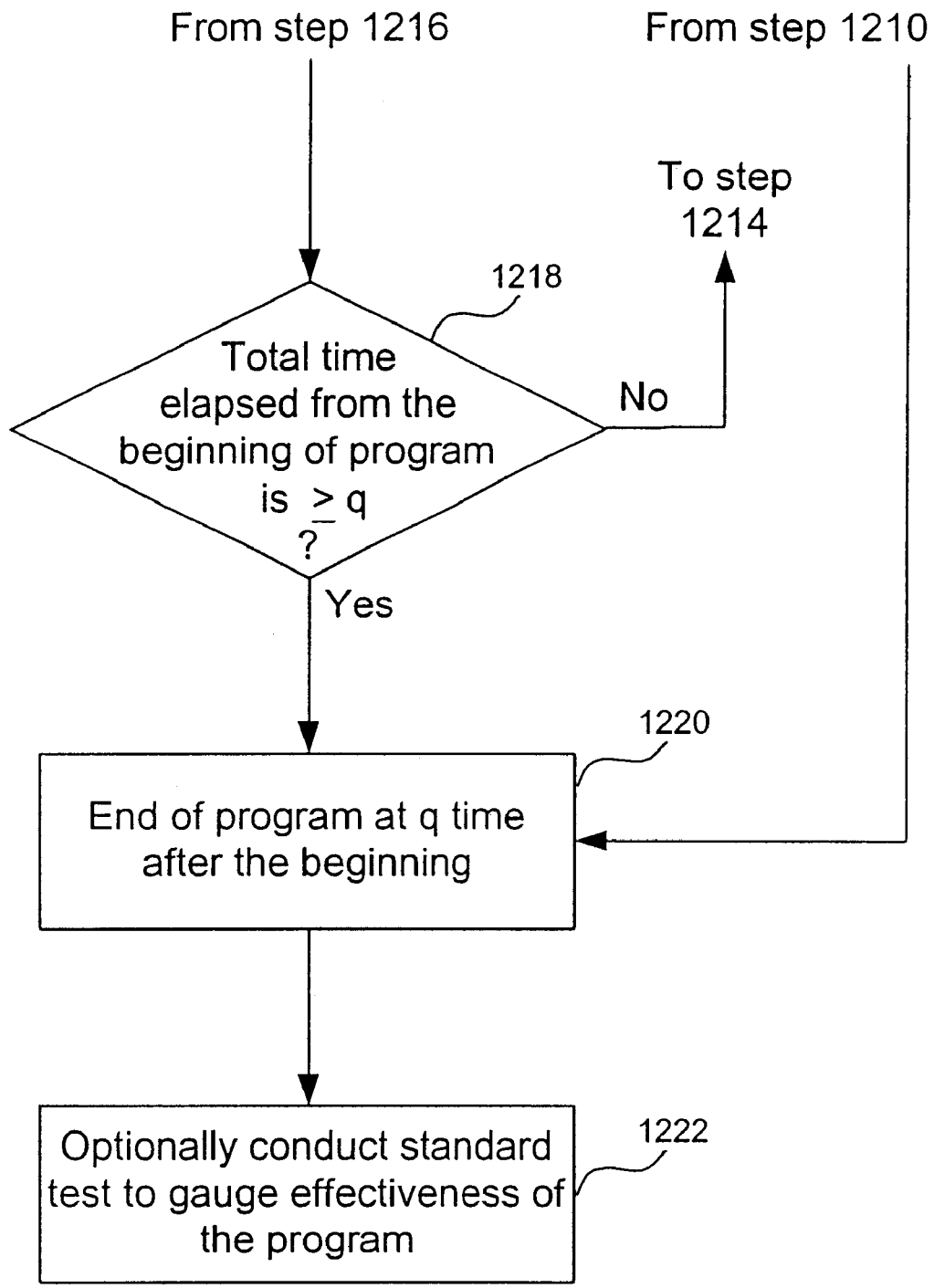

FIGS. 12A and 12B represent the operation of an embodiment of the invention when executing a program for subject 308. It is noted that the flowchart of FIGS. 12A and 12B applies to the embodiments shown in FIGS. 8–10. In FIG. 12A, control starts at step 1202. In step 1202, synergic programs module 304 identifies a program for subject 308 that will direct the movement in synergic timed correlation with the physiological activity being monitored. If the program to be used for subject 308 was pre-stored in synergic programs options module 504 (as explained above with reference to FIG. 11), then synergic engine 506 simply needs to retrieve the program. Alternatively, if synergic engine 506 calculates the program to use on subject 308 on-the-fly, then steps similar to those described with reference to FIG. 11 will be executed at this time. Accordingly in this step, the signal, stimuli or force is selected. Control then passes to step 1204.

In step 1204, based on the program determined by programs module 304 in step 1202, movement inducement/change module 306 conveys or triggers the appropriate signal and/or stimuli and/or force that will direct the movements. "Synergic timed correlation" relates to monitoring the variability within and between the cycle of a physiological activity of the subject and then inducing the subject to perform a voluntary or involuntary movement in a variably timed fashion following those variabilities. This "variably timed fashion" is such that the time variability of the movement is primarily correlated with the variability of the physiological activity cycle but including an additional artificial variability by a secondary correlation in such a way that the physiological activity and the induced movements are not synchronized or entrained during all the time but in an intermittent fluctuating manner. In order for the movement to be performed in a "variably timed fashion," there must be some sort of signal, stimuli or force prompting the movement to occur that is directed towards the subject. Control then passes to step 1206.

In step 1206, subject 308 either voluntarily or involuntary responds to the signal and/or stimuli and/or force (depending on the program and particular signal and/or stimuli and/or force being used). While subject 308 performs the correlated movements, the motoric system of subject 308 possibly becomes involved in a biomechanical process that is unique to subject 308. Because the time series generated by the physiological cycle and sub-cycles with which synergic movements is aimed to be established can be assumed to be unique to subject 308, it is inferred that the process by which their synergism is reached and maintained could also be unique. Control then passes to step 1208.

In step 1208, physiological activity sensor module 302 monitors physiological activity of subject 308 and forwards related information to synergic programs module 304. Presumably, the subject's response in step 1206 will be reflected to a certain extent in the subject's physiology, a change which would be obtained through sensor module 302. Step 1208 is described in more detail below with reference to FIG. 13. Control then passes to step 1210.

In step 1210, the information from step 1208 is analyzed in synergic engine 506 if so required by the program, to determine whether the physiological threshold of subject 308 has been reached. Physiological threshold refers to the values (minimal and/or maximal) of a physiological variable. These values define boundaries that the administrator and/or engine 506 decide the subject should not cross while performing the synergic movements.

Preferably, physiological variables should be those reflecting physical and/or cognitive and/or emotional stress, including those variables related to perceptual and attention mechanisms. One choice could be the heart rate and its intrinsic variability. There are many parameters of heart rate variability (HRV). One of them is the Root Mean Square of Successive Differences (RMSSD) between RR intervals. The heart rate is defined by the quantity of successive RR intervals taking place in one minute. Heart rate and/or RMSSD can be measured on line in real time by engine 506, by simple calculations performed with RR interval measurement data obtained and stored by engine 506. If a threshold, then is required control passes to step 1212. If a threshold is not required, then control passes to step 1220.

If control passes to step 1212, then it is determined whether the subject's physiological threshold has been reached. If the outcome is positive, then control passes to step 1214. Alternatively, the control passes back to step 1204 and continues until the subject's physiological threshold has been reached.

In step 1214 the program is interrupted during a short time interval p, which was previously established at modulus 504 together with the total time q allowed for the program. After the interval p elapsed control goes to step 1216 where physiological variable is again measured to verify determine whether the threshold is still remained. If the outcome is negative, then control passes back to step 1204. Otherwise, control passes to step 1218, where total time in the program from its beginning is measured to verify if the time limit q has been reached. If the outcome is negative, control goes back to step 1214. If it is positive, control goes to step 1220 and the program ends. Optionally, control passes to step 1222 where tests to gauge the effectiveness of the program are carried out.

In an embodiment, the synergic timed correlation of physiological activity and movements as specified in the program may result in physical activity and/or abilities that prior to operation was not been achievable by subject 308 (e.g., athletic performance in competitions where the subject becomes so stressed that even simple (or heavily practiced) tasks become impossible or near impossible). If the relationship between the increase of physiological stress (measured for example by one or more heart rate or heart rate variability or electrocortical activity, etc) and the correlative increase in bio-motoric performance for a task requiring attentional effort, is above some threshold value, the natural decrease of attention power ensuing in real time from the increase in physiological stress will necessarily preclude bio-motoric performance to significantly increase above its pre-task level. By achieving a higher degree of synergic level among the parts of the body, the relative physiological stress for the same task is expected to decrease by which the above relationship will also decrease and new types of physical activity and/or new abilities may be achievable by subject 308. The flowchart in FIGS. 12A and 12B ends after completion of step 1222.

6.3.1. Monitoring Physiological Activity of a Subject

FIG. 13 describes step 1208 (FIG. 12A) in more detail relating to physiological activity sensor module 302 monitoring a physiological activity of subject 308. In FIG. 13, control starts at step 1302. In step 1302, physiological sensor 402 monitors the physiological activity of subject 308 and forwards the signals representative of such physiological activity to signal conditioning module 404.

Physiological sensors 402 may be comprised of one or more of those currently used in the art, or developed in the future, including but not limited to, those used in reography or doppler techniques or in, photoplethysmography devices to detect the arterial and/or venous pulse, and/or in those used to detect changes in galvanic skin resistance and/or those to measure blood pressure, and/or in those used to currently detect the ECG or those to detect electro-cortical EEG activity and/or those to detect the periodic chest movements due to the breathing activity. Physiological sensors 402 encompass the above examples and also, in general, any other sensors currently existing or to be developed in the future by which signals representative of physiological activity of the heart and/or brain and/or lungs and/or the autonomic nervous system and/or hormonal and/or of any other physiological activities could be directly or indirectly detected. Control then passes to step 1304.

In step 1304, signal conditioning module 404 processes the signals to transform them to a form useable by synergic programs module 304. Signal conditioning module 404 performs a number of steps well known in the art comprising, but not limited by, the steps of amplifying, filtering, multiplexing and converting analog signals to digital signals or vice versa, protocol and/or language conversions, etc. Control then passes to step 1306.

In step 1306, physiological information is then transmitted directly or by wireless means to programs module 304 (FIG. 3). The flowchart in FIG. 13 ends at this point.

6.4. Example—Determining Signal Timing To Correlate Movement With Physiological Activity As discussed above with reference to FIG. 11, in step 1110 the timings of the signal, stimuli or force are determined. This section describes an example implementation of step 1110. As described above, to obtain synergic timed correlation at least two major steps must be performed. First, achieve some level of synchronization of movement with the physiological activity (which is naturally variable). This primary correlation will necessarily decrease the movement's level of freedom, but allows for improvement in perceptual attention mechanisms. See step 1402 of FIG. 14.

Second, assign an artificial variability to the timings of movement by incorporating into such timings an extra additional temporal variability. This additional variability consists in a secondary correlation aimed to: i) produce fluctuations in time parameters values of the synchronization or primary correlation in order to achieve "relative coordination" which is a necessary condition for synergism to take place; ii) compensate the reduction in the movements' degrees of freedom produced by the primary correlation. Furthermore, in order to promote variability, a program should contain more than one type of movement as well as changes in the context of the same type of movement. See step 1404 of FIG. 14.

The secondary correlation is implemented by assigning fluctuations in the timing of movement. These fluctuations are: i) embedded in each of the timing parameters ($t_D$ and $S_T$) of the synchronization, and ii) expressed by an algorithm defining when the following $t_D$ and $S_T$ will take place (Step 1610 in FIG. 16). These two parameters are shown in the example of FIG. 15A. An electrocardiogram (ECG) is depicted in FIGS. 15A and 15B where the QRS wave complex identifies the depolarization of the heart ventricles, the T wave their repolarization and the P wave the heart atrial depolarization. The electromechanical systole starts at the Q point and ends around the end of the descending slope of the T wave. The mechanical systole starts few tens of milliseconds after the S point in the ECG and ends together with the electromechanical systole. From this point starts the diastole, when the ventricles regain about the same amount of blood expelled during the mechanical systole. Diastole ends at the Q point. The signal, stimuli or force is delivered during an interval $S_T$, which could be located in the diastolic or systolic subcycle of the heart by controlling the delay $t_D$ from a fiducial point chosen inside the QRS complex.

In FIG. 15A, $t_D$ is equal to D1+D2 (where both or either D1 or D2 is variable). In addition, $S_T$ is equal to S1+S2 (where both or either S1 or S2 is variable). FIG. 16 represents the operation of the invention when performing step 1110 (FIG. 11), and is described with reference to FIG. 15A.

In the exemplary implementation of FIGS. 15A and 16, assume that the physiological activity being monitored is the heart cycle. Further assume that the program involves voluntary, active participation on the part of subject 308. It is also assumed that the determined movement is a handgrip (right, left and/or both). The handgrip is to be performed by subject 308 as simultaneously as possible with the start and the end of a signal timed according to parameters $t_D$ and $S_T$, and perceived by subject 308 on, for example, a screen. Also assume that the signal is a visual type and the signal comprises letter signals of group classification III (from FIG. 6 and table 600).

Referring to FIG. 6, there are 16,848 such signals that differ from each other in respect to size and/or color and/or font, etc. Irrespective of which of the 16,848 possible different signals is displayed on the screen of movement inducement/change module 306 (FIG. 3), the interval $S_T$ and the ensuing voluntary handgrip by subject 308 will be synergically correlated with the heart cycle, as described next with reference to FIG. 16. The way this is done in an embodiment of the invention shall now be described with reference to FIGS. 15A and 16.

In FIG. 16, control starts at step 1602. In step 1602, synergic engine 506 measures each RR interval in milliseconds. Control then passes to step 1604. To define a first RR cycle at which the first correlated movement will be executed, the measurement of a number of previous and preferably unperturbed RR intervals is required, in order for engine 506 to perform some preliminary calculations. Besides, experience shows that about 2 minute is required to obtain a relatively stable heart beat after an even relatively small change in a previous physical, cognitive or emotional condition of the subject has taken place. Assuming that the subject may repeat the program for several times, by starting movements always after the same interval from the beginning, may introduce the subject's anticipated knowledge of when the first movement should be done, raising an awareness embedded in cognitive and emotional processes that should be avoided. In this embodiment, a practical solution is attained by dividing the pre-movement interval in steps 1604 and 1606 as will be now explained.

In step 1604, synergic engine 506 counts an initial series of preferably not less than twenty-seven (27) successive RR intervals. Note that the present invention is not limited to an initial series of 27 successive RR intervals. In fact, other numbers of initial series of successive RR intervals can be defined by the administrator and/or engine 506 and may be used as long as the number conforms to the above stated logic. Control then passes to step 1606.

In step 1606, synergic engine 506 utilizes a quasi-random function to determine how many additional RR intervals (preferably not less than 1–8) will be added to the initial twenty-seven intervals from step 1604. The sum of the 27 initial intervals and the number of additional intervals is referred to as "n". In this way n is not always the same and of around 30 heart cycles about ½ a minute, as explained above. Control then passes to step 1608.

In step 1608, on the following RR interval (i.e., the n+1 interval), synergic engine 506 commands the movement inducement/change module 306 (FIG. 3) to trigger the display of a randomly selected signal, e.g., the depiction of a letter of the alphabet (from Group Classification III) to subject 308. This particular interval is defined by the present invention as an operative RR interval ("ORR"). Therefore, ORR is equal to $R_{n+1}$. Signals are delivered to subject 308 according to a timing defined by parameters $t_D$ and $S_T$, as shown in FIG. 15A and indicated in FIG. 16. The letter is randomly selected in order to induce the subject to renounce cognitive, attentional engagement in relation to the letter, as explained elsewhere herein. Control then passes to step 1610.

In step 1610, synergic engine 506 determines the next ORR. The number of RR intervals Z between two successive ORR may fluctuate, for example, between 0 and 7. Nevertheless, this 7 limit value may be defined by the administrator at modulus 504 or by engine 506 if it is derived from an expert system. Its actual value will be calculated after the value of the last $S_T$ has been defined. Calculation is done by a random or any other function, as also the administrator (or the expert system) may define.

In this embodiment the mean RR will be calculated from a running window of 10 RR intervals. In any case this value of 10 can be changed by the administrator (at modulus 504).

In this particular embodiment, the mean RR (mRR) will be calculated as follows:

$$MRR = \frac{\sum_{p=n-9}^{p=n} RR_p}{10}$$

Then, starting at a previously defined fiducial point in the QRS complex, a delay $t_D$ will take place before the visual signal will be generated, to last during an interval $S_T$, by movement inducement/change module 306. This delay $t_D$ depends on the synergic timing mode of the primary correlation of the movement. In an embodiment of the present invention, $t_D$ is calculated by the following expression for mode 1:

$$t_{D1} = mRR - \theta - \left( \frac{|RMSSD| + |RRn - RR_{n-1}|}{2} \right)$$

Where $\theta$ is a value in millisecond depending on the mRR calculated from the 10RR intervals preceding the ORR (and obtained by synergic engine 506 from a pre-stored table in module 504). Note that the way of calculating $\theta$ described herein, and all other values, is just one way of many possible ways and is not meant to limit the present invention. RMSSD is the root mean square of preferably the 10 successive differences (of the eleven RR intervals) preceding the ORR in order to compare its changes with those of the mRR. In any case, this default number of RR intervals can be changed by the administrator at modulus 504 or expert system at synergic engine 506. RMSSD is the Von Neuman algorithm:

$$RMSSD = \sqrt{\frac{\sum_{p=n-10}^{p=n} (RR_p - RR_{p-1})^2}{10}}$$

For mode 2, $t_{D2}$ is calculate by the following expression: $t_{D2}=K+q\delta$. Where for example K has a default value of 30 millisecond, $\delta$ a default value of 15 millisecond, and q is a factor number from 0 to U, and can be determined by the quasi-random or any other function at each incoming ORR. Values of K, $\delta$ and U can be defined by the administrator at modulus 504 or an expert system at engine 506.

Furthermore, the interval $S_t$ is obtained by the expression $S_T=T_K+q\delta$. Here, $T_K$ is a constant value in milliseconds depending on the operant synergic timing mode (M1 or M2), and on the mRR preceding the particular ORR where the $S_T$ takes place. Synergic engine 506 obtains the $T_K$ value from a pre-stored table (or via an algorithm) at modulus 504. In this example, the factor q and $\delta$ are equivalent as in the equation above for $t_D$ in mode 2, although their values could be different. Simmilarly, the values of $\delta$ and U can be defined by the administrator at modulus 504 or an expert system at synergic engine 506 in the form of a table or derived on-the-fly by an algorithm.

In the particular case of embodiments of the present invention where voluntary/active synergic movements are to be executed by the subject, there will be a delay between for example, the perceived visual signal and/or sound stimuli reaching the sensorial system of the subject (during $S_t$) and the actual execution of the movement. This delay is called reaction time (RT). The timing of the occurrence of the synergic movement is represent in FIG. 15A. The synergic movement (SYM) is represented in FIG. 15A as time delayed in relation to the $S_t$. When correlating with the heart cycle this delay is significant, because it takes generally more than 300 msc. For the movement to take place during systole, $S_T$ should come up on the preceding diastole, for example. For when a synergic movement will be achieved, it is predicted that the RT should decrease. Some embodiments provide new research tools to investigate changes in reaction time under different biomechanical condition for normal people and for those with, for example, attention deficit disorders (ADD).

As it is well known in the relevant arts, each of the variables described herein may have a range of possible values. This range of possible values may be pre-calculated and pre-stored in a table for look-up by the present invention as necessary. Alternatively, the value of each variable may be generated on-the-fly via an algorithm.

7. Embodiments of the Present Invention

As described above, the present invention involves both the voluntary and/or involuntary movements of the subject, resulting in various embodiments of the present invention. These various embodiments were introduced in Table 1 above, illustrating: (1) the voluntary class is further divided into two subclasses, including active and reactive, and (2) the involuntary class is further divided into two subclasses, including passive and reflexive. It is important to note that some of the embodiments described herein are hybrids of different combinations. Examples of specific embodiments for each of the class/subclass combinations are described next. Such embodiments represent devices, for example tools that the invention employs to cause subject 308 to make desired movements.

7.1. Class: Voluntary; Subclass: Active

Embodiments of the voluntary/active combination of the present invention comprise at least the following types: (1) tools, (2) fitness, and (3) sports.

7.1.1. Tools

Various types of tools can be used by the voluntary/active combination of the invention, including but not limited to: eating tools, writing tools and home improvement tools. Eating tools may include a fork, spoon, knife, chopsticks, etc. Writing tools may include a pencil, pen, paintbrush, stylus, sculpturing tools, etc. Home improvement tools may include a hammer, screwdriver, saw, etc. The voluntary/active combination of the invention may be implemented in a similar way in each of the tools mentioned above. FIG. 17 illustrates an embodiment involving voluntary/active combination as implemented in a hammer 1702.

Referring to FIG. 17, subject 308, physiological activity sensor module 302, movement inducement/change module 306 (implemented inside of a hammer 1702), and synergic programs module 304 are shown. Physiological activity sensor module 302 may be implemented as a bracelet 1704 worn on the arm of subject 308 (as shown in FIG. 17). Alternatively, physiological activity sensor module 302 may be worn around the waist, finger or leg of subject 308. It should be apparent to one skilled in the relevant art(s) that physiological activity sensor module 302 may be worn in many ways by subject 308, or may be a sensor not physically attached to subject 308, all of which are contemplated by the present invention and apply to all of the embodiments described herein (where applicable).

Assume that the voluntary/active program to be executed by synergic programs module 304 for subject 308 includes the following: the determined movement is a strike on the head of a nail with hammer 1702, and the strike by hammer 1702 is to be performed by subject 308 as simultaneously as possible with the start and the end of a signal perceived by subject 308 that originates from hammer 1702 (i.e., that originates from movement inducement/change module 306 and more specifically, from sensorial signals and stimuli module 702 (FIG. 7)). The signal could be a vibration, a flashing light, a sound, etc. In another embodiment of the present invention, movement inducement/change module 306 may be located external to hammer 1702.

It will be apparent to persons skilled in the art that the other tools mentioned above could be implemented in a similar manner. For example, if a fork was used to house movement inducement/change module 306, then the determined movement may be to eat a piece of food each time a signal originated from the fork. Likewise, if the tool was a pen, then the determined movement may be to draw a line each time a signal originated from the pen.

7.1.2. Fitness

Various types of fitness can be utilized by the voluntary/active combination of the invention including, but not limited to, stretching. FIG. 18 illustrates an embodiment involving voluntary/active combination as implemented via stretching.

Referring to FIG. 18, physiological activity sensor module 302 and synergic programs module 304 are housed inside a belt 1802 worn by subject 308. Here, movement inducement/change module is external to belt 1802 worn by subject 308. Again, it should be apparent to one skilled in the relevant art(s) that physiological activity sensor module 302 and synergic programs module 304 may be worn in many ways by subject 308, or may not be in physical contact with subject 308.

Assume that the voluntary/active program to be executed by synergic programs module 304 for subject 308 includes the following: the determined movement is a slight stretching movement by subject 308, and the stretch is to be performed by subject 308 as simultaneously as possible with the start and the end of a signal perceived by subject 308 that originates from the external movement inducement/change module 306 (and more specifically, sensorial signals and stimuli module 702 (FIG. 7)). The signal could be a flashing light, a sound, a display of a symbol on a screen, etc.

In another embodiment of the present invention, movement inducement/change module 306 may also be housed inside of a belt 1902 worn by subject 308, as shown with reference to FIG. 19. Here, the signal could be a vibration, a sound, heat, etc.

The present invention may utilize a walkman to increase the synergy between the voluntary movements of subject 308 and his or her physiological activity. Referring to FIG. 30, physiological activity sensor module 302 and synergic programs module 304 are housed inside a belt 3004 worn by subject 308. Here, movement inducement/change module 306 is housed in a walkman 3002 worn by subject 308. Again, it should be apparent to one skilled in the relevant art(s) that physiological activity sensor module 302 and synergic programs module 304 may be worn in many ways by subject 308, or may not be in physical contact with subject 308 or may also be housed in walkman 3002.

Assume that the voluntary/active program to be executed by synergic programs module 304 for subject 308 includes the following: the determined movement is a jogging, walking, dancing, etc., movement by subject 308, and the movement is to be performed by subject 308 as simultaneously as possible with the start and the end of a signal (e.g., the start of music or conversation, or alternatively the stopping of music or conversation) perceived by subject 308 that originates from the movement inducement/change module 306 housed in walkman 3002. The signal is typically the start of music or conversation.

7.1.3. Sports

As described above, different types of sports can be utilized by the voluntary/active combination of the invention including, but not limited to, swinging a golf club, free throwing, shooting an arrow, weight lifting, ball kicking, pitching a ball, etc. FIG. 20 illustrates an embodiment involving voluntary/active combination as implemented by kicking a ball 2002.

Referring to FIG. 20, physiological activity sensor module 302 is housed inside of a belt 2004 worn by subject 308. Movement inducement/change module is housed inside a strap 2006 around the leg of subject 308. Here, synergic programs module 304 is external to both belt 2004 and strap 2006 worn by subject 308. These devices communicate via wireless means. It should be apparent to one skilled in the relevant art(s) that physiological activity sensor module 302 and movement inducement/change module 306 may be housed in the same belt or strap.

Assume that the voluntary/active program to be executed by synergic programs module 304 for subject 308 includes the following: the determined movement is a movement to kick a ball 2002, and the kick is to be performed by subject 308 as simultaneously as possible with the start and lasting until the end of a signal perceived by subject 308 that originates from strap 2006 (i.e., movement inducement/change module 306). The signal coming from movement inducement/change module 306 (and more specifically, sensorial signals and stimuli module 702) could be a vibration, visual indication, sound, etc.

FIG. 21 illustrates another sport, namely swinging of a golf club, that may be utilized by the voluntary/active combination of the invention. Here, physiological activity sensor module 302 is housed inside of a belt 2104 worn by subject 308. Movement inducement/change module 306 is housed inside a golf tee 2102. Synergic programs module 304 is external to both belt 2104 and golf tee 2102. These devices communicate via wireless means.

Assume that the voluntary/active program to be executed by synergic programs module 304 for subject 308 includes the following: the determined movement is a swing of a golf club at a ball, and the swing is to be performed by subject 308 as simultaneously as possible with the start and lasting until the end of a signal perceived by subject 308 that originates from tee 2102 (i.e., movement inducement/change module 306). The signal coming from movement inducement/change module 306 (and more specifically, sensorial signals and stimuli module 702) could be visual or audio, for example embodiments of the voluntary/reactive combination of the invention will be described next.

7.2. Class: Voluntary; Subclass: Reactive

Embodiments of the voluntary/reactive combination of the present invention comprises at least the following types of equipment: (1) treadmill, (2) balance platform, and (3) exercise bike. FIG. 22 illustrates an embodiment involving voluntary/reactive combination as implemented in a treadmill 2202.

Referring to FIG. 22, physiological activity sensor module 302 and synergic programs module 304 are housed in handle bars 2204 where subject 308 may rests his or her hands. Movement inducement/change module 306 is housed in base 2206 of platform 902 (here implemented as a treadmill).

Assume that the voluntary/reactive program to be executed by synergic programs module 304 for subject 308 includes the following: the determined movement is the subject's biomechanical accommodation to changes in the velocity of platform 902 (i.e., treadmill), and the accommodation is performed by subject 308 together with the start and the end of a change in the velocity of platform 902 (i.e., treadmill) (i.e., from movement inducement/change module 306, and more specifically, stimuli and physical forces module 704 (FIG. 70)). Thus, subject 308 must react to the change in velocity of platform 902 (i.e., treadmill) and simultaneously voluntarily adapt his/her biomechanical activity in order to continue with the treadmill/exercise.

It will be apparent to persons skilled in the art that a balance platform and exercise bike could be implemented in a similar manner. For example, if a balance platform was used to house movement inducement/change module 306, then the determined movement may be for subject 308 to voluntarily react in order to maintain balance on the platform. Likewise, if an exercise bike housed the movement inducement/change module 306, then the determined movement may be for subject 308 to peddle harder during the interval when the resistance of the exercise bike increases (or lighter if the resistance decreases).

7.3. Class: Involuntary; Subclass: Passive

Embodiments of the involuntary/passive combination of the present invention comprises at least the following types of equipment: (1) furniture, (2) transportation, (3) music, (4) toys and (5) musical. Furniture includes, but is not limited to, such items as beds, pillows, chairs (rocking and stationary), cradles, and porch swings. Transportation is similar to furniture and includes, but is not limited to, seats, footrests and steering wheels in automobiles, trains, busses, and planes (where applicable). Music includes radios, televisions, instruments, and headphones (to listen to music or conversation). FIG. 23 illustrates an embodiment involving involuntary/passive combination as implemented in platform 1002 (i.e., a bed) according to an embodiment of the invention.

Referring to FIG. 23, physiological activity sensor module 302 is housed in a belt 2306 worn around the waist of subject 308. Synergic programs module 304 and movement inducement/change module 306 are external to physiological activity sensor module 302. A motion module 2302 is used to physically rock or move platform 1002 (here, a bed) where that subject 308 lies or rests. Note that in the involuntary/passive combination, subject 308 is not required to initiate any movement, but his/her sensorial system is required to produce some degree of sensorial awareness of the movements to which the body is being subjected. This awareness may result from afferent and/or efferent neural activity. /Assume that the involuntary/passive program to be executed by synergic programs module 304 for subject 308 includes the following: the determined movement is the rocking of platform 1002 (i.e., bed) by motion module 2302 when signaled to do so by movement inducement/change module (more specifically, stimuli and physical forces module 704 (FIG. 7)).

It will be apparent to persons skilled in the art that platform 1002 described with reference to FIG. 23 may also be implemented using pillows, chairs (rocking and stationary), cradles, and porch swings, and transportation items (seats, footrests and steering wheels in automobiles, trains, busses, and planes (where applicable)) could be implemented in a similar manner.

7.4. Class: Involuntary; Subclass: Reflexive

Embodiments of the involuntary/reflexive combination of the present invention comprises at least the following types of equipment: (1) showerheads (water and radiation), (2) hydrotherapy baths, and (3) some addiction treatments. Some addiction treatments include the use of mechanical candy and straws to treat smoking, drinking and eating addictions. First, FIG. 24 illustrates an embodiment involving involuntary/reflexive combination as implemented in a water showerhead 2402 according to an embodiment of the invention.

Referring to FIG. 24, physiological activity sensor module 302 is housed in a belt 2404 worn around the waist of subject 308. Movement inducement/change module 306 is housed in a showerhead 2402. Synergic programs module 304 is external to both physiological activity sensor module 302 and movement inducement/change module 306. Note that in the involuntary/reflexive combination, subject 308 is not required to initiate any movement but his or her body reacts in an involuntary reflexive way when certain sensations are produced in his/her body. Similarly as with the involuntary/passive combination, in the involuntary reflexive some degree of sensorial awareness (including propioseptive awareness) to what is taking place on the body is also required.

Assume that the involuntary/reflexive program to be executed by synergic programs module 304 for subject 308 includes the following: the determined signal is a change in the water pressure and/or in skin location and/or in distribution of the impact or in its temperature coming from showerhead 2402 (via movement inducement/change module 306), and the movement is an involuntary reflexive movement from all or any part of the subject 306 when the difference in the water pressure and/or skin location or distribution of the impact and/or in its temperature hits the body of subject 308. As a result, afferent neural activity will reach local and/or spinal and/or brain centers that will trigger involuntary movements in various parts of the body.

This is similar to a radiation shower 2602, as shown in FIG. 26. FIG. 26 illustrates an embodiment involving involuntary/reflexive combination as implemented by a radiation showerhead 2602 according to an embodiment of the invention, where physiological activity sensor module 302 is housed in a belt 2604.

FIG. 25 illustrates an embodiment involving involuntary/reflexive combination as implemented in a hydrotherapy bath 2502 according to an embodiment of the invention. Referring to FIG. 25, physiological activity sensor module 302 and synergic programs module 304 are housed in a strap 2504 worn around the arm of subject 308. Movement inducement/change module 306 is housed in the hydrotherapy bath 2502 in which subject 308 sits.

Assume that the involuntary/reflexive program to be executed by synergic programs module 304 for subject 308 includes the following: the determined signal is a change in the water pressure coming from the hydrotherapy bath 2502 (via movement inducement/change module 306), and the movement is an involuntary reflexive movement from subject 306 for example when the difference in the water pressure hits the body of subject 308.

FIG. 27 illustrates an embodiment involving involuntary/reflexive combination as implemented via a straw 2702 according to an embodiment of the invention. Here, movement inducement/change module 306 is housed in a straw 2702. Physiological activity sensor module 302 and synergic programs module 304 are housed in a belt 2704 around the waist of subject 308. Here, straw 2702 (via movement inducement/change module 306) contains multiple tubes where each tube may release in a synergically timed way a different taste, including sweet, sour, salty and/or bitter tastes.

Assume that the involuntary/reflexive program to be executed by synergic programs module 304 for subject 308 includes the following: the determined signal is a certain taste from one or more of the multiple tubes in the straw 2702, and the movement is an involuntary reflexive movement from all or any part of subject 306 when the taste touches the tongue of subject 308 and results in a reflexive movement of any part of subject 308.

FIG. 31 illustrates an embodiment involving involuntary/reflexive combination as implemented with a mechanical toy 3102 according to an embodiment of the invention. Referring to FIG. 31, physiological activity sensor module 302 and synergic programs module 304 are housed in a strap 3104 worn around the waist of subject 308. Movement inducement/change module 306 is housed in the toy 3102 which is external to subject 308.

Assume that the involuntary/reflexive program to be executed by synergic programs module 304 for subject 308 includes the following: the determined signal is a sudden bark or jumping from toy 3102 (via movement inducement/change module 306), and the movement is an involuntary reflexive movement from the eyes of subject 306 when the jump occurs and an involuntary reflexive movement from the eardrums of subject 308 when the bark occurs.

FIG. 32 illustrates an embodiment involving involuntary/reflexive combination as implemented via headphones 3202 according to an embodiment of the invention. Here, movement inducement/change module 306 is housed in a headphones 3202. Physiological activity sensor module 302 and synergic programs module 304 are housed in a belt 3204 around the waist of subject 308. Here, headphones 3202 (via movement inducement/change module 306) has the ability to change the frequency and/or amplitude of one or more instruments in a musical composition in a synergically timed way with the physiological activity of subject 308.

Assume that the involuntary/reflexive program to be executed by synergic programs module 304 for subject 308 includes the following: the determined signal is a change in frequency and/or amplitude of a particular instrument of a musical composition coming from headphones 3202 (via movement inducement/change module 306), and the movement is an involuntary reflexive movement from all or any part of the eardrum of subject 308 when the change in frequency and/or amplitude reaches the eardrum of subject 308. Note that headphones 3202 may also be a radio that is external to subject 308.

In fact, the embodiment of the invention shown in FIG. 32 is actually a hybrid embodiment that starts in the involuntary class/passive subclass and transitions to the involuntary class/reflexive subclass.

8. Embodiment of the Present Invention for Learning Disabilities

The present invention also provides many different types of embodiments for apparatus and methods, which can be used as new research tools aimed for developing novel devices and methods for the diagnosis and treatment of an ailment. The apparatus and method of the present invention comprises correlating low-cognition attention related movements that is performed in a temporally varying fashion with a physiological activity in a subject with the ailment, wherein as a result of correlating low-cognition attention related movements that is performed in a temporally varying fashion with the physiological activity, the subject's condition is modified (for example, the subject's condition improves). Depending on the ailment, the method can be practiced using different embodiments of the apparatus of the present invention. The method and apparatus of the present invention are suited to investigate new ways for treating learning disorders, for example, dyslexia, although the invention is not limited to this example.

Research by R. Nicolson and A. Fawcett showed that dyslexic persons presented severe problems in simple motor tasks (See, Nicolson, R. I. and Fawcett, A. J., "Dyslexia is More Than a Phonological Deficit," Dyslexia: An International Journal of Research Practice, vol. 1(1), pp. 19–36, 1995). Nicolson, Fawcett and P. Dean found their dyslexic subjects with a deficit in a specific time estimation task, which is believed to be an index of cerebellar functioning, which may also be involved in rapid automatic movements such as rapid eye tracking saccades (See, Nicolson, R. I., Fawcett, A. J. and Dean, P., "Time Estimation Deficits in Developmental Dyslexia, Evidence for a Cerebellar Involvement," Proceedings of the Royal Society, vol. 259, pp. 43–47, 1995). Experimental evidence suggests that other than cognitive processes and the use of sequential information may be the underlying cause of all of these problems, pointing to a timing component as the underlying cause of these problems (See, Everatt et al., "Motor Aspects of Dyslexia, Reading and Dyslexia Visual and Intentional Processes," Chapter V; Routledge, 1999).

Dyslexic persons have been shown to have difficulty with static and dynamic balance, manual dexterity, ball skills, gross and fine motor control and production of simultaneous movements. They may also show a deficit in motor skills required in speed of tapping, head-to-toe placement and rapid successive finger opposition. It has been estimated that approximately fifty percent of sampled dyslexic persons present visual motor deficits that could be long term and hereditary.

Based in the above research findings and on those earlier mentioned in the background, we describe now a particular embodiment aimed to investigate the utility of this invention for learning disabilities in general and the ailment of Dyslexia in particular.

After repeated sessions of about 10–15 minutes duration each, the subject will experience a measurable improvement in his learning disability. This improvement is correlated to an improved "synergy" between his hand/arm movement and those of his oculomotor system with physiological activity. This apparatus and method is also designed for correlating low-cognition attention related motor activity with physiological activity, like those for keeping the body standing at equilibrium on a vertical position despite small fluctuations in the horizontal position of a table on which the subject stands.

As a result of repeated sessions of correlation of the movement(s) with the physiological activity, the subject will exhibit at least one of improved reading ability, and/or improved coordination and/or improved rapid signal discrimination and/or reduce stress and/or reduce energy consumption, which can be tested by standard methods in the art. Besides, they can be correlated with changes in physiological parameters, including changes in heart rate, HRV and electrocortical activity between, before, during and after sessions. Improved neuroconnectivity in the brain, if any, will be reflected by one or more of changes in brain blood flow as reflected by positron emission tomography (PET), and/or by structural brain changes as reflected by magnetic resonance imaging (MRI). The embodiment to be described, a particular variation of an embodiment in the voluntary class, reactive subclass shown at Section 7.2, in reference to FIG. 22, is schematically described in FIG. 29. The embodiment to be described may also fall within the involuntary class, reflexive subclass as will be described below.

In FIG. 29, a subject 308 stands on table 2904 and holds an illuminating pen 2908 in one hand. Physiological sensor module 302 resides inside a belt 2902 whereas synergic program module 304 could be located outside or be integrated into stand 2912 which is held in place by support 2910 which is in turn linked to support 2924 of table 2904. Support 2924 rests on the floor 2926 and is linked to table 2904 through pivotal means located at the center of the table 2904. Means to move up and down the sides of table 2904 may consist in a servo-motor actuator 2906 or any other suitable means like a pneumatic actuator. One or more actuators can be used. Due to pivotal means of support 2924, the actuators will, in fact, tilt the table. As for example, one actuator could tilt the table towards the right or left side of the subject-facing stand 2912, and another actuator may do it towards the front or backsides of subject 308. A few millimeters tilting and back to the horizontal position will take place during the $S_T$ intervals programmed at module 304 and commanded by module 306. The balancing system of subject 308, including cerebellar and vestibular mechanisms, will react in synergic correlation with cyclical visceral activity, like with the heart, for example. At the same time, subject 308 will voluntarily draw a series of simple designs 2918, by copying with pen 2908, as closely as possible, with writing means 2922, on designs 2918 printed on paper 2916 resting on a digitalized 2914 table which lies above stand 2912. Note that depending on the angle that the table tilts, the movement performed by the subject may be reactive where the subject must voluntarily react to keep his or her balance or reflexive where the subject does not have to react voluntarily to keep balance.

One session may include copying a series of papers 2916 containing different designs 2918. The design has to be deprived of meaning content in order to only engage low cognitive attention mechanisms. Pen 2908 holds inside illuminating means, such that at each, and preferably by wireless means commanded by module 306, it illuminates a restricted zone of paper 2916. While copying the line 2918, the occulomotor system of subject 308 will automatically react, at any sudden change on the illumination around the line being copied, in synergic correlation with the heart cycle. Movements of the hands, eyes, both legs and all the balancing system will become in this way synergically correlated with physiological cyclical activity. The digitalized table 2914 is linked, preferably by wireless means to a computer in module 304. It will become apparent to those skilled in the art, that space and time parameters for copy performance can be quantitatively assessed at module 304 by computing data sent by the digitalized table 2914.

Improvements in eye/hand correlation when their movements are not commanded by the free will of subject 308 (he/she notices that are copying) but performed in synergic correlation with the physiological activity, can then be followed in a qualitative and quantitative way.

9. Implementation of the Present Invention in Pacemakers, Bio-mechanic/Prosthesis and Rehabilitation Embodiments of the invention are directed to act as pacemakers adapted to interact with a subject's muscular, skeletal, and/or nervous system. For example, such embodiments may interact or may be integrated with a subject's muscular, skeletal, and/or nervous system, and with the subject's prosthesis. In such embodiments, the invention interacts with the subject's muscular, skeletal, and/or nervous system so as to cause the subject or the subject's prosthesis to move, where such movements includes those executed according to the teachings contained herein. It should be apparent to those skilled in the art that embodiments of the invention may be obtained to aid in the rehabilitation process following surgical interventions, as well as after accident and injuries.

10. Conclusion

While some embodiments of the present invention has been described above, it should be understood that it has been presented by way of examples only, and not meant to limit the invention. It will be understood by those skilled in the art that various changes in form and detail may be made therein without departing from the spirit and scope of the invention as defined in the appended claims. Thus, the breadth and scope of the present invention should not be limited by the above-described exemplary embodiments, but should be defined only in accordance with the following claims and their equivalents. Each document cited herein is hereby incorporated by reference in its entirety.

What is claimed is:

1. An apparatus for promoting movements of a subject, comprising:

a synergic programs module that directs said movements in a temporally varying fashion, wherein said synergic programs module causes generation of at least one signal, stimulus, or force, wherein said movements are performed in response to said at least one signal, stimulus, or force, wherein each of said at least one signal, stimulus, or force is determined so as to reduce meaning and/or emotional content to said subject, wherein each signal and stimulus is from a pool that comprises signals and stimuli that are sensorially understandable or recognizable by said subject, wherein timing of said movements is based on at least a primary correlation factor and a secondary correlation factor;

wherein said primary correlation factor is determined so that said movements are synchronized with referential points of an intrinsically variable cyclical physiological activity;

wherein said secondary correlation factor is determined based on:
  (a) fluctuations based on results of a first function; and
  (b) fluctuations based on a quantity of cycles of said physiological activity elapsing between any two of said movements or any two groupings of said movements, wherein said quantity of cycles is based on results of a second function.

2. The apparatus of claim 1, wherein said movements comprise at least one of:
  (i) all of said subject's body;
  (ii) one or more parts of said subject's body; or
  (iii) any living system or any parts thereof, or any non-living object or any parts thereof, for which said movements produce a sensorial effect on afferent pathways of said subject's body.

3. The apparatus of claim 1, wherein each signal and stimulus is selected from said pool using a quasi-random function.

4. The apparatus of claim 1, wherein each of said groupings comprises one or more of said movements.

5. The apparatus of claim 1, wherein each of said at least one signal, stimulus, or force is determined so as to reduce direct and associative meaning and/or emotional content to said subject.

6. The apparatus of claim 1, wherein at least one of initiation and termination of each movement is based on said at least one signal, stimulus, or force.

7. The apparatus of claim 1, wherein said first function and said second function are each based on at least one linear, non-linear, fractal, deterministic chaos, or quasi-random function.

8. The apparatus of claim 1, wherein said movements comprise changes in state of movement of said subject.

9. A method of promoting movements of a subject in a temporally varying fashion, comprising the steps of:
(1) determining timing of said movements based on at least a primary correlation factor and a secondary correlation factor; and
(2) causing generation of at least one signal, stimulus, or force according to said timing, wherein said movements are performed in response to said at least one signal, stimulus, or force, wherein each of said at least one signal, stimulus, or force is determined so as to reduce meaning and/or emotional content to said subject, wherein each signal and stimulus is from a pool that comprises signals and stimuli that are sensorially understandable or recognizable by said subject;
wherein said primary correlation factor is determined so that said movements are synchronized with referential points of an intrinsically variable cyclical physiological activity; and
wherein said secondary correlation factor is determined based on:
(a) fluctuations based on results of a first function; and
(b) fluctuations based on a quantity of cycles of said physiological activity elapsing between any two of said movements or any two groupings of said movements, wherein said quantity of cycles is based on results of a second function.

10. The method of claim 9, wherein each signal and stimulus is selected from said pool using a quasi-random function.

11. The method of claim 9, wherein each of said groupings comprises one or more of said movements.

12. The method of claim 9, wherein each of said at least one signal, stimulus, or force is determined so as to reduce direct and associative meaning and/or emotional content to said subject.

13. The method of claim 9, wherein at least one of initiation and termination of each movement is based on said at least one signal, stimulus, or force.

14. The method of claim 9, wherein said first function and said second function are each based on at least one linear, non-linear, fractal, deterministic chaos, or quasi-random function.

15. The method of claim 9, wherein said movements comprise changes in state of movement of said subject.

16. An apparatus for promoting movements of a subject, comprising:
a synergic programs module that directs said movements in a temporally varying fashion, wherein said synergic programs module causes generation of at least one signal, stimulus, or force, wherein said movements are performed in response to said at least one signal, stimulus, or force, wherein timing of said movements is based on at least a primary correlation factor that is determined so that said movements are synchronized with referential points of an intrinsically variable cyclical physiological activity, wherein said timing of said movements is also based on a secondary correlation factor that is determined based on:
(a) fluctuations based on results of a first function; and
(b) fluctuations based on a quantity of cycles of said physiological activity elapsing between any two of said movements or any two groupings of said movements, wherein said quantity of cycles is based on results of a second function.

17. The apparatus of claim 16, wherein each of said groupings comprises one or more of said movements.

18. The apparatus of claim 16, wherein said first function and said second function are each based on at least one linear, non-linear, fractal, deterministic chaos, or quasi-random function.

19. A method of promoting movements of a subject in a temporally varying fashion, comprising the steps of:
(1) determining timing of said movements based on at least a primary correlation factor so that said movements are synchronized with referential points of an intrinsically variable cyclical physiological activity; and
(2) causing generation of at least one signal, stimulus, or force according to said timing, wherein said movements are performed in response to said at least one signal, stimulus, or force, wherein step (1) further comprises:
determining timing of said movements based on at least said primary correlation factor and a secondary correlation factor, wherein said secondary correlation factor that is determined based on:
(a) fluctuations based on results of a first function; and
(b) fluctuations based on a quantity of cycles of said physiological activity elapsing between any two of said movements or any two groupings of said movements, wherein said quantity of cycles is based on results of a second function.

20. The method of claim 19, wherein each of said groupings comprises one or more of said movements.

21. The method of claim 19, wherein said first function and said second function are each based on at least one linear, non-linear, fractal, deterministic chaos, or quasi-random function.

22. An apparatus for promoting movements of a subject, comprising:
a synergic programs module that directs said movements in a temporally varying fashion, wherein said synergic programs module causes generation of one or more triggers, wherein said movements are performed in response to said one or more triggers, wherein timing of said movements is based on at least a primary correlation factor that is determined so that said movements are synchronized with referential points of an intrinsically variable cyclical physiological activity, wherein said timing of said movements is also based on at least a secondary correlation factor that is determined based on:
(a) fluctuations based on results of a first function; and
(b) fluctuations based on a quantity of cycles of said physiological activity elapsing between any two of said movements or any two groupings of said movements, wherein said quantity of cycles is based on results of a second function.

23. An apparatus for promoting movements of a subject, comprising:
a synergic programs module that directs said movements in a temporally varying fashion, wherein said synergic programs module causes generation of one or more triggers, wherein said movements are performed in response to said one or more triggers, wherein timing of said movements is based on at least a primary correlation factor that is determined so that said movements are synchronized with referential points of an intrinsically variable cyclical physiological activity, wherein said intrinsically variable cyclical physiological activity is related to other than said subject.

24. An method for promoting movements of a subject in a temporally varying fashion, comprising the steps of:
  (1) causing generation of one or more triggers based on at least a primary correlation factor that is determined so that said movements are synchronized with referential points of an intrinsically variable cyclical physiological activity; and
  (2) directing said movements in accordance with said triggers, wherein step (1) further comprises the step of: causing generation of said one or more triggers also based on a secondary correlation factor that is determined based on:
    (a) fluctuations based on results of a first function; and
    (b) fluctuations based on a quantity of cycles of said physiological activity elapsing between any two of said movements or any two groupings of said movements, wherein said quantity of cycles is based on results of a second function.

* * * * *

UNITED STATES PATENT AND TRADEMARK OFFICE
CERTIFICATE OF CORRECTION

PATENT NO. : 6,644,976 B2
DATED : November 11, 2003
INVENTOR(S) : Kullok et al.

It is certified that error appears in the above-identified patent and that said Letters Patent is hereby corrected as shown below:

Column 57,
Line 1, please replace "An method" with -- A method --.

Signed and Sealed this

Twenty-first Day of December, 2004

JON W. DUDAS
*Director of the United States Patent and Trademark Office*

UNITED STATES PATENT AND TRADEMARK OFFICE
CERTIFICATE OF CORRECTION

PATENT NO. : 6,644,976 B2 Page 1 of 1
APPLICATION NO. : 09/948792
DATED : November 11, 2003
INVENTOR(S) : Kullok et al.

It is certified that error appears in the above-identified patent and that said Letters Patent is hereby corrected as shown below:

Issue Assignee

<u>Cover Page</u>,
Item (73) insert --Assignee: Epoch Innovations, Ltd., Dublin (IE)--.

Signed and Sealed this

Thirteenth Day of May, 2008

JON W. DUDAS
*Director of the United States Patent and Trademark Office*